US010940111B2

(12) United States Patent
Klein et al.

(10) Patent No.: US 10,940,111 B2
(45) Date of Patent: Mar. 9, 2021

(54) SURFACE TREATMENT BY WATER-SOLUBLE POLYMERS AND LIPIDS/LIPOSOMES

(71) Applicant: Yeda Research and Development Co. Ltd., Rehovot (IL)

(72) Inventors: Jacob Klein, Rehovot (IL); Ronit Goldberg, Rehovot (IL); Jasmine Seror, Rehovot (IL); Weifeng Lin, Rehovot (IL); Reut Mashiach, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 47 days.

(21) Appl. No.: 15/319,005

(22) PCT Filed: Jun. 15, 2015

(86) PCT No.: PCT/IL2015/050606
§ 371 (c)(1),
(2) Date: Dec. 15, 2016

(87) PCT Pub. No.: WO2015/193888
PCT Pub. Date: Dec. 23, 2015

(65) Prior Publication Data
US 2017/0128365 A1    May 11, 2017

Related U.S. Application Data

(60) Provisional application No. 62/012,379, filed on Jun. 15, 2014.

(51) Int. Cl.
*A61K 9/127* (2006.01)
*A61K 9/00* (2006.01)
(Continued)

(52) U.S. Cl.
CPC ............ *A61K 9/127* (2013.01); *A61K 9/0048* (2013.01); *A61K 9/08* (2013.01); *A61K 31/728* (2013.01);
(Continued)

(58) Field of Classification Search
CPC ....................................................... A61K 9/127
See application file for complete search history.

(56) References Cited

U.S. PATENT DOCUMENTS

| 4,613,665 A | 9/1986 | Larm |
| 4,804,539 A | 2/1989 | Guo et al. |

(Continued)

FOREIGN PATENT DOCUMENTS

| EP | 0216453 | 4/1987 |
| EP | 0341745 | 11/1989 |

(Continued)

OTHER PUBLICATIONS

Lee et al (Soft Matter, 2010, 6, 977-983).*
(Continued)

*Primary Examiner* — Benjamin J Packard

(57) ABSTRACT

A method of reducing a friction coefficient of a surface is disclosed herein, comprising attaching a water-soluble polymer to the surface, and contacting the water-soluble polymer with liposomes, thereby coating the surface with an amphiphilic lipid. Further disclosed herein are solutions comprising a water-soluble polymer attachable to the surface, liposomes, and an aqueous carrier, for reducing a friction coefficient of a surface, and methods utilizing same. Articles of manufacture comprising a substrate coated by a water-soluble polymer which is coated by an amphiphilic lipid are also described, as are uses and methods for treating a synovial joint disorder associated with increased articular friction.

19 Claims, 17 Drawing Sheets
(9 of 17 Drawing Sheet(s) Filed in Color)

(51) Int. Cl.

| | | |
|---|---|---|
| A61K 47/32 | (2006.01) | |
| A61K 47/10 | (2017.01) | |
| A61K 47/36 | (2006.01) | |
| A61K 9/08 | (2006.01) | |
| A61K 31/728 | (2006.01) | |
| A61K 31/77 | (2006.01) | |
| A61K 31/79 | (2006.01) | |
| B65D 35/00 | (2006.01) | |
| B65D 75/36 | (2006.01) | |

(52) U.S. Cl.
CPC .............. *A61K 31/77* (2013.01); *A61K 31/79* (2013.01); *A61K 47/10* (2013.01); *A61K 47/32* (2013.01); *A61K 47/36* (2013.01); *B65D 35/00* (2013.01); *B65D 75/36* (2013.01)

(56) References Cited

U.S. PATENT DOCUMENTS

| | | | |
|---|---|---|---|
| 4,810,784 | A | 3/1989 | Larm |
| 4,818,537 | A | 4/1989 | Guo |
| 4,925,017 | A | 5/1990 | Jessen |
| 5,037,677 | A | 8/1991 | Halpern et al. |
| 5,336,518 | A | 8/1994 | Narayanan et al. |
| 5,356,433 | A | 10/1994 | Rowland et al. |
| 5,364,637 | A | 11/1994 | De et al. |
| 5,403,592 | A * | 4/1995 | Hills ............... A61K 31/685 424/450 |
| 5,895,645 | A | 4/1999 | Dabrowski et al. |
| 5,997,517 | A * | 12/1999 | Whitbourne ........ A61L 29/085 424/422 |
| 6,592,907 | B2 | 7/2003 | Karagoezian |
| 6,800,298 | B1 | 10/2004 | Burdick et al. |
| 7,083,803 | B2 | 8/2006 | Peyman |
| 7,638,137 | B2 | 12/2009 | Chauhan et al. |
| 8,273,366 | B2 | 9/2012 | Chauhan et al. |
| 2003/0165015 | A1 | 9/2003 | Jahnke |
| 2004/0171740 | A1 | 9/2004 | Ruberti et al. |
| 2005/0191331 | A1 | 9/2005 | Hunter et al. |
| 2006/0094643 | A1 | 5/2006 | Svirkin et al. |
| 2006/0210511 | A1 | 9/2006 | Stone et al. |
| 2006/0251685 | A1 | 11/2006 | Yu et al. |
| 2006/0270781 | A1 | 11/2006 | Ruberti et al. |
| 2007/0237803 | A1 * | 10/2007 | Cheng .................. A61L 27/18 424/426 |
| 2007/0292496 | A1 | 12/2007 | Herrero-Vanrell et al. |
| 2009/0192478 | A1 | 7/2009 | Soroudi |
| 2010/0098749 | A1 | 4/2010 | Barenholz et al. |
| 2010/0098772 | A1 | 4/2010 | Robinson et al. |
| 2011/0097277 | A1 * | 4/2011 | Jiang .................... C08J 3/075 424/9.322 |
| 2011/0293699 | A1 | 12/2011 | Bennett et al. |
| 2012/0064150 | A1 | 3/2012 | Wisniewski et al. |
| 2012/0121694 | A1 | 5/2012 | Adkins, Jr. et al. |
| 2012/0128763 | A1 | 5/2012 | Maskin |
| 2012/0148667 | A1 | 6/2012 | Callegaro et al. |
| 2012/0238519 | A1 | 9/2012 | Matsumoto et al. |
| 2014/0099343 | A1 | 4/2014 | Sullivan et al. |
| 2017/0119811 | A1 | 5/2017 | Klein et al. |

FOREIGN PATENT DOCUMENTS

| | | |
|---|---|---|
| EP | 0138572 | 7/1990 |
| EP | 0702699 | 3/1996 |
| EP | 1095064 | 5/2001 |
| EP | 1313772 | 5/2003 |
| EP | 1339753 | 9/2003 |
| WO | WO 03/000190 | 1/2003 |
| WO | WO 2008/038292 | 4/2008 |
| WO | WO 2011/158237 | 12/2011 |
| WO | WO 2014/071132 | 5/2014 |
| WO | WO 2015/193887 | 12/2015 |
| WO | WO 2015/193888 | 12/2015 |

OTHER PUBLICATIONS

Klein (Proc. IMechE vol. 220 Part J: J. Engineering Tribology, 691-710). (Year: 2006).*
Goldberg et al (Adv. Mater. 2011, 23, 3517-3521). (Year: 2011).*
Neto et al ((2014), Nanostructured Polymeric Coatings Based on Chitosan and Dopamine-Modified Hyaluronic Acid for Biomedical Applications. Small, 10: 2459-2469). (Year: 2014).*
Goldberg et al (Chemistry and Physics of Lipids 165 (2012) 374-381). (Year: 2012).*
Goddard et al (Prog. Polym. Sci. 32 (2007) 698-725). (Year: 2007).*
Sivan et al (Langmuir 2010, 26(2), 1107-1116). (Year: 2010).*
Das et al (Biomacromolecules 2013, 14, 1669-1677). (Year: 2013).*
International Preliminary Report on Patentability dated Dec. 22, 2016 From the International Bureau of WIPO Re. Application No. PCT/IL2015/050605. (10 Pages).
International Preliminary Report on Patentability dated Dec. 22, 2016 From the International Bureau of WIPO Re. Application No. PCT/IL2015/050606. (8 Pages).
International Search Report and the Written Opinion dated Oct. 6, 2015 From the International Searching Authority Re. Application No. PCT/IL2015/050606.
International Search Report and the Written Opinion dated Sep. 20, 2015 From the International Searching Authority Re. Application No. PCT/IL2015/050605.
Benelli "Systane® Lubricant Eye Drops in the Management of Ocular Dryness", Clinical Ophthalmology, 5: 783-790, 2011.
Berry et al. "Hyaluronan in dry Eye and Contact Lens Wearers", Lacrimal Gland, Tear Film, and Dry Eye Syndromes 2, Chap. 110: 785-790, 1998.
Brochu "Psycho-Chemical Characterization of Layers of Intact liposomes for Drug Release Applications", University of Sherbrooke, Quebec, Canada, Thesis Submitted to the Fulfillment of the Degree of Philosophiae Doctor (Ph.D.), 113 P., Feb. 2008.
Brodie et al. "Biomechanical Properties of Achilles Tendon Repair Augmented With a Bioadhesive-Coated Scaffold", Biomedical Materials, 6(1): 015014-1-015014-16, Feb. 2011.
Chen et al. "Protein Repellant Silicone Surfaces by Covalent Immobilization of Poly(Ethylene Oxide)", Biomaterials, 26: 2391-2399, 2005.
Craig et al. "Importance of the Lipid Layer in Human Tear Film Stability and Evaporation", Optometry and Vision Science, 74(1): 8-13, Jan. 1997.
Davitt et al. "Efficacy in Patients With Dry Eye After Treatment With a New Lubricant Eye Drop Formulation", Journal of Ocular Pharmacology and Therapeutics, 26(4): 347-353, 2010.
Desrochers et al. "Microscale Surface Friction of Articular Cartilage in Early Osteoarthritis", Journal of the Mechanical Behavior of Biomedical materials, 25: 11-22, 2013.
DiTizio et al. "A Liposomal Hydrogel for the Prevention of Bacterial Adhesion to Catheters", Biomaterials, 19: 1877-1884, 1998.
Doughty "Re-Wetting, Comfort, Lubricant and Moisturising Solutions for the Contact Lens Wearer", Contact Lens and Anterior Eye, 22(4): 116-126, 1999.
Fakes et al. "Surface Modification of a Contact Lens Co-Polymer by Plasma-Discharge Treatments", Surface and Interface Analysis, 10: 416-423, 1987.
Gaisinskaya et al. "Hydration Lubrication: Exploring a New Paradigm", Daraday Discussions, 156: 217-233, 2012.
Goldberg et al. "Boundary Lubricants With Exceptionally Low Friction Coefficients Based on 2D Close-Packed Phosphatidylcholine Liposomes", Advanced Materials, 23: 3517-3521, 2011.
Goldberg et al. "Interactions Between Adsorbed Hydrogenated Soy Phsophatidylcholine (HSPC) Vesicles at Physiologically High Pressures and Salt Concentrations", Biophysical Journal, 100: 2403-2411, May 2011.
Goldberg et al. "Liposomes as Lubricants: Beyond Drug Delivery", Chemistry and Physics of Lipids, CPL, 165: 374-381, 2012.
Gulsen et al. "Dispersion of DMPC Liposomes in Contact Lenses for Ophthalmic Drug Delivery", Current Eye Research, 30: 1071-1080, 2005.
Itoi et al. "Effect of Sodium Hyaluronate Ophthalmic Solution on Peripheral Staining of Rigid Contact Lens Wearers", The CLAO

(56) References Cited

OTHER PUBLICATIONS

Journal (Contact Lens Association of Opthalmologists), 21(4): 261-264, Oct. 1995.
Kang et al. "A New Vaginal Delivery System of Amphotericin B: A Dispersion of Cationic Liposomes in a Thermosensitive Gel", Journal of Drug Targeting, 18(8): 637-644, 2010.
Kawano et al. "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis", Arthritis & Rheumatism, 48(7): 1923-1929, Jul. 2003.
Klein "Hydration Lubrication", Friction, 1(1): 1-23, 2013.
Lee et al. "Single-Molecule Mechanics of Mussel Adhesion", Proc. Natl. Acad. Sci. USA, PNAS, 103(35): 12999-13003, Aug. 29, 2006.
Ludwig et al. "The Evaluation of Viscous Ophthalmic Vehicles by Slit Lamp Fluorophotometry in Humans", International Journal of Pharmaceutics, 54: 95-102, 1989.
Mathers "Evaporation From the Ocular Surface", Experimental Eye Research, 78: 389-394, 2004.
Mourtas et al. "Complex Hydrogel Systems Composed of Polymers, Liposomes, and Cyclodextrins: Implications of Composition on Rheological Properties and Aging", Langmuir, 25(15): 8480-8488, Jun. 4, 2009.
Nagarsenker et al. "Preparation and Evaluation of Liposomal Formulations of Tropicamide for Ocular Delivery", International Journal of Pharmaceutics, 190: 63-71, 1999.
Ngai et al. "Friction of Contact Lenses: Silicone Hydrogel Versus Conventional Hydrogel", Life Cycle Tribology, Tribology and Interface Engineering, Series 48: 371-379, 2005.
Nichols et al. "Tear Film, Conatct Lens, and Patient-Related Factors Associated With Contact Lens-Related Dry Eye", Investigative Ophthalmology & Visual Science, 47(4): 1319-1328, Apr. 2006.
Ogsten et al. "The Physiological Function of Hyaluronic Acid in Synovial Fluid; Viscous, Elastic and Lubricant Properties", Journal of Physiology, 119: 244-252, 1953.
Pasquali-Ronchetti et al. "Hyaluronan-Phospholipid Interactions", Journal of Structural Biology, 120: 1-10, 1997.
Radin et al. "Separation of a Hyaluronate-Free Lubricating Fraction From Synovial Fluid", Nature, 288: 377-378, Oct. 24, 1970.
Rennie et al. "Friction Coefficient of Soft Contact Lenses: Measurements and Modeling", Tribology Letters, 18(4): 499-504, Apr. 2005.
Roba et al. "Friction Measurements on Contact Lenses in Their Operating Environment", Tribology Letters, 44(3): 387-397, 2011.
Seror et al. "Articular Cartilage Proteoglycans as Boundary Lubricants: Structure and Frictional Interaction of Surface-Attached Hyaluronan and Hyaluronan-Aggrecan Complexes", Biomacromolecules, 12: 3432-3443, 2011.
Seror et al. "Normal and Shear Interactions Between Hyaluronan-Aggrecan Complexes Mimicking Possible Boundary Lubricants in Articular Cartilage in Synovial Joints", Biomacromolecules, 13: 3823-3832, Oct. 17, 2012.
Simmons et al. "Conditioning of Hydrogel Lenses by a Multipurpose Solution Containing an Ocular Lubricant", CLAO Journal, 27(4): 192-194, Oct. 2001. Abstract.
Sorkin et al. "Origins of Extreme Boundary Lubrication by Phosphatidylcholine Liposomes", Biomaterials, 34: 5465-5475, 2013.
Thai et al. "In Vitro and In Vivo Effects of a Lubricant in a Contact Lens Solution", Ophthalmic & Physiological Optics, 22(4): 319-329, Jul. 2002.
Vecchio et al. "Surfactant Treatment for Osteoarthritis", Rheumatology, 38(10): 1020-1021, Oct. 1999.
Supplementary European Search Report and the European Search Opinion dated Apr. 18, 2018 From the European Patent Office Re. Application No. 15808959.9. (13 Pages).
Supplementary European Search Report and the European Search Opinion dated Feb. 6, 2018 From the European Patent Office Re. Application No. 15810541.1. (11 Pages).
Craig et al. "Effect of a Liposomal Spray on the Pre-Ooular Tear Film", Contact Lens & Anterior Eye 33(2): 83-87, XP026963833. Apr. 2010. p. 84, Left-hand Col., Line 4-11.
Del Castillo et al. "New Formulation Based on Liposomes and Hyaluronic Acid for Dry Eye Treatment", ARVO Annual Meeting Abstract: 1-2, XP055444902. May 2007 Retrieved from the Internet.
Khaireddin "Trockenes Auge bei Kontaklinsentraeger", Der Ophthalmologe 110(6): 511-515, XP055444189, Jun. 2013.
Sindt et al. "Contact Lens Strategies for the Patient with Dry Eye", The Ocular Surface 5(4): 294-307, XP055158015, Oct. 2007.
Communication Pursuant to Rule 164(1) EPC [Supplementary Partial European Search Report and the European Provisional Opinion] dated Jan. 2, 2018 From the European Patent Office Re. Application No. 15808959.9. (15 Pages).
Official Action dated Jun. 7, 2018 From the US Patent and Trademark Office Re. U.S. Appl. No. 15/319,014. (25 pages).
Official Action dated Jan. 29, 2019 From the US Patent and Trademark Office Re. U.S. Appl. No. 15/319,014. (10 Pages).
Examination Report dated Jan. 15, 2019 From the Australian Government, IP Australia Re. Application No. 2015283594. (4 Pages).
Office Action dated Feb. 13, 2019 From the Israel Patent Office Re. Application No. 249573 and Its Translation Into English. (6 Pages).
Communication Pursuant to Article 94(3) EPC dated Jan. 18, 2019 From the European Patent Office Re. Application No. 15810541.1. (4 Pages).
Notification of Office Action and Search Report dated Feb. 2, 2019 From the National Intellectual Property Administration of the People's Republic of China Re. Application No. 201580043754.8 and Its Translation Into English. (36 Pages).
Final Official Action dated Mar. 9, 2020 from the US Patent and Trademark Office Re. U.S. Appl. No. 15/319,014. (12 pages).
Communication Pursuant to Article 94(3) EPC dated Jul. 11, 2019 From the European Patent Office Re. Application No. 15808959.9. (4 Pages).
Official Action dated Jul. 8, 2019 From the US Patent and Trademark Office Re. U.S. Appl. No. 15/319,014. (17 pages).
Notification of Office Action dated Sep. 18, 2019 From the National Intellectual Property Administration of the People's Republic of China Re. Application No. 201580043754.8 and Its Translation Into English. (18 Pages).
Advisory Action dated Jul. 20, 2020 from the US Patent and Trademark Office Re. U.S. Appl. No. 15/319,014. (8 pages).
Communication Pursuant to Article 94(3) EPC dated Jul. 6, 2020 From the European Patent Office Re. Application No. 15810541.1. (6 Pages).
Notification of Office Action and Search Report dated Jul. 2, 2020 From the National Intellectual Property Administration of the People's Republic of China Re. Application No. 201580043754.8 and Its Translation Into English. (34 Pages).
Barbucci et al. "Micro and Nano-Structured Surfaces", Journal of Materials Science: Materials in Medicine, 14(8): 721-725, Aug. 2003.
Kito et al. "Biocompatible Coatings for Luminal and Outer Surfaces of Small-Caliber Artificial Grafts", Journal of Biomedical Materials Research, 30(3): 321-330, Mar. 1996.
Larsson "Biocompatible Surfaces Prepared by Immobilized Heparin or Hyaluronate", Acta Otolaryngologica, 442(Suppl.): 44-49, Jan. 1987.
Lee et al. "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8(12): 3705-3711, Published Online Nov. 10, 2007.
Morra "Biochemical Modification of Titanium Surfaces: Peptides and ECM Proteins", European Cells & Materials, 12: 1-15, Jul. 24, 2006.
Morra "Engineering of Biomaterials Surfaces by Hyaluron", Biomacromolecules, 6(3): 1205-1223, Published on Web Feb. 17, 2005.
Pitt et al. "Attachment of Hyaluronan to Metallic Surfaces", Journal of Biomedical Materials Research, 68A(1): 95-106, Jan. 1, 2004.

(56) References Cited

OTHER PUBLICATIONS

Taglienti et al. "Investigating the Interactions of Hyaluronan Derivatives With Biomolecules. The Use of Diffusional NMR Techniques", Macromoleuclar Bioscience, 6(8): 611-622, Aug. 7, 2006.
Thierry et al. "Radionuclides-Hyaluranonan-Conjugate Thromboresistant Coatings to Prevent In-Stent Restenosis", Biomaterials, 25(17): 3895-3905, Aug. 2004.
Communication Pursuant to Article 94(3) EPC dated Mar. 27, 2020 From the European Patent Office Re. Application No. 15810541.1. (4 Pages).
Interview Summary dated May 14, 2020 from the US Patent and Trademark Office Re. U.S. Appl. No. 15/319,014. (4 pages).
Office Action dated May 19, 2020 From the Israel Patent Office Re. Application No. 249573 and Its Translation Into English. (13 Pages).
Official Action dated Oct. 22, 2020 From the US Patent and Trademark Office Re. U.S. Appl. No. 15/319,014. (26 Pages).

* cited by examiner

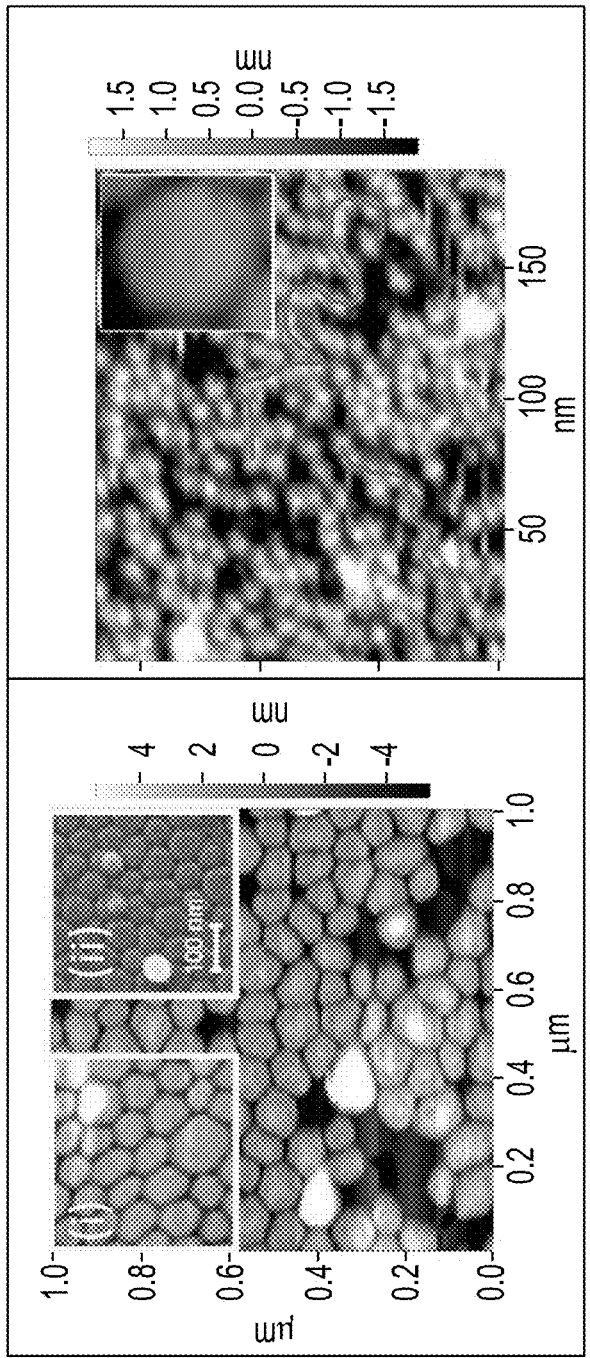
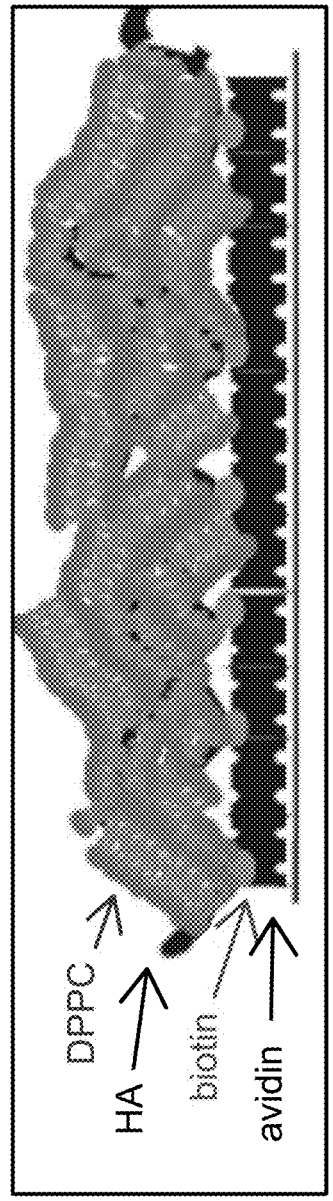
FIG. 9A
FIG. 9B
FIG. 9C

SURFACE TREATMENT BY WATER-SOLUBLE POLYMERS AND LIPIDS/LIPOSOMES

RELATED APPLICATIONS

This application is a National Phase of PCT Patent Application No. PCT/IL2015/050606 having International filing date of Jun. 15, 2015, which claims the benefit of priority under 35 USC § 119(e) of U.S. Provisional Patent Application No. 62/012,379 filed on Jun. 15, 2014. The contents of the above applications are all incorporated by reference as if fully set forth herein in their entirety.

FIELD AND BACKGROUND OF THE INVENTION

The present invention, in some embodiments thereof, relates to material science and, more particularly, but not exclusively, to methods and/or compositions for reducing a friction coefficient of a surface of animate or inanimate objects.

Various attempts to provide low friction conditions in aqueous media, and particularly under physiological conditions for treating, inter alia, joint dysfunction, have been made.

The major mammalian synovial joints, such as hips and knees, exhibit extremely low levels of friction between the articulating cartilage surfaces over a range of shear rates from rest to $10^6$ sec$^{-1}$, up to pressures of order 100 atmospheres, a property which no man-made surfaces can emulate. High friction and corresponding wear of cartilage is a signature of joint pathology [Desrochers et al., *Journal of the Mechanical Behavior of Biomedical Materials* 2013, 25:11-22]. Little is known of the detailed composition or molecular structure of the very outer layer of the superficial zone (SZ) of the cartilage tissue, exposed to the synovial cavity. The boundary lubrication of synovial joints has been attributed to the presence at the surface of hyaluronic acid [Ogston & Stanier, *The Journal of Physiology* 1953, 119: 244-252], lubricin [Radin et al., *Nature* 1970, 228:377-378] and aggrecans [Seror et al., *Biomacromolecules* 2011, 12:3432-3443; Seror et al., *Biomacromolecules* 2012, 13: 3823-3832], but these macromolecules, by themselves or in combination with each other, do not provide particularly good lubrication at physiological pressures [Seror et al., *Biomacromolecules* 2011, 12:3432-3443; Seror et al., *Biomacromolecules* 2012, 13: 3823-3832].

Vecchio et al. [Rheumatology (Oxford) 1999, 38:1020-1021] describe the injection of dipalmitoylphosphatidylcholine (DPPC) lipid surfactant solutions in propylene glycol into joints in an attempt to provide a treatment for osteoarthritis.

U.S. Pat. No. 6,800,298 describes a lubricating composition (i.e. a lubricant) comprising dextran-based hydrogel with lipids.

U.S. Pat. No. 5,403,592 describes a composition comprising a surface active phospholipid and hyaluronic acid in saline solution as being a lubricant suitable for physiological use such as lubrication of joints.

A review by Doughty [*Contact Lens and Anterior Eye* 1999, 22:116-126] describes various re-wetting, conform, lubricant and moisturizing solutions and their potential impact on contact lens wearers. Many of the solutions described therein include polymers such as hydroxypropylmethylcellulose (HPMC; also known as hypromellose), hydroxyethylcellulose, carboxymethylcellulose, polyethylene glycol, poloxamer, polyvinylpyrrolidone (also known as povidone) and hyaluronic acid (HA).

International Patent Application publication WO 2014/071132 describes a contact lens coupled at its surface to a hyaluronic acid-binding peptide, for providing hyaluronic acid to the ocular environment by pretreating the lens with hyaluronic acid and replenishing hyaluronic acid from endogenous or exogenous sources as it is washed away or degraded.

Liposomes are vesicles whose membranes in most cases are based on phospholipid bilayers. They are generally biocompatible and, when modified with other molecules, are widely used in clinical applications, primarily as drug delivery vehicles, as well as in gene therapy and for diagnostic imaging.

International Patent Application Publication WO 2008/038292 discloses, inter alia, multilamellar vesicles or liposomes (MLVs) of several phospholipids above their liquid-crystalline-phase to gel-phase transition temperature (Tm) as possible boundary lubricants in the articular cartilage environment.

International Patent Application Publication WO 2011/158237 discloses, inter alia, a method for lowering the friction coefficient of surfaces, which is effected by applying gel-phase liposomes onto surfaces to form a boundary lubricant layer, wherein the temperature of the surface at the time of lubrication is below the phase transition temperature (Tm) of the liposomes. The method is described as being suitable for lubricating biological and non-biological surfaces, including the surfaces of a biological tissue in a mammalian subject, e.g., for treating joint dysfunction.

Further studies on surface lubrication by liposomes are described in, for example, Gaisinskaya et al. [*Faraday Discuss.* 2012, 156:217-233], Goldberg et al. [*Advanced Materials* 2011, 23:3517-3521], Goldberg et al. [*Chemistry and Physics of Lipids* 2012, 165:374-381] and Goldberg et al. [*Biophys. J.* 2011, 100:2403-2411].

The mechanism of hydration lubrication, whereby hydration layers held by surrounding charges provide effective boundary lubrication even at high pressures, is reviewed by Klein [*Friction* 2013, 1:1-23].

Additional background art includes U.S. Patent Application Publication Nos. 20040171740, 20060270781, 20100098749 and 20110293699; U.S. Pat. Nos. 7,638,137 and 8,273,366; Benelli [*Clinical Ophthalmology* 2011, 5:783-790]; Brodie et al. [*Biomedical Materials* 2011, 6:015014]; Davitt et al. [*Journal of Ocular Pharmacology and Therapeutics* 2010, 26:347-353]; Di Tizio et al. [*Biomaterials,* 1998, 19, p. 1877-1884]; Itoi et al. [*CLAO J.* 1995, 21:261-264]; Ludwig & van Ooteghem [*J. Pharm. Belg.* 1989, 44:391-397]; Mourtas et al. [*Langmuir* 2009, 25:8480-8488]; Kang et al. [*Journal of Drug Targeting* 2010, 18:637-644]; Lee et al. [*PNAS* 2006, 103:12999-13003]; Pasquali-Ronchetti [*Journal of Structural Biology* 1997, 120:1-10]; Simmons et al. [*CLAO J.* 2001, 27:192-194]; Sorkin et al. [*Biomaterials* 2103, 34:5465-5475]; Thai et al. [*Ophthal. Physiol. Opt.* 2002, 22:319-329]; Berry et al. [*Hyaluronan in dry eye and contact lens wearers.* In: Lacrimal Gland, Tear Film, and Dry Eye Syndromes 2, D. A. Sullivan, D. A. Dartt and M. A. Meneray, Editors. 1998, Plenum Press, NY, pp. 785-790]; and Brochu, Ph.D. Thesis in the Université de Sherbrooke, Canada, 2008, Id.: 50177338.

SUMMARY OF THE INVENTION

According to an aspect of some embodiments of the invention, there is provided a method of reducing a friction coefficient of a surface, the method comprising contacting the surface with a solution comprising at least one water-soluble polymer, liposomes, and an aqueous carrier, wherein the water-soluble polymer and the surface are selected such that the water-soluble polymer is attachable to the surface.

According to an aspect of some embodiments of the invention, there is provided a method of reducing a friction coefficient of a surface, the method comprising attaching at least one water-soluble polymer to the surface, and contacting the at least one water-soluble polymer with liposomes, thereby effecting coating of the surface by an amphiphilic lipid of the liposomes.

According to an aspect of some embodiments of the invention, there is provided an article of manufacture comprising a composition-of-matter, the composition-of-matter comprising a substrate coated, on at least a portion of a surface thereof, by at least one water-soluble polymer, the at least one water-soluble polymer being coated by an amphiphilic lipid comprising at least one charged group, wherein at least a portion of molecules of the amphiphilic lipid are oriented such that charged groups thereof face outwards at a surface of the composition-of-matter.

According to an aspect of some embodiments of the invention, there is provided an article of manufacture comprising a composition-of-matter, the composition-of-matter comprising a substrate coated, on at least a portion of a surface thereof, by at least one water-soluble polymer, the article of manufacture being identified for use in efficiently attaching thereto an amphiphilic lipid so as to reduce a friction coefficient of the substrate.

According to an aspect of some embodiments of the invention, there is provided a solution for reducing a friction coefficient of a surface according to a method described herein, the solution comprising the at least one water-soluble polymer, the liposomes, and the aqueous carrier.

According to an aspect of some embodiments of the invention, there is provided a use of a solution described herein in the manufacture of a medicament for treating a synovial joint disorder associated with an increased friction coefficient of an articular surface in the synovial joint.

According to some embodiments of the invention, a molar percentage of phosphatidylcholine in the liposomes is at least 50%.

According to some embodiments of the invention, a concentration of phospholipids of the liposomes in the solution is in a range of from 0.5 mM to 500 mM.

According to some embodiments of the invention, the liposomes are selected from the group consisting of small unilamellar vesicles, large unilamellar vesicles and multilamellar vesicles.

According to some embodiments of the invention, the liposomes comprise multilamellar vesicles.

According to some embodiments of the invention, the liposomes comprise small unilamellar vesicles.

According to some embodiments of the invention, the method further comprises modifying the surface so as to obtain a modified surface, wherein the water-soluble polymer and the modified surface are selected such that at least one of the at least one water-soluble polymer is attachable to the modified surface.

According to some embodiments of the invention, the surface is a physiological surface, and the carrier is a physiologically acceptable carrier.

According to some embodiments of the invention, the surface is an articular surface of a synovial joint.

According to some embodiments of the invention, contacting the surface with the solution comprises injecting the solution into a synovial cavity.

According to some embodiments of the invention, the method is for use in the treatment of a synovial joint disorder associated with an increased friction coefficient of an articular surface in the synovial joint.

According to some embodiments of the invention, the solution described herein is for use in the treatment of a synovial joint disorder associated with an increased friction coefficient of an articular surface in the synovial joint.

According to some embodiments of the invention, attaching at least one water-soluble polymer to the surface comprises modifying the surface to obtain a modified surface, wherein the water-soluble polymer is selected to be attachable to the modified surface.

According to some embodiments of the invention, the at least one water-soluble polymer comprises a modified water-soluble polymer which further comprises at least one functional group for covalently attaching the polymer to the surface.

According to some embodiments of the invention, the modified water-soluble polymer comprises at least one functional group for covalently attaching to the surface.

According to some embodiments of the invention, the functional group comprises a dihydroxyphenyl group.

According to some embodiments of the invention, the modified water-soluble polymer is hyaluronic acid conjugated to at least one dopamine moiety via an amide bond.

According to some embodiments of the invention, the surface comprises amine groups.

According to some embodiments of the invention, the at least one water-soluble polymer comprises a non-ionic polymer.

According to some embodiments of the invention, the non-ionic polymer is selected from the group consisting of a polyvinylpyrrolidone and a polyethylene glycol.

According to some embodiments of the invention, the at least one water-soluble polymer comprises an ionic polymer.

According to some embodiments of the invention, the ionic polymer has from 1 to 6 charged groups per 1 kDa.

According to some embodiments of the invention, the ionic polymer is an anionic polymer.

According to some embodiments of the invention, the at least one water-soluble polymer comprises a biopolymer.

According to some embodiments of the invention, the biopolymer is selected from the group consisting of a mucin, a lubricin and a polysaccharide.

According to some embodiments of the invention, the polysaccharide is hyaluronic acid.

According to some embodiments of the invention, a concentration of the hyaluronic acid is in a range of from 0.01 to 10 mg/ml.

According to some embodiments of the invention, a concentration of the hyaluronic acid is less than 1 mg/ml.

According to some embodiments of the invention, the at least one water-soluble polymer is selected to enhance an affinity of the liposomes to the surface.

According to some embodiments of the invention, attaching the hyaluronic acid to the surface comprises contacting the surface with a solution comprising the hyaluronic acid at a concentration in a range of from 0.01 to 10 mg/ml.

According to some embodiments of the invention, the liposomes are characterized by a phase transition melting point (Tm) above 37° C.

According to some embodiments of the invention, attaching at least one water-soluble polymer to the surface is effected by injecting an aqueous solution of the at least one water-soluble polymer into a synovial cavity.

According to some embodiments of the invention, contacting the at least one water-soluble polymer with liposomes is effected by injecting an aqueous solution of the liposomes into a synovial cavity comprising the at least one water-soluble polymer.

According to some embodiments of the invention, at least a portion of the amphiphilic lipid is in a form of a bilayer, the bilayer having a lipophilic region between two hydrophilic regions which comprise charged groups.

According to some embodiments of the invention, the bilayer is bound to the water-soluble polymer by electrostatic attraction.

According to some embodiments of the invention, the synovial joint disorder is selected from the group consisting of arthritis, traumatic joint injury, locked joint, and joint injury associated with surgery.

According to some embodiments of the invention, the arthritis is selected from the group consisting of osteoarthritis, rheumatoid arthritis and psoriatic arthritis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
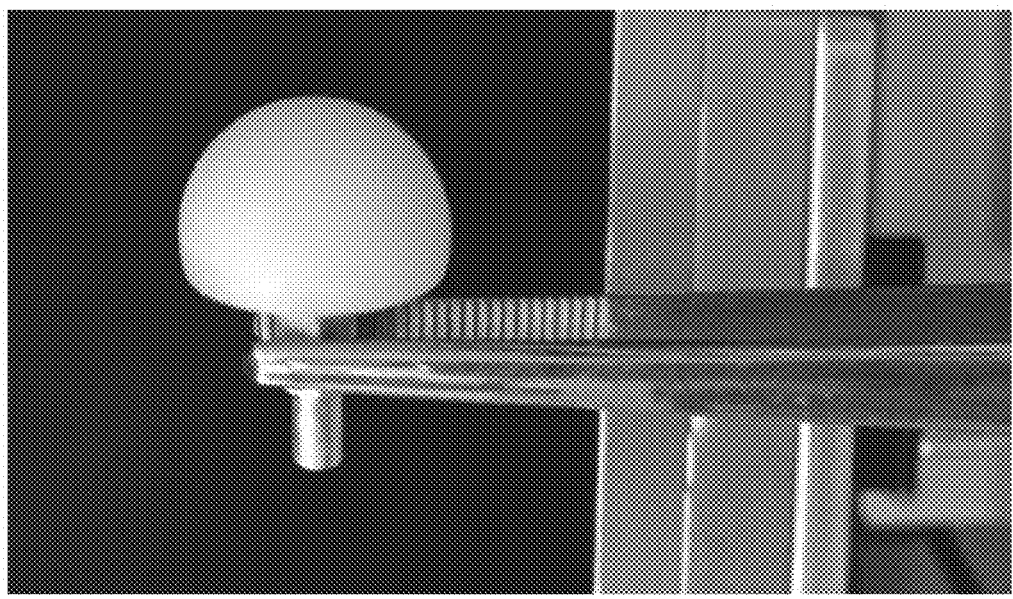
Figure 1B:
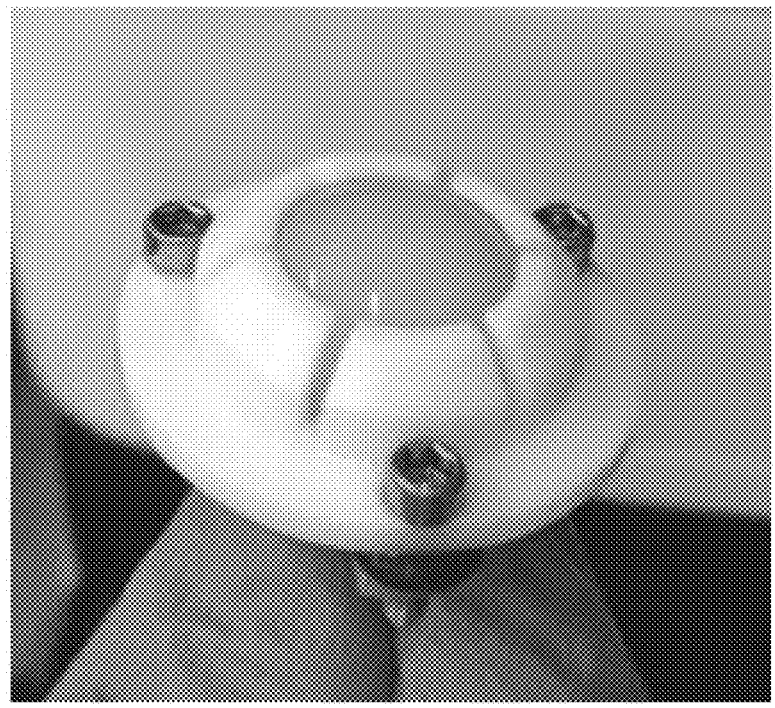

FIGS. 1A-B present photographs of a cornea-mimicking lens holder (FIG. 1A) and the same holder with a soft contact lens mounted in place (FIG. 1B), used in some of the experiments employing a tribometer described in the Examples section hereinunder, in which the soft contact lens has an exemplary hydrogel surface.

Figure 2:
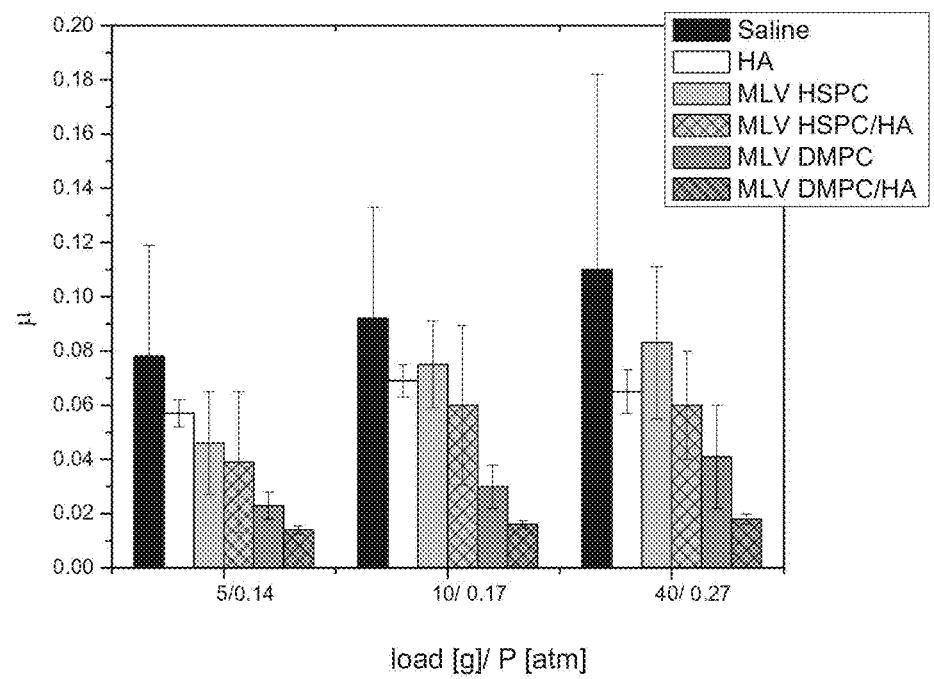

FIG. 2 presents bar graphs showing the friction coefficient of Etafilcon A contact lens upon immersion in saline, HA 1MDa 0.2 mg/ml, MLV HSPC liposomes (45 mM), MLV HSPC liposomes+HA, MLV DMPC (45 mM), or MLV DMPC+HA, followed by rinsing with saline, as measured at a load of 5, 10 and 40 grams (corresponding respectively to mean pressures of 0.14, 0.17 and 0.27 atmospheres).

Figure 3:
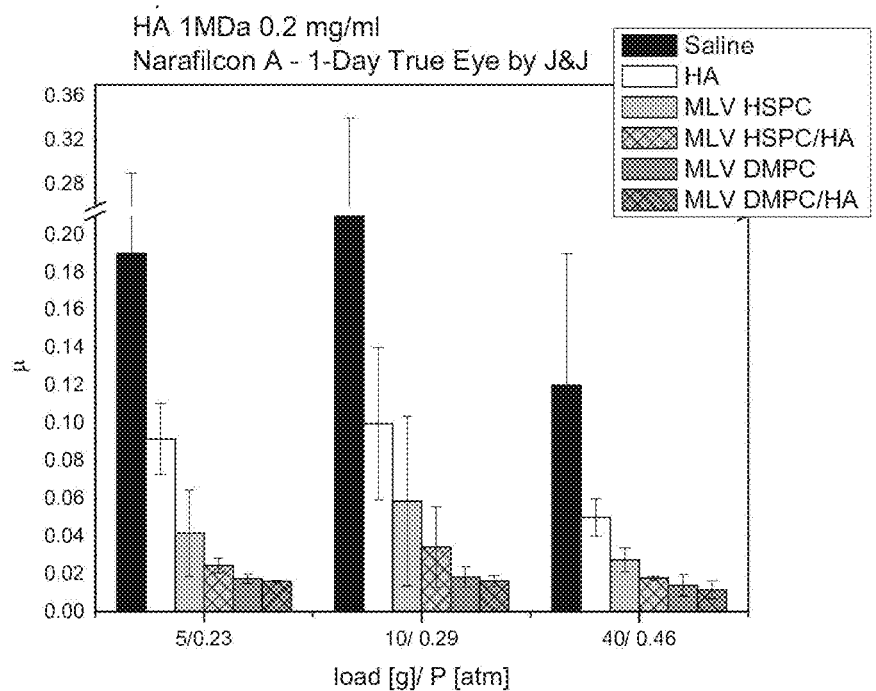

FIG. 3 presents bar graphs showing the friction coefficient of Narafilcon A contact lens upon immersion in saline, HA 1MDa 0.2 mg/ml, MLV HSPC liposomes (45 mM), MLV HSPC liposomes+HA, MLV DMPC (45 mM), or MLV DMPC+HA, followed by rinsing with saline, as measured at a load of 5, 10 and 40 grams (corresponding respectively to mean pressures of 0.23, 0.29 and 0.46 atmosphere).

Figure 4:
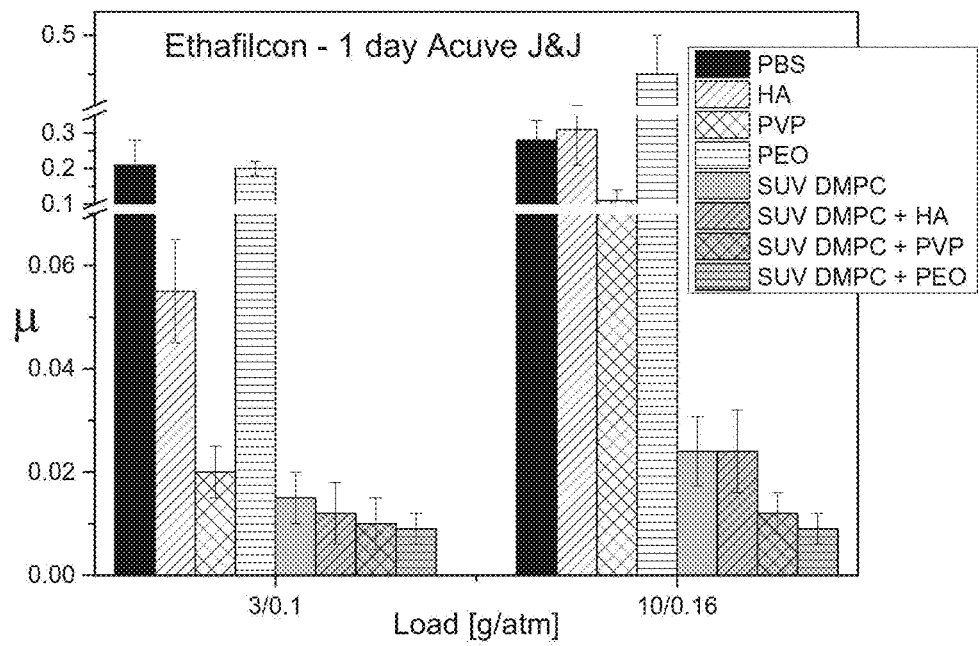

FIG. 4 presents bar graphs showing the friction coefficient of Etafilcon A contact lens upon immersion in PBS, solutions of HA, PVP or PEO (0.2 mg/ml), a solution of SUV DMPC liposomes (10 mM), or solutions of SUV DMPC liposomes with HA, PVP or PEO, followed by rinsing with PBS, as measured at a load of 3 and 10 grams (corresponding respectively to mean pressures of 0.1 and 0.16 atmospheres).

Figure 5:
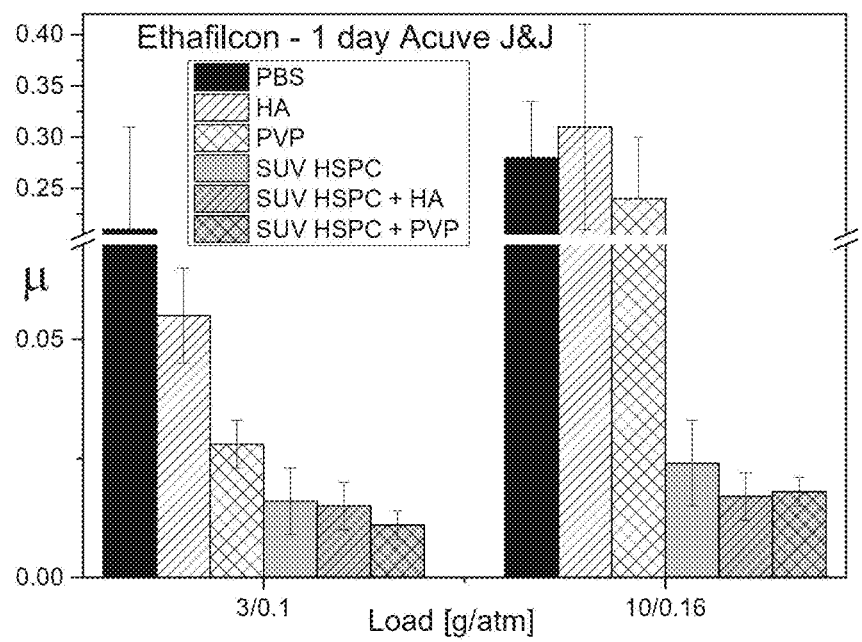

FIG. 5 presents bar graphs showing the friction coefficient of Etafilcon A contact lens upon immersion in PBS, solutions of HA or PVP (0.2 mg/ml), a solution of SUV HSPC liposomes (10 mM), or solutions of SUV HSPC liposomes with HA or PVP, followed by rinsing with PBS, as measured at a load of 3 and 10 grams (corresponding respectively to mean pressures of 0.1 and 0.16 atmospheres).

Figure 6:
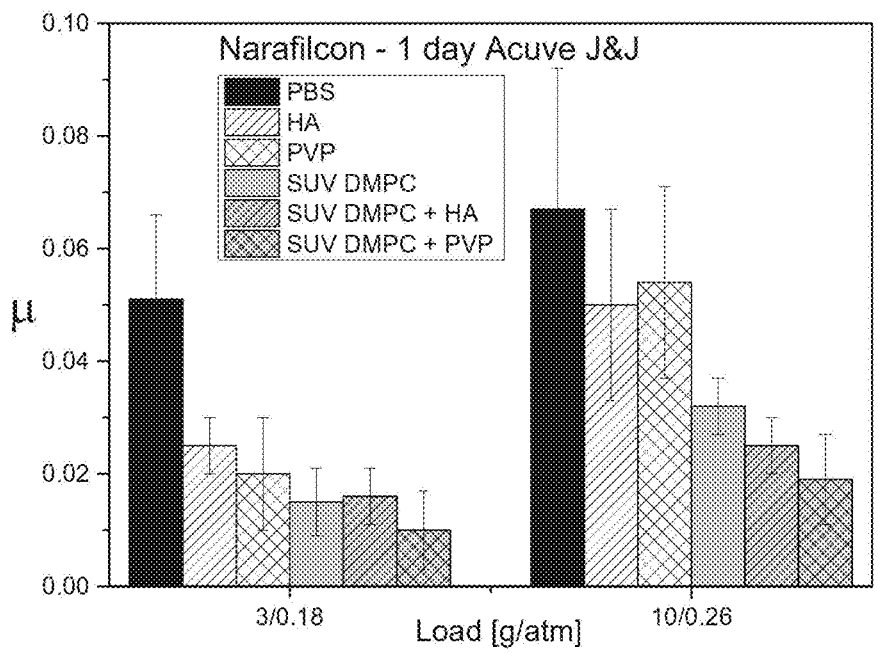

FIG. 6 presents bar graphs showing the friction coefficient of Narafilcon A contact lens upon immersion in PBS, solutions of HA or PVP (0.2 mg/ml), a solution of SUV DMPC liposomes (10 mM), or solutions of SUV DMPC liposomes with HA or PVP, followed by rinsing with PBS, as measured at a load of 3 and 10 grams (corresponding respectively to mean pressures of 0.18 and 0.26 atmospheres).

Figure 7:
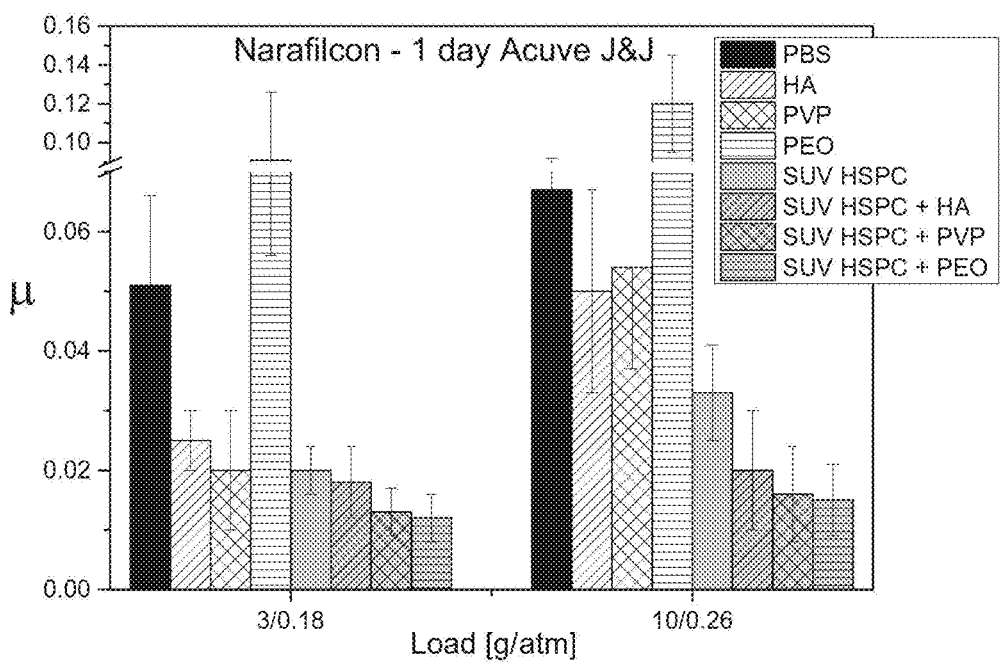

FIG. 7 presents bar graphs showing the friction coefficient of Narafilcon A contact lens upon immersion in PBS, solutions of HA, PVP or PEO (0.2 mg/ml), a solution of SUV HSPC liposomes (10 mM), or solutions of SUV HSPC liposomes with HA, PVP or PEO, followed by rinsing with PBS, as measured at a load of 3 and 10 grams (corresponding respectively to mean pressures of 0.18 and 0.26 atmospheres).

Figure 8:
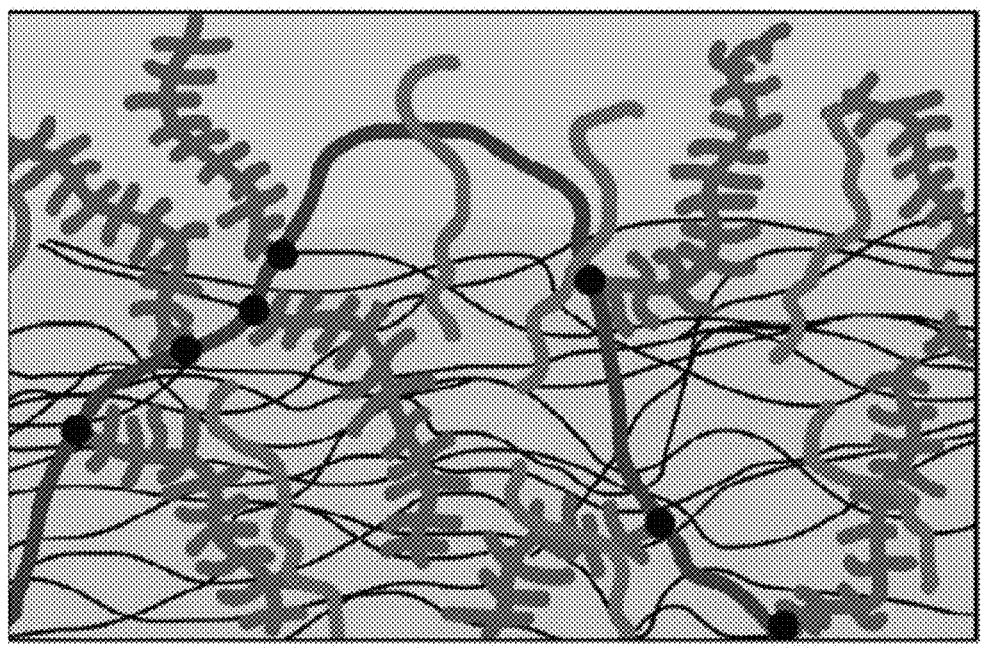

FIG. 8 (Background art) presents a schematic illustration of the main macromolecules at the outer cartilage surface: hyaluronan (darker, thick curves, blue online), bottle-brush-like aggrecans (red online) and lubricins (lighter, thick curves, green online), adapted from Klein, J. (2009) *Science* 323, 47-48.

FIGS. 9A-C present AFM micrograph under water of a mica surface bearing DPPC liposomes that have been mixed with HA for 48 hours at T higher than Tm (FIG. 9A), compared to AFM micrograph of a mica surface bearing DPPC liposomes that have been mixed for 48 hours at T higher than Tm without HA (inset (i)), and a Background art cryo-SEM image of a mica surface bearing DPPC liposomes, adapted from Sorkin et al. [*Biomaterials* 2013, 34:5465-5475] (inset (ii)); AFM micrograph of a mica surface bearing avidin-bHA-DPPC layers (FIG. 9B), with an inset showing an intact liposome on the same scale for comparison; and a schematic illustration of HA-DPPC complexes formed on top of the avidin layer on a surface (FIG. 9C), drawn based on the AFM micrograph of FIG. 9B.

Figure 10A:
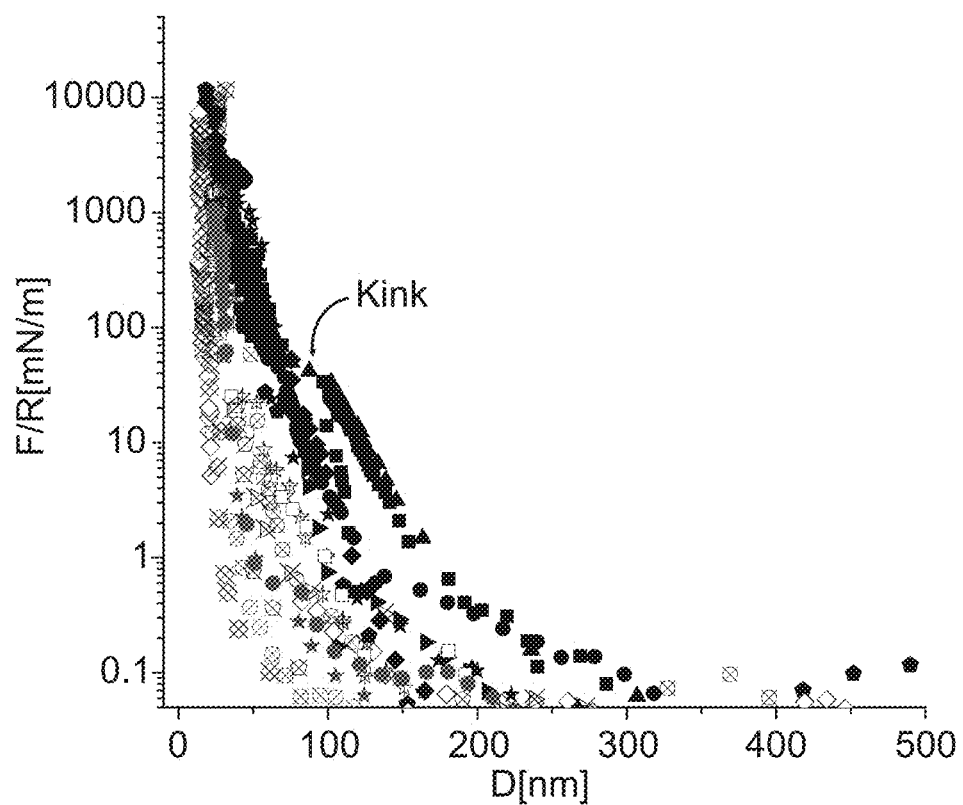
Figure 10B:
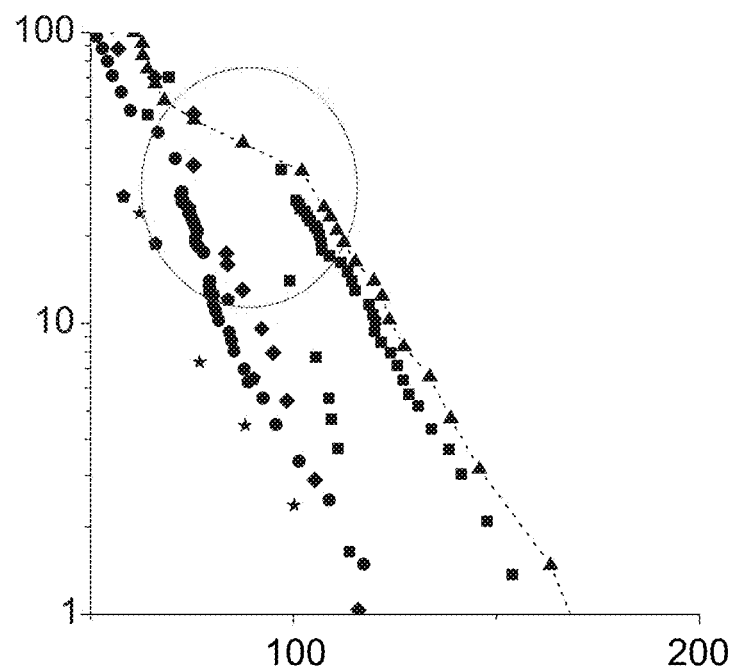
Figure 10C:
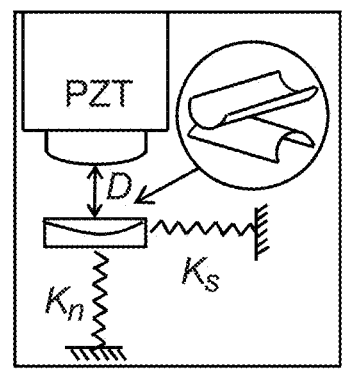

FIGS. 10A-C present comparative plots showing normal interaction as a function of surface separation D between two avidin-bHA-DPPC-bearing surfaces, measured using a surface force balance (SFB), with full symbols denoting first approaches, crossed symbols denoting second or third approaches and empty symbols denoting receding profiles, and with the black symbols ring to measurements in pure water, and red symbols referring to measurements in 0.15 M $KNO_3$ salt solution (FIG. 10A); and a close-up of first approaches profiles that present a rapid decrease in the surface separation (a kink circled in red in FIG. 10B), at D around 100 nm, with the dashed line added as a guide to the eye; and a schematic illustration of the surface force balance (SFB) technique (FIG. 10C), with Kn and Ks being the normal and shear springs respectively, and D being the surface separation.

Figure 11A:
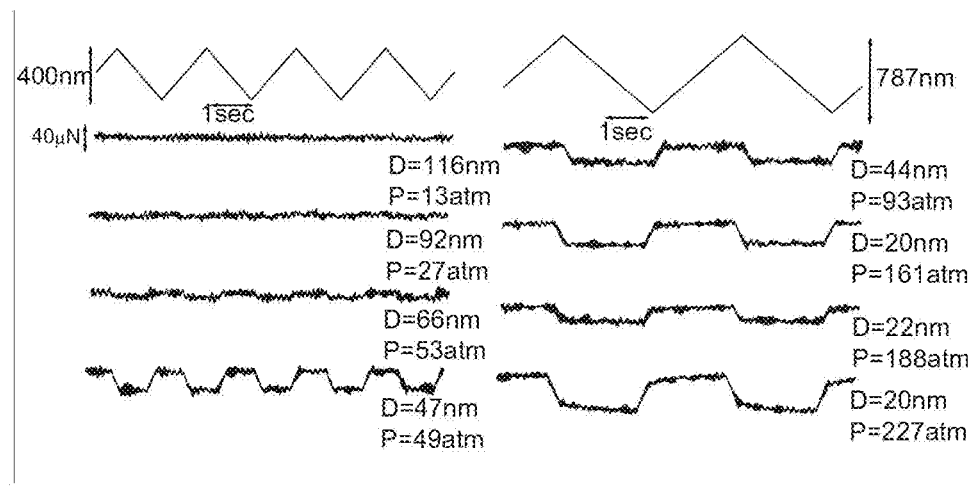
Figure 11B:
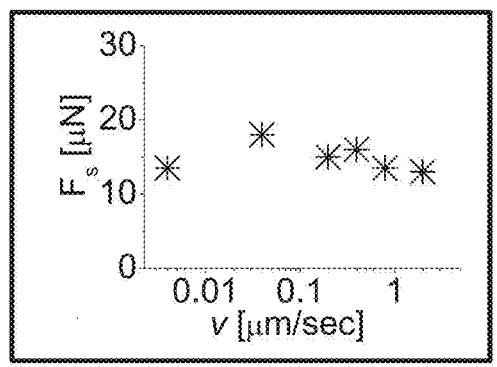
Figure 11C:
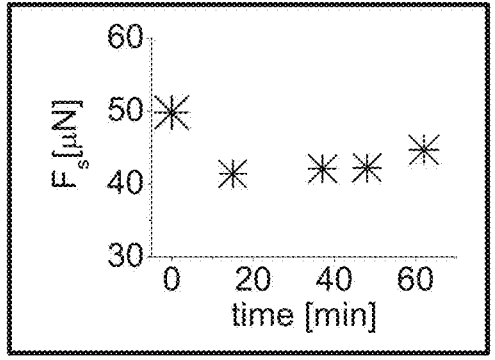

FIGS. 11A-C present graphs showing shear force (Fs) vs. time traces, taken directly from SFB measurements, when two avidin-bHA-DPPC bearing surfaces slide past against each other in pure water (FIG. 11A), with the two top traces representing two different amplitudes of back and forth shear motion applied to the upper mica surface, and all the other traces are the shear responses transmitted to the lateral springs at different surface separations and different pressures; a graph showing shear force as a function of shear velocity at pressure P=161 Atm, as measured using a surface force balance (SFB), for the two avidin-bHA-DPPC bearing surfaces slide past against each other in pure water (FIG. 11B), and a graph showing shear force as a function of sliding time for a given pressure P=61 Atm and shear velocity $v_s$ of about 0.4 µm/sec, as measured from the USB for the two avidin-bHA-DPPC bearing surfaces slide past against each other in pure water (FIG. 11C).

Figure 12:
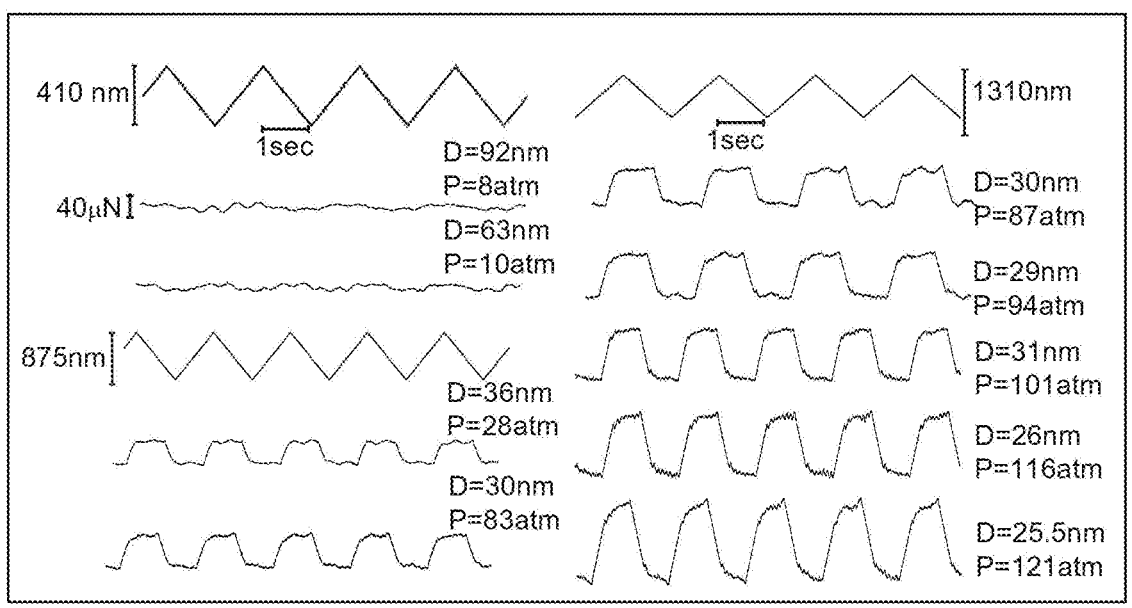

FIG. 12 presents shear force (Fs) vs. time traces, taken directly from SFB measurements, when two avidin+bHA+DPPC bearing surfaces slide past against each other in 0.15M $KNO_3$ salt solution, with the three traces having a zigzag pattern representing three different amplitudes of shear motion applied to the upper mica surface, and the traces below each of the aforementioned three traces representing the corresponding shear responses transmitted to the lateral springs at different surface separations and different pressures.

Figure 13A:
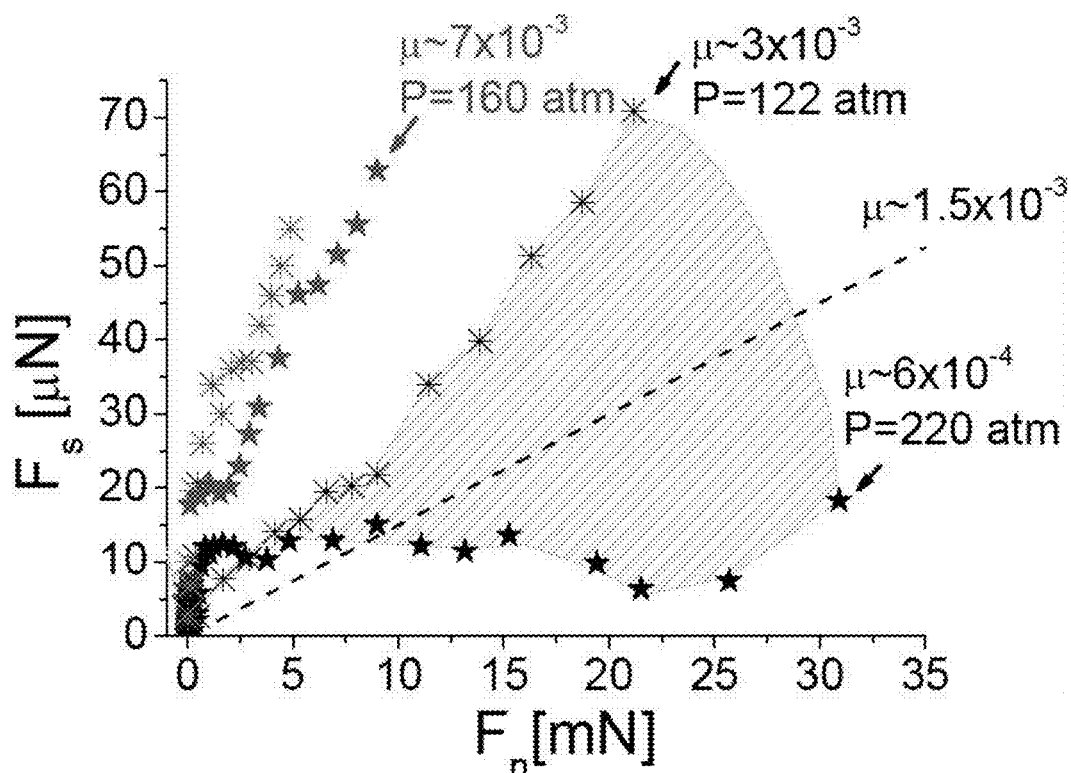
Figure 13B:
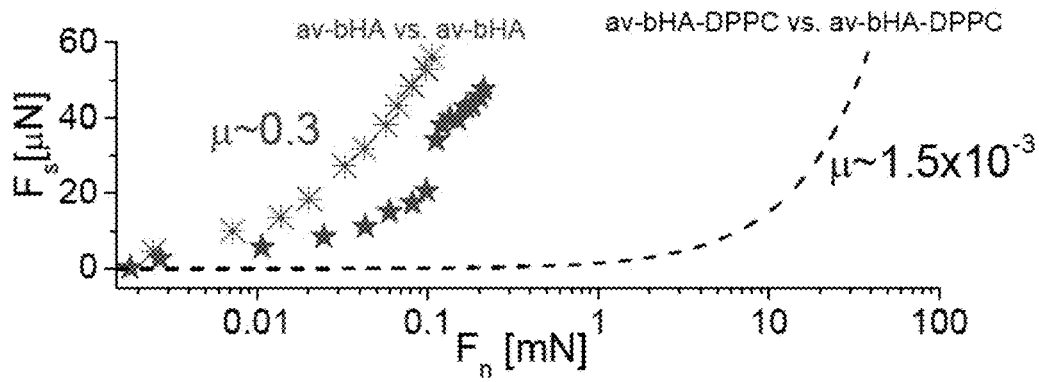

FIGS. 13A-B present graphs showing shear forces (Fs) as a function of normal forces (Fn), when two avidin-bHA-DPPC bearing surfaces slide past each other, across water (black symbols) and across 0.15 M $KNO_3$ salt solution (red symbols), with the shaded area including all the Fs vs. Fn profiles for the avidin-bHA-DPPC-bearing surfaces interacting across water, and the two Fs vs. Fn profiles refer to the measurements having the maximum and the minimum value of effective friction coefficient µ at high pressure across water (FIG. 13A), and comparative graphs showing shear forces (Fs) as a function of normal forces (Fn), when two avidin-bHA-DPPC (dashed black line) and two avidin-bHA (blue symbols) bearing surfaces slide past against each other, across water (crosses represent data from Seror et al., *Biomacromolecules* 2012, 13: 3823-3832, stars represent data not previously published).

Figures 14A, 14B:
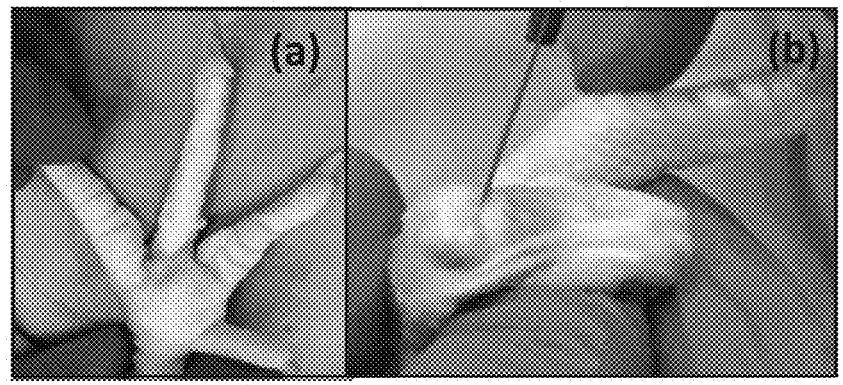
Figure 14C:
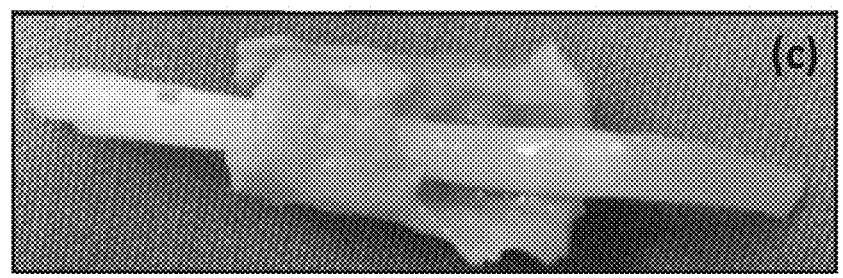
Figures 14D, 14E:
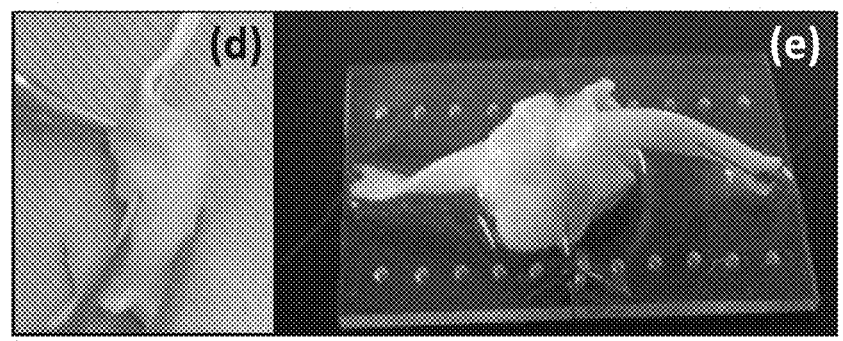

FIGS. 14A-14E present photographs showing extraction of a tendon and associated sheath (FIG. 14B) from a chicken foot (FIG. 14A), the extracted tendon and sheath (FIG. 14C), cutting of the tendon to allow free gliding of the tendon in the sheath (FIG. 14D), and the cut tendon and sheath after placement in a tribometer (FIG. 14E).

Figure 15:
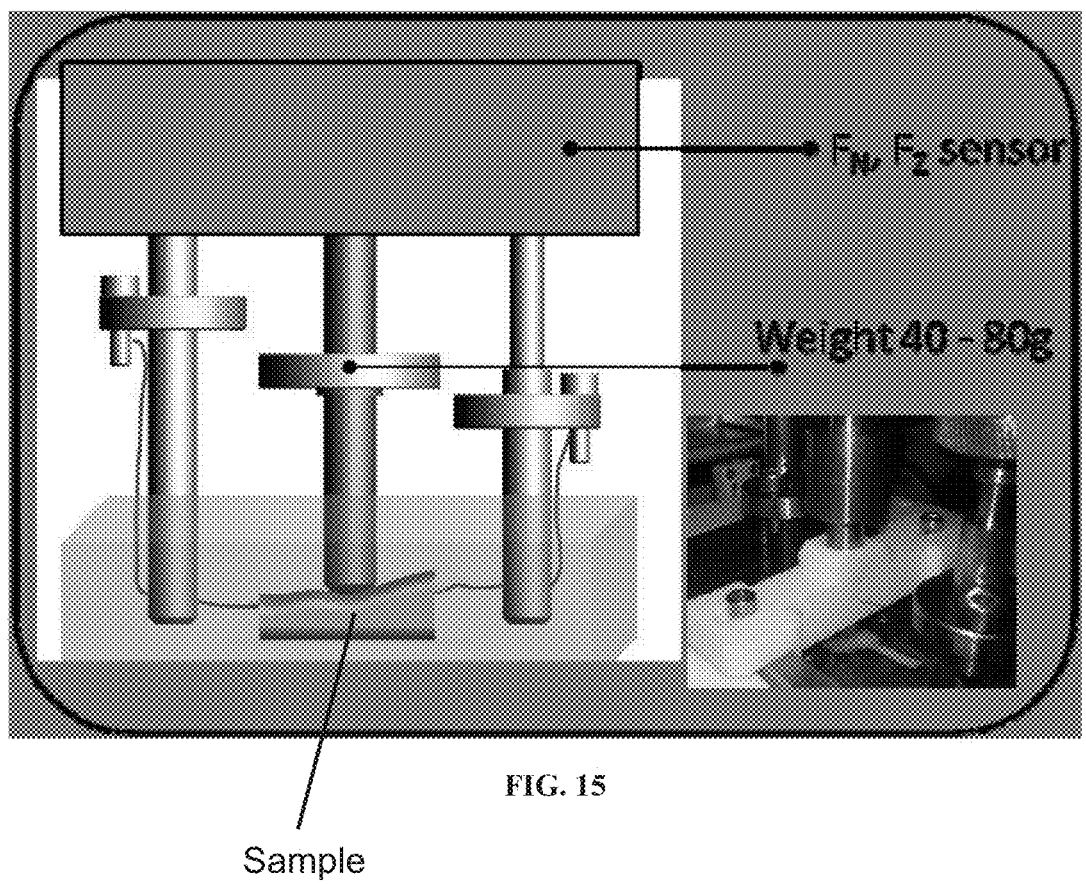

FIG. 15 presents a scheme depicting a tribometer for testing friction within a sample under a load of 40-80 grams, the tribometer including an $F_N$, $F_Z$ force sensor connected to a component within the sample (a photograph showing the depicted tribometer is presented in the right-hand panel.

Figure 16:
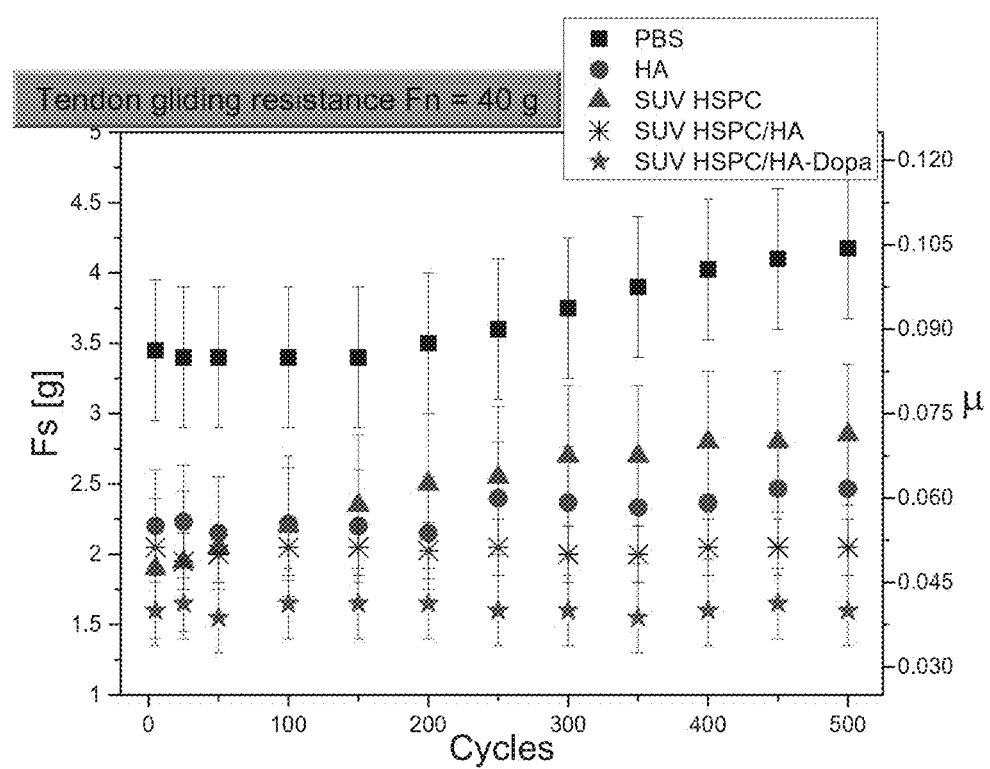

FIG. 16 is a graph showing shear forces (Fs) and friction coefficient µ for a tendon sliding through a sheath, over the course of 500 cycles of sliding under a normal force (Fn) of 40 grams, upon immersion in PBS or in a solution of hyaluronic acid (HA), hydrogenated soy phosphatidylcholine small unilamellar vesicles (SUV HSPC), and hydrogenated soy phosphatidylcholine small unilamellar vesicles in combination with hyaluronic acid (SUV HSPC/HA) or with hyaluronic acid with dopamine functional groups (SUV HSPC/HA-Dopa).

Figure 17:
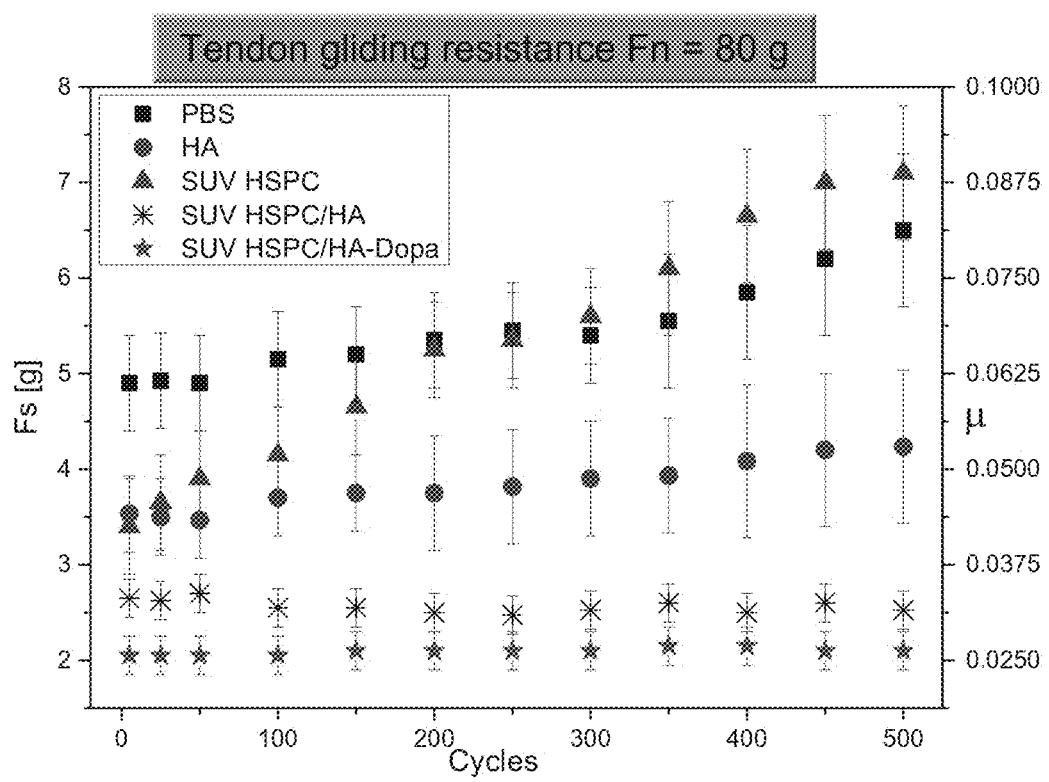

FIG. 17 is a graph showing shear forces (Fs) and friction coefficient µ for a tendon sliding through a sheath, over the course of 500 cycles of sliding under a normal force (Fn) of 80 grams, upon immersion in PBS or in a solution of hyaluronic acid (HA), hydrogenated soy phosphatidylcholine small unilamellar vesicles (SUV HSPC), and hydrogenated soy phosphatidylcholine small unilamellar vesicles in combination with hyaluronic acid (SUV HSPC/HA) or with hyaluronic acid with dopamine functional groups (SUV HSPC/HA-Dopa).

Figure 18:
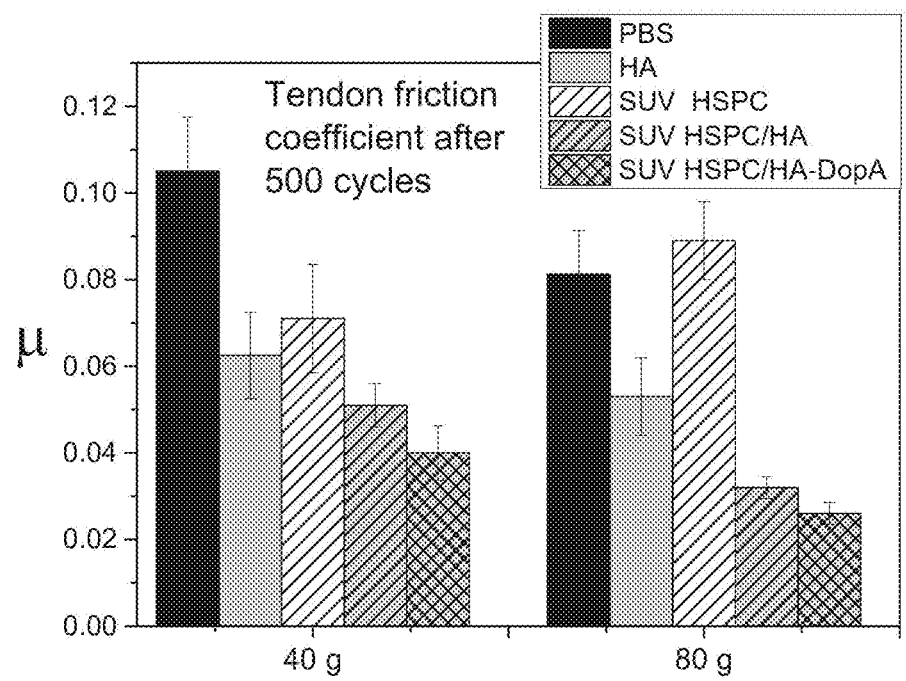

FIG. 18 presents bar graphs showing friction coefficient µ for a tendon sliding through a sheath after 500 cycles of sliding under a normal force (Fn) of 40 or 80 grams, upon immersion in PBS or in a solution of hyaluronic acid (HA), hydrogenated soy phosphatidylcholine small unilamellar vesicles (SUV HSPC), and hydrogenated soy phosphatidylcholine small unilamellar vesicles in combination with hyaluronic acid (SUV HSPC/HA) or with hyaluronic acid with dopamine functional groups (SUV HSPC/HA-Dopa).

Figure 19:
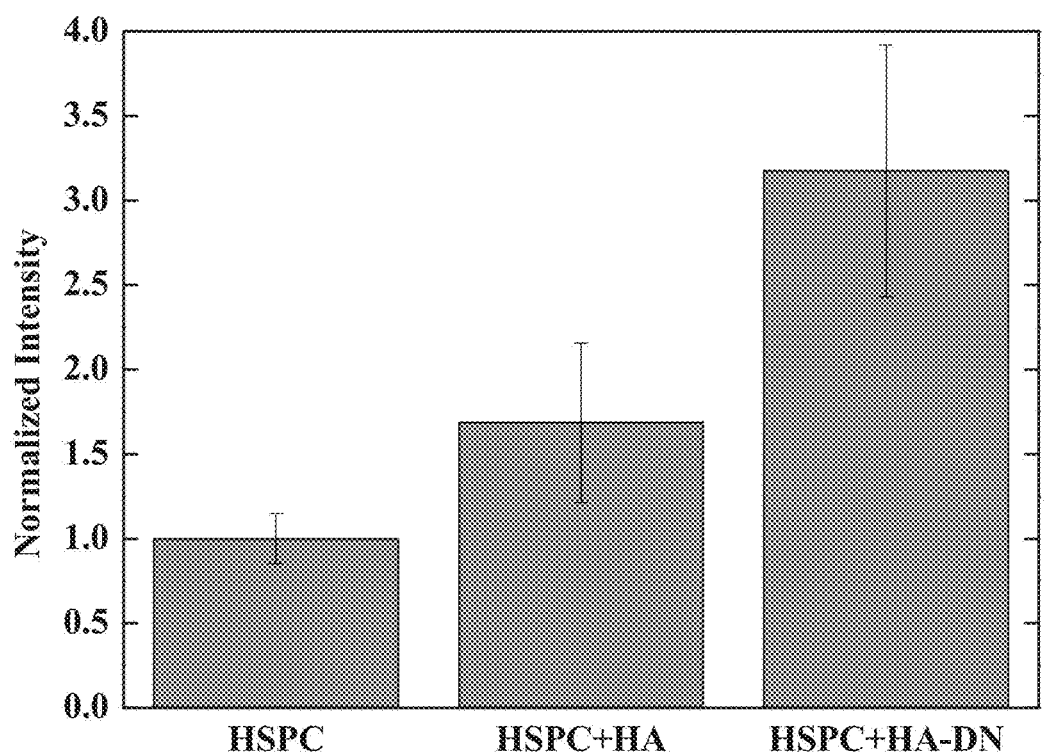

FIG. 19 is a bar graph showing fluorescent intensity of the fluorescent dye DiI on a surface of a tendon following immersion in a solution of DiI-labeled hydrogenated soy phosphatidylcholine (HSPC) liposomes or in a solution of DiI-labeled HSPC liposomes in combination with hyaluronic acid (HSPC+HA) or with hyaluronic acid with dopamine functional groups (HSPC+HA-DN).

Figures 20A, 20B, 20C:
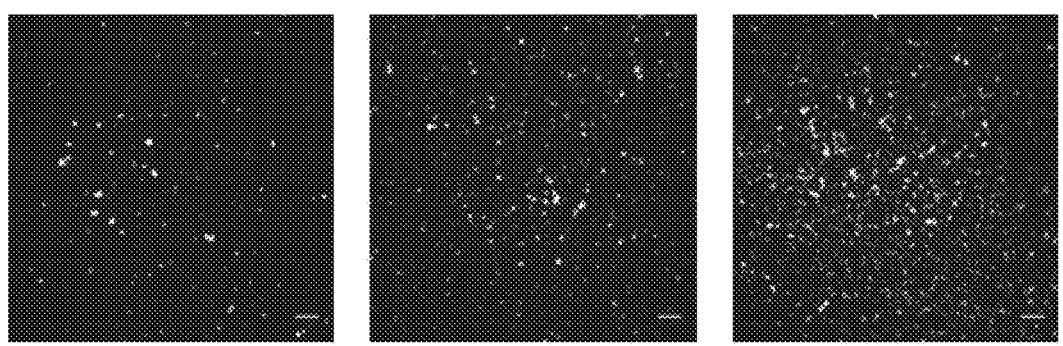

FIGS. 20A-20C present fluorescent images showing the fluorescent dye DiI on a surface of a tendon following immersion in a solution of DiI-labeled hydrogenated soy phosphatidylcholine (FIG. 20A) liposomes or in a solution of DiI-labeled HSPC liposomes in combination with hyaluronic acid (FIG. 20B) or with hyaluronic acid with dopamine functional groups (FIG. 20C).

Figure 21:
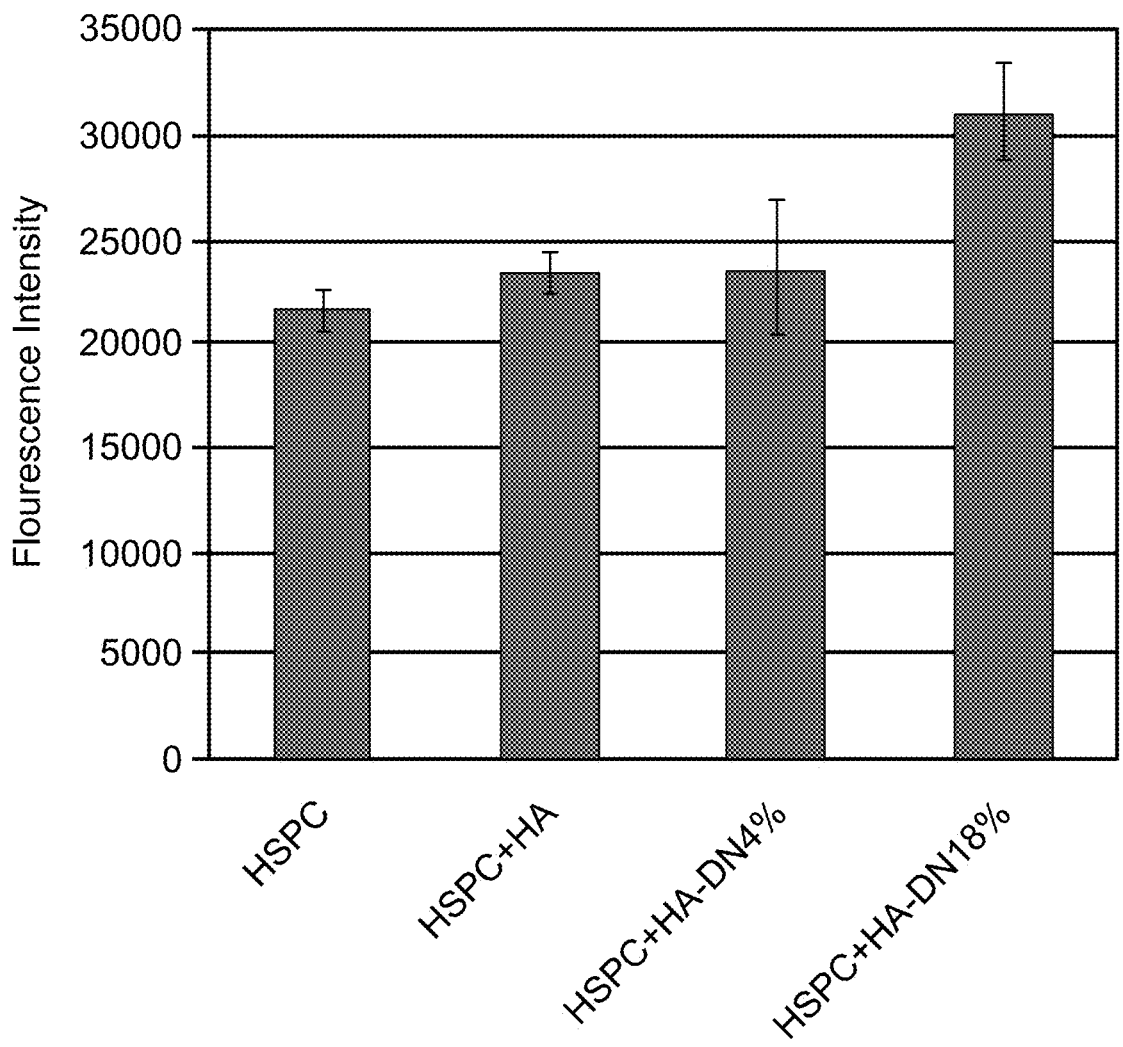

FIG. 21 is a bar graph showing fluorescent intensity of the fluorescent dye DiI for a gelatin-methacrylate hydrogel following immersion in a solution of DiI-labeled hydrogenated soy phosphatidylcholine (HSPC) liposomes or in a solution of DiI-labeled HSPC liposomes in combination with hyaluronic acid (HSPC+HA) or with hyaluronic acid with dopamine functional groups at a concentration of 4% (HSPC+HA-DN4%) or 18% (HSPC+HA-DN18%) dopamine per hyaluronic acid repeating (disaccharide) unit.

DESCRIPTION OF SPECIFIC EMBODIMENTS OF THE INVENTION

The present invention, in some embodiments thereof, relates to material science and, more particularly, but not exclusively, to methods and/or compositions for reducing a friction coefficient of a surface of animate or inanimate objects.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for an improved methodology for lubricating interfaces with a surfaces, including interfaces with physiological surfaces, the present inventors have studied the effect of a solution containing liposomes, particularly phosphatidylcholine (PC)-containing liposomes, which are known to be biocompatible, in combination with water-soluble polymers such as hyaluronic acid, polyvinylpyrrolidone and polyethylene oxide, while using different types of hydrogel surfaces, and have surprisingly uncovered that this combination considerably exceeds the lubrication effect observed in the presence of liposomes alone or water-soluble polymer alone, resulting in a synergistic effect in reducing the friction coefficient of the treated surface. The lubrication effect is mediated by boundary lubrication, that is, it does not require the presence of the solution between surfaces in order to reduce friction between the surfaces. Rather, contact with the solution results in a treated surface, wherein the surface per se is characterized by enhanced lubricity.

Referring now to the drawings, FIGS. 2 and 3 show that exposure of contact lenses composed of the exemplary hydrogels etafilcon A (FIG. 2) and narafilcon A (FIG. 3) to liposomes and hyaluronic acid (HA) enhances the lubricity of the hydrogel more effectively than does exposure to liposomes alone or HA alone (as determined using the cornea model shown in FIGS. 1A-1B). FIGS. 4-7 show that exposure of etafilcon A (FIGS. 4 and 5) and narafilcon A (FIGS. 6 and 7) hydrogels to liposomes (small unilamellar vesicles) and hyaluronic acid (HA), polyvinylpyrrolidone (PVP) or polyethylene oxide (PEO) enhances the lubricity of the hydrogel surfaces more effectively than does exposure to liposomes alone or HA, PVP or PEO, and that PVP and PEO are typically at least as effective as HA at enhancing lubricity in combination with liposomes. FIGS. 4 and 7 show that PEO exhibits particularly strong synergy with liposomes at enhancing lubricity, whereas PEO alone does not enhance lubricity at all and may even reduce lubricity.

This result surprisingly indicates that a hydrogel surface contacted with water-soluble polymer (such as HA, PVP or PEO) and liposomes is not a mosaic of a surface coated by water-soluble polymer per se and a surface coated by liposomes per se (which would result in a lubricity which is intermediate between the lubricity obtained with water-soluble polymer alone and with liposomes alone), but rather, a surface coated with water-soluble polymer and liposomes exhibits a physical characteristic which is not present in surfaces coated by water-soluble polymer alone or liposomes alone, indicating synergy between the water-soluble polymer and liposomes.

FIGS. 2-7 further show that at relatively low pressures dimyristoyl phosphatidylcholine liposomes (which are in a liquid phase) are more effective at reducing the lubricity than are hydrogenated soy phosphatidylcholine liposomes (which are in a solid phase), whereas at higher pressures, hydrogenated soy phosphatidylcholine liposomes are more effective.

The present inventors have further studied the effect of phospholipids complexed with a water-soluble polymer such as hyaluronic acid which is attached to surfaces, and have uncovered that such phospholipid-water-soluble polymer complexes form boundary layers which exhibit an exceptional combination of lubricity and robustness, which is not exhibited by the water-soluble polymer(s) when used per se. The present inventors have envisioned that such lubricious boundary layers may be formed on a wide variety of surfaces, including surfaces which do not exhibit affinity to phospholipids per se.

FIGS. 9B and 9C show a surface coated with phosphatidylcholine following attachment of hyaluronic acid to the surface (by attaching biotinylated hyaluronic acid to an avidin-coated surface). FIG. 9A shows intact phosphatidylcholine liposomes on a surface, following mixture of the liposomes with hyaluronic acid in solution, but in the absence of hyaluronic acid attached to the surface.

FIGS. 10A-13B show force measurements between two of the abovementioned surfaces coated with biotinylated hyaluronic acid and phosphatidylcholine. FIGS. 10A-10B show that the surfaces are separated by about 22 nm, suggesting that each surface is coated by a layer of approximately 11 nm—which corresponds to the combined thickness of avidin, hyaluronic acid and a phosphatidylcholine bilayer—and that the coated surfaces are in direct contact with each other. FIG. 11B shows that the friction has little dependence on sliding velocity, which indicates a boundary lubrication mechanism. FIGS. 13A-13B show that the friction coefficient of such surfaces is at an order of magnitude of only $10^{-3}$, even at pressures as high as 220 atmospheres. FIG. 11C shows that friction between the surfaces remains low during the course of 1 hour of continuous shear force application at high pressure, indicating considerable robustness.

FIGS. 16-18 show that hyaluronic acid in combination with liposomes (e.g., small unilamellar vesicles) is effective for reducing friction associated with movement of a tendon in manner which is highly robust to repeated cycles of tendon motion, and that functionalization of the hyaluronic acid with dihydroxyphenyl groups (by coupling with dopamine) is even more effective in this respect. FIGS. 19-20C show that functionalization of the hyaluronic acid with dihydroxyphenyl groups enhances binding of lipids to the tendon surface, suggesting that the reduction of friction corresponds to the degree of lipid binding to the tendon surface which is mediated by the water-soluble polymer (e.g., unmodified and functionalized hyaluronic acid). FIG. 21 shows that functionalization of the hyaluronic acid with dihydroxyphenyl groups also enhances binding of lipids to gelatin methacrylate hydrogel.

These results indicate that treatment of a surface by a combination of liposomes and attachment of water-soluble polymers (such as HA) results in exceptional and robust lubricity. The lubricity does not require any direct interaction between the liposomes and surface, and does not require the water-soluble polymer(s) per se to exhibit a lubricating effect.

Without being bound by any particular theory, it is believed that the amphiphilic lipids supplied by the liposomes provide a very low friction coefficient as a result of hydration lubrication associated with hydration of the hydrophilic moieties of the lipids. It is further believed that attachment of water-soluble polymer(s) to a surface enhances lubricity by facilitating adherence of the lubricating lipids to the surface (e.g., anchoring the lipids to the surface), particularly to a surface which does not normally exhibit affinity to such lipids, thereby enhancing the robustness of the lubricating lipid film, and allowing for enhanced lubricity even under high pressures.

Without being bound by any particular theory, it is further believed that attachment of the water-soluble polymer(s) to a surface may result in a smoother surface (e.g., by covering asperities with flexible polymer chains thereby further enhancing lubricity.

The exemplified boundary lubrication, which uses molecules native to synovial joints (e.g., HA and PC lipids) appears to mimic the highly effective lubrication in healthy synovial joints, which has hitherto been unobtainable by prior lubrication techniques in models of synovial joints. These effects are particularly desirable in the context of treating synovial joint disorders associated with increased friction of an articular surface in the afflicted joint, such as arthritis.

Based on the results presented herein, lubrication of a wide variety of surfaces besides hydrogels and articular surfaces may be effected, in accordance with various embodiments of the invention described herein.

Reducing Friction:

As exemplified herein, liposomes and a water-soluble polymer may be used in combination to reduce a friction coefficient of a variety of surfaces.

According to an aspect of some embodiments of the invention, there is provided a method of reducing a friction coefficient of a surface, the method utilizing at least one water-soluble polymer (as defined herein) and liposomes (as defined herein).

Any one of the embodiments described herein of any of the aspects described herein relating to reducing a friction coefficient of a surface may utilize liposomes in accordance with any one of the embodiments described herein with respect to liposomes and/or lipids (e.g., in the section herein relating to liposomes and lipids), as well as at least one water-soluble polymer in accordance with any one of the embodiments described herein with respect to water-soluble polymers (e.g., in the section herein relating to water-soluble polymers).

In some embodiments, the method comprises attaching the water-soluble polymer(s) to the surface, and contacting the water-soluble polymer(s) with liposomes, thereby effecting coating of the surface by amphiphilic lipids of the liposomes.

In some embodiments, the water-soluble polymer(s) forms a layer which adheres to the surface as well as to the lipids, thereby mediating adherence of the lipids to the surface.

In some embodiments, the water-soluble polymer(s) forms a layer which adheres to the surface at one side of a water-soluble polymer layer and adheres to the lipids at the other side of the water-soluble polymer layer, thereby mediating adherence of the lipids to the surface.

In some embodiments, attaching at least one water-soluble polymer to the surface is effected prior to contacting the water-soluble polymer(s) with liposomes.

In some embodiments, attaching at least one water-soluble polymer to the surface is effected concomitantly and/or subsequent to contacting the water-soluble polymer(s) with liposomes. In some embodiments, the surface is contacted with a mixture of the water-soluble polymer(s) and liposomes (e.g., a solution described herein).

Optionally, at least a portion of lipids adhere to the water-soluble polymer(s) prior to attachment of the water-soluble polymer(s) to the surface. For example, attachment of the water-soluble polymer(s) to the surface may optionally be effected by a chemical process which is less rapid than adherence of lipids to the water-soluble polymer(s).

Alternatively or additionally, at least a portion of the water-soluble polymer(s) is attached to the surface prior to adherence of lipids to the water-soluble polymer(s). For example, attachment of the water-soluble polymer(s) to the surface may optionally be effected by a chemical process which is more rapid than adherence of lipids to the water-soluble polymer(s).

In some embodiments, the method comprises contacting the surface with a liquid formulation comprising at least one water-soluble polymer(s) (e.g., as described herein in any one of the respective embodiments), liposomes (e.g., as described herein in any one of the respective embodiments) and an aqueous carrier (e.g., as described herein in any one of the respective embodiments). The water-soluble polymer(s) and the surface are preferably selected such that the water-soluble polymer(s) is attachable to the surface.

Herein throughout, liquid formulations are referred to interchangeably as "solution". It is to be noted that the term "solution" encompasses herein throughout any liquid formulation in which the ingredients, e.g., the water-soluble polymer(s) and/or the liposomes/lipids, are included within a liquid carrier, whereby each of the ingredients can be dissolved or dispersed within the carrier. The term "solution" as used herein therefore encompasses also "dispersion", including liquid formulations wherein some ingredients are dissolved and some ingredients (e.g., liposomes) are dispersed. The term "liquid formulation" as used herein encompasses both a solution and a dispersion.

In some embodiments, attaching the water-soluble polymer(s) to the surface comprises contacting the surface with a solution comprising a water-soluble polymer at a concentration in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the water-soluble polymer(s) in the solution comprises an ionic polymer (e.g., as described herein in any one of the respective embodiments) at a concentration described hereinabove, liposomes (e.g., as described herein in any one of the respective embodiments) and an aqueous carrier (e.g., as described herein in any one of the respective embodiments).

In some embodiments, attaching more than one water-soluble polymer to the surface comprises contacting the surface with a solution comprising each water-soluble polymer at a concentration in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the water-soluble polymers in the solution comprise at least one ionic polymer (e.g., as described herein in any one of the respective embodiments) at a concentration described hereinabove, liposomes (e.g., as described herein in any one of the respective embodiments) and an aqueous carrier (e.g., as described herein in any one of the respective embodiments).

In some embodiments, the water-soluble polymer(s) comprises a polysaccharide (e.g., as described herein in any one of the respective embodiments), optionally an ionic polysaccharide, and attaching the polysaccharide to the surface comprises contacting the surface with a solution comprising the polysaccharide at a concentration in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the solution is a solution comprising a polysaccharide (e.g., as described herein in any one of the respective embodiments), liposomes (e.g., as described herein in any one of the respective embodiments) and an aqueous carrier (e.g., as described herein in any one of the respective embodiments).

In some embodiments, the water-soluble polymer(s) comprises hyaluronic acid, polyvinylpyrrolidone (PVP) and/or polyethylene oxide (PEO) and attaching the hyaluronic acid, PVP and/or PEO to the surface comprises contacting the surface with a solution comprising the hyaluronic acid, PVP and/or PEO at a concentration in a range of from 0.01 to 10 mg/ml. In some embodiments, the hyaluronic acid, PVP and/or PEO concentration is in a range of from 0.03 to 10 mg/ml. In some embodiments, the hyaluronic acid, PVP and/or PEO concentration is in a range of from 0.1 to 10 mg/ml. In some embodiments, the hyaluronic acid, PVP and/or PEO concentration is in a range of from 0.3 to 10 mg/ml. In some embodiments, the solution is a solution comprising hyaluronic acid, PVP and/or PEO (e.g., as described herein), liposomes (e.g., as described herein in any one of the respective embodiments) and an aqueous carrier (e.g., as described herein in any one of the respective embodiments).

According to another aspect of embodiments of the invention, there is provided a solution for reducing a friction coefficient of a surface according to a method described herein, the solution comprising at least one water-soluble polymer (e.g., as described herein in any one of the respective embodiments), liposomes (e.g., as described herein in any one of the respective embodiments) and an aqueous carrier (e.g., as described herein in any one of the respective embodiments).

In any of the embodiments described herein, the surface may comprise any type of material or combination of different types of material, including inorganic material and/or organic material, in crystalline, amorphous and/or gel (e.g., hydrogel) forms, for example, metal, mineral, ceramic, glass, polymer (e.g., synthetic polymer, biopolymer), plant and/or animal biomass, and combinations thereof.

Liposomes and Lipids:

The liposomes and/or lipids according to any one of the embodiments described in this section may be used in the context of any one of the embodiments of any of the aspects of the inventions described herein.

As used herein and in the art, the term "liposome" refers to an artificially prepared vesicle comprising a bilayer composed of molecules of an amphiphilic lipid. In an aqueous medium, the bilayer is typically configured such that hydrophilic moieties of the amphiphilic lipid are exposed to the medium at both surfaces of the bilayer, whereas lipophilic moieties of the lipid are located in the internal portion of the bilayer, and therefore less exposed to the medium. Examples of liposomes which may be used in any one of the embodiments described herein include, without limitation, small unilamellar vesicles, large unilamellar vesicles and multilamellar vesicles.

In some embodiments of any one of the embodiments described herein, the liposomes comprise multilamellar vesicles. In some embodiments, the liposomes are primarily (more than 50 weight percents) multilamellar vesicles.

In some embodiments of any one of the embodiments described herein, the liposomes comprise small unilamellar vesicles. In some embodiments, the liposomes are primarily (more than 50 weight percents) small unilamellar vesicles.

In some embodiments of any one of the embodiments described herein, the liposomes comprise large unilamellar vesicles. In some embodiments, the liposomes are primarily (more than 50 weight percents) large unilamellar vesicles.

As used herein, the term "unilamellar" refers to liposomes characterized by a single lipid bilayer, whereas the term "multilamellar" refers to liposomes characterized by a multiple lipid bilayers, for example, concentric bilayers.

As used herein, the phrase "small unilamellar vesicle" refers to unilamellar liposomes of less than 100 nm in diameter, whereas the phrase "large unilamellar vesicle" refers to unilamellar liposomes at least 100 nm in diameter.

As used herein, the term "amphiphilic lipid" refers to compounds comprising at least one hydrophilic moiety and at least one lipophilic moiety. Examples of amphiphilic lipids include, without limitation, fatty acids (e.g., at least 6 carbon atoms in length) and derivatives thereof such as phospholipids and glycolipids; sterols (e.g., cholesterol) and steroid acids.

Herein, the term "phospholipid" refers to a compound comprising a substituted or non-substituted phosphate group and at least one alkyl chain (optionally at least two alkyl chains) which is optionally at least 5 carbon atoms in length, optionally at least 7 atoms in length and optionally at least 9 atoms in length. The at least one alkyl chain is optionally a part of an acyl group (e.g., a fatty acid residue) or an alkyl group per se (e.g., a fatty alcohol residue). In some embodiments, the phosphate group and on e or two (optionally two) alkyl chains (e.g., acyl or alkyl) are attached to a glycerol moiety via the oxygen atoms of glycerol.

In some embodiments of any one of the embodiments described herein, the amphiphilic lipids coating a surface and/or substrate described herein (e.g., a physiological surface, and/or a surface whose friction coefficient is being reduced, according to any one of the respective embodiments described herein) are in the form of intact liposomes, optionally essentially the same liposomes (e.g., essentially the same mass and molecular composition) contacted with the water-soluble polymer(s).

In some embodiments of any one of the embodiments described herein, at least a portion of the amphiphilic lipids (optionally substantially all of the lipids) coating the surface are in a form substantially different than the liposomes from which the lipids are derived. In some embodiments, during the coating for the surface, liposomes are converted to open layers (e.g., lipid bilayers and/or lipid monolayers), as opposed to the closed vesicular structure of the liposomes.

Accordingly, any reference herein to coating a surface with liposomes should not be interpreted as meaning that an obtained coated surface comprises liposomes, only that liposomes are utilized by the methodology (e.g., as an ingredient).

As used herein, the term "phospholipid" encompasses lipids having a (phosphorylated) glycerol backbone (e.g., monoacylglyceride and/or diacylglyceride phospholipids), referred to as glycerophospholipids; and lipids having a (phosphorylated) sphingosine backbone, referred to as phosphosphingolipids (e.g., sphingomyelins).

As used herein, the term "glycolipid" encompasses lipids having a (glycosylated) glycerol backbone (e.g., monoacylglyceride and/or diacylglyceride glycolipids), referred to as glyceroglycolipids; and lipids having a (glycosylated) sphingosine backbone, referred to as glycosphingolipids (e.g., cerebrosides, gangliosides).

In some embodiments of any one of the embodiments described herein, the hydrophilic moiety is an ionic moiety.

Herein, the phrase "ionic moiety" refers to a moiety which comprises at least one charged group (as defined herein), and includes anionic moieties (which have a net negative charge), cationic moieties (which have a net positive charge) and zwitterionic moieties (which have an equal number of positive and negative charges, and thus, no net charge).

Without being bound by any particular theory, it is believed that ionic moieties are particularly effective at binding to water molecules, which renders lipid molecules comprising such moieties particularly effective at promoting hydration lubrication, in which the bound water molecules provide lubrication even at high pressures.

In some embodiments of any one of the embodiments described herein, the amphiphilic lipid comprises at least one phospholipid. Phospholipids are typically characterized by the presence of an ionic moiety which includes a negative charge associated with an oxygen atom in a phosphate moiety ($P-O^-$), although additional charges may be present.

In some embodiments of any one of the embodiments described herein, the phospholipid is a glycerophospholipid. In some embodiments, the glycerophospholipid is a diacylglyceride, comprising two fatty acyl groups and one phosphate group attached to a glycerol backbone.

In some embodiments of any one of the embodiments described herein, a concentration of phospholipids in liposomes in a solution described herein is in a range of from 0.5 mM to 500 mM. In some embodiments, the concentration is in a range of from 1.5 mM to 150 mM. In some embodiments, the concentration is in a range of from 5 mM to 50 mM.

In some embodiments of any one of the embodiments described herein, a concentration of phospholipids in liposomes in a solution described herein is in a range of from 0.5 mM to 50 mM. In some embodiments, the concentration is in a range of from 1.5 mM to 50 mM.

In some embodiments of any one of the embodiments described herein, a concentration of phospholipids in liposomes in a solution described herein is in a range of from 5 mM to 500 mM. In some embodiments, the concentration is in a range of from 5 mM to 150 mM.

In some embodiments of any one of the embodiments described herein, the amphiphilic lipid comprises at least one negatively charged atom and at least one positively charged atom. In some embodiments, the amphiphilic lipid is zwitterionic, that is, the one or more negative charges in the molecule are balanced out by an equal number of positive charge(s) in the molecule. In some embodiments, the amphiphilic lipid comprises exactly one negative charge and one positive charge.

In some embodiments of any one of the embodiments described herein, the amphiphilic lipid comprises at least one phospholipid which comprises a phosphoethanolamine group or N-alkyl derivative thereof.

The phrase "phosphoethanolamine group or N-alkyl derivative thereof" refers to a —O—P(=O)(—O$^-$)—OCH$_2$CH$_2$NR'R"R'"$^+$ group (or a salt thereof), wherein R', R" and R'" are each independently hydrogen or alkyl, preferably C$_{1-4}$ alkyl. In some embodiments of any one of the embodiments described herein, the alkyl group(s) attached to the nitrogen atom are each independently methyl or ethyl. In some embodiments, the alkyl(s) is methyl. The term "phosphoethanolamine" refers to a group wherein R', R" and R'" are each hydrogen. The term "phosphocholine" refers to a group wherein R', R" and R'" are each methyl.

Without being bound by any particular theory, it is believed that the distance between the positive and negative charges in a phosphoethanolamine group or N-alkyl derivative thereof is particularly suitable for binding water molecules and/or promoting hydration lubrication.

In some embodiments of any one of the embodiments described herein, a molar percentage of the phospholipid described herein (e.g., in liposomes described herein) which comprises a phosphoethanolamine group or N-alkyl derivative thereof is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the phospholipid consists essentially of at least one phospholipid comprising a phosphoethanolamine group or N-alkyl derivative thereof.

In some embodiments of any one of the embodiments described herein, a molar percentage of the amphiphilic lipid described herein (e.g., in liposomes described herein) which consists of at least one phospholipid which comprises a phosphoethanolamine group or N-alkyl derivative thereof is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the amphiphilic lipid consists essentially of at least one phospholipid which comprises a phosphoethanolamine group or N-alkyl derivative thereof.

In some embodiments of any one of the embodiments described herein, the at least one phospholipid comprises at least one phosphatidylcholine.

Herein and in the art, the term "phosphatidylcholine" refers to a glycerophospholipid comprising a phosphocholine group and two fatty acyl groups attached to a glycerol backbone (i.e., a diacylglyceride).

In some embodiments of any one of the embodiments described herein, the phospholipid described herein (e.g., in liposomes described herein) is characterized by a molar percentage of phosphatidylcholine (the at least one phosphatidylcholine described herein) which is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the phospholipid consists essentially of at least one phosphatidylcholine.

In some embodiments of any one of the embodiments described herein, the amphiphilic lipid described herein (e.g., in liposomes described herein) is characterized by a molar percentage of phosphatidylcholine (the at least one phosphatidylcholine described herein) which is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the amphiphilic lipid consists essentially of at least one phosphatidylcholine.

The fatty acyl groups in a lipid described herein may comprise saturated fatty acyl groups, monounsaturated fatty acyl groups (having a single unsaturated bond) and/or polyunsaturated fatty acyl groups (having two or more unsaturated bonds). In some embodiments, the unsaturated bonds are cis double bonds.

Examples of suitable saturated fatty acyl groups include, without limitation, lauroyl, myristoyl, palmitoyl and stearoyl.

Examples of suitable monounsaturated fatty acyl groups include, without limitation, oleoyl, palmitoleoyl, eicosenoyl, erucoyl, nervonoyl and vaccenoyl.

Examples of suitable polyunsaturated fatty acyl groups include, without limitation, linoleoyl, α-linolenoyl, γ-linolenoyl, dihomo-γ-linolenoyl, stearidonoyl, eicosatetraenoyl, eicosapentaenoyl, docosapentaenoyl, docosahexaenoyl, arachidonoyl and adrenoyl.

In some embodiments of any one of the embodiments described herein, the fatty acyl groups are selected from the group consisting of saturated and monounsaturated fatty acyl groups. In some embodiments, the fatty acyl groups are saturated fatty acyl groups.

Without being bound by any particular theory, it is believed that saturated and monounsaturated fatty acyl groups, particularly saturated fatty acyl groups, are relatively resistant to chemical reaction such as oxidation, and therefore provide a more resilient system.

In some embodiments of any one of the embodiments described herein, at least 50% of the fatty acyl groups are the same species of fatty acyl group (e.g., myristoyl, palmitoyl). In some embodiments, at least 75% of the fatty acyl groups are the same species of fatty acyl group. In some embodiments, at least 90% of the fatty acyl groups are the same species of fatty acyl group.

Exemplary phospholipids comprising a single species of fatty acyl group include 1,2-dimyristoyl-sn-glycero-3-phosphocholine and 1,2-dipalmitoyl-sn-glycero-3-phosphocholine.

It is to be appreciated that phase transitions, e.g., melting points (Tm), of the lipid bilayers and liposomes described herein may be determined by the skilled person by selecting suitable fatty acyl groups for inclusion in the lipids, for example, by selecting relatively short and/or unsaturated fatty acyl groups (e.g., myristoyl) to obtain a relatively low melting point; and/or by selecting relatively long and/or saturated fatty acyl groups (e.g., palmitoyl and/or stearoyl) to obtain a relatively high melting point.

In some embodiments of any one of the embodiments described herein, the liposomes described herein are characterized by a phase transition melting point above an expected ambient temperature of a surface to which the liposomes are applied (e.g., as described herein in any one of the respective embodiments), such that a surface coated by lipids at the expected ambient temperature will be coated predominantly by lipids in a solid phase. For example, in some embodiments, liposomes characterized by a melting point above a physiological temperature (e.g., about 37° C.) are used to coat a physiological surface with lipids (e.g., as described herein in any one of the respective embodiments).

Without being bound by any particular theory, it is believed that lipid coatings in a solid phase are more resilient against high pressures (e.g., 10 atmospheres or more), and are therefore particularly suitable for providing lubrication to surfaces (e.g., articular surfaces of joints) subject to such high pressures.

In some embodiments of any one of the embodiments described herein, the liposomes described herein are characterized by a phase transition melting point below an expected ambient temperature of a surface to which the liposomes are applied (e.g., as described herein in any one of the respective embodiments), such that a surface coated by lipids at the expected ambient temperature will be coated predominantly by lipids in a liquid phase. For example, in some embodiments, liposomes characterized by a melting point below a physiological temperature (e.g., about 36° C.) are used to coat a physiological surface with lipids (e.g., as described herein in any one of the respective embodiments).

Without being bound by any particular theory, it is believed that lipid coatings in a liquid phase provide the most effective lubrication at low pressures (e.g., below 10 atmospheres), although they may be insufficiently resilient against higher pressures, and are therefore particularly suitable for providing lubrication to surfaces which are generally not subjected to such high pressures.

In some embodiments of any one of the embodiments described herein, the liposomes described herein are characterized by a surface charge, which may be a positive surface charge or a negative surface charge.

As used herein, the phrase "surface charge" refers to an electric charge at or near a surface, such as an interface of a liposome with a solution. The phrase "surface charge" encompasses an electric charge associated with an electric potential at a surface (e.g., such that a positive electric potential at a surface is indicative of a positive surface charge, whereas a negative electric potential at a surface is indicative of a negative surface charge); as well as an electric charge which is closer to a surface than an electric charge of an opposite sign (e.g., as in a zwitterion wherein the positive charge is closer to the surface than the negative charge, or vice versa), such that an ion near the surface will interact primarily with the electric charge near the surface (due to the proximity) as opposed to the electric charge of an opposite sign. For example, phosphatidylcholine liposomes typically exhibit a positive surface charge because the positive charge of the choline group is closer to the liposome surface than the negative charge of the phosphate group.

Optionally, a surface charge of a liposome is associated with a net charge of the lipid molecules in the liposome, for example, a liposome comprising anionic lipids has a negative surface charge, and/or a liposome comprising cationic lipids has a positive surface charge.

Alternatively or additionally, a surface charge of a liposome is associated with a dipole of lipid molecules (e.g., zwitterionic lipid molecules) in the liposome, for example, a liposome comprising a zwitterionic lipid comprising a phosphocholine group may have a positive surface charge due to the positively charged ammonium groups in the phosphocholine groups being (on average) closer to the surface of the liposomes than the negatively charged phosphate groups in the phosphocholine groups.

The skilled person will be readily capable of determining a surface charge. For example, the sign of a surface charge may be determined by comparing the propensity of a surface (e.g., of a liposome) to bind to anionic vs. cationic compounds (e.g., labeling compounds) and/or by zeta potential measurement (e.g., according to standard techniques used in the art).

In some embodiments of any one of the embodiments described herein, the liposomes rupture upon contact with the water-soluble polymer(s) (e.g., on a surface). Liposome rupture may optionally result in a lipid bilayer in the liposomes being converted from a curved geometry (e.g., as in the relatively spherical liposomes) to a flatter geometry which complements the geometry of the surface and/or the water-soluble polymer(s) attached to the surface (e.g., thereby enhancing affinity of the lipids to the surface); and/or which results in a flatter, smoother lipid-coated surface (e.g., thereby further reducing friction).

Without being bound by any particular theory, it is believed that rupture of liposomes is induced by affinity of the surface-attached water-soluble polymer(s) to the lipids in the liposome, whereby rupture of the liposomes allows a greater area of the surface-attached water-soluble polymer(s) to come into contact with lipids, thereby increasing an amount of energetically favorable interactions between the water-soluble polymer(s) and lipid.

In some embodiments of any one of the embodiments described herein, liposomes and water-soluble polymer(s) are selected such that the selected water-soluble polymer(s) is effective at rupturing the selected liposomes.

Water-Soluble Polymer(s):

The water-soluble polymer(s) according to any one of the embodiments described in this section may be used in the context of any one of the embodiments of any of the aspects of the inventions described herein, and in combination with liposomes and/or lipids according to any one of the embodiments described herein with respect to liposomes and/or lipids.

As used herein, the phrase "water-soluble polymer" encompasses polymers having a solubility of at least 1 gram per liter in an aqueous (e.g., water) environment at pH 7 (at 25° C.).

In some embodiments of any of the embodiments described herein, the water-soluble polymer has a solubility of at least 2 grams per liter (under the abovementioned conditions). In some embodiments, the solubility is at least 5 grams per liter. In some embodiments, the solubility is at least 10 grams per liter. In some embodiments, the solubility is at least 20 grams per liter. In some embodiments, the solubility is at least 50 grams per liter. In some embodiments, the solubility is at least 100 grams per liter.

The water-soluble polymer(s) according to any of the embodiments described herein may comprise at least one ionic polymer and/or at least one non-ionic polymer which are water-soluble as defined herein.

As used herein, the phrase "non-ionic polymer" refers to a polymer which does not have a charged group.

Examples of suitable non-ionic water-soluble polymers include, without limitation, polyvinylpyrrolidone (also referred to herein interchangeably as povidone and/or PVP) and polyethylene oxide (also referred to herein interchangeably as PEO, PEG and/or polyethylene glycol).

As used herein, the phrase "ionic polymer" refers to polymers having at least one charged group, and encompasses polymers having a net negative charge (also referred to herein as "anionic polymers"), polymers having a net positive charge (also referred to herein as "cationic polymers"), and polymers having no net charge (also referred to herein as "zwitterionic polymers"), in an aqueous (e.g., water) environment at pH 7.

Herein throughout, the phrase "charged group" refers to any functional group (e.g., a functional group described herein) which is ionic (as defined herein), including, for example, amine, carboxylic acid, sulfate, sulfonate, phosphate and phosphonate. Thus, each electric charge in a moiety or molecule is associated with one charged group, although a single charged group (e.g., non-substituted phosphate) may be associated with more than one electric charge of the same sign (e.g., a dianion, a dication).

Herein throughout, the term "ionic" refers to the presence of an electric charge on at least one atom in a moiety and/or molecule (in at least 50% of moieties and/or molecules in a population) in an aqueous medium (e.g., water) at pH 7. The electric charge may be negative (anionic) or positive (cationic). If more than one electric charge is present, the electric charges may be negative (anionic) and/or positive (cationic), for example, both a negative and a positive charge may be present (zwitterionic).

In some embodiments of any one of the embodiments described herein relating to an ionic polymer, at least 75% of the ionic groups in the polymer have the same charge, that is, at least 75% of the ionic groups are cationic groups or are anionic groups, such that the polymer is substantially cationic or anionic, respectively. In some embodiments, at least 90% of the ionic groups in the polymer have the same charge. In some embodiments, at least 95% of the ionic groups in the polymer have the same charge. In some embodiments, at least 98% of the ionic groups in the polymer have the same charge. In some embodiments, at least 99% of the ionic groups in the polymer have the same charge.

In some embodiments of any one of the embodiments described herein, about 50% of the ionic groups in the polymer have a positive charge and about 50% of the ionic groups in the polymer have a negative charge, such that the polymer is substantially zwitterionic.

In some embodiments of any one of the embodiments described herein, the ionic polymer is characterized by a charge density of from 1 to 6 charged groups (ionic groups) per 1 kDa molecular weight of the polymer. In some embodiments, the ionic polymer has from 1.5 to 4 charged groups per 1 kDa. In some embodiments, the ionic polymer has from 2 to 3 charged groups per 1 kDa.

In some embodiments of any one of the embodiments described herein, the ionic polymer is characterized by a net charge (i.e., the difference between the number of anionic groups and the number of cationic groups) of from 1 to 6 electric charges per 1 kDa molecular weight of the polymer. In some embodiments, the ionic polymer has a net charge of from 1.5 to 4 charges per 1 kDa. In some embodiments, the ionic polymer has a net charge of from 2 to 3 charges per 1 kDa.

In some embodiments of any one of the embodiments described herein, the ionic polymer is an anionic polymer, for example, a polymer characterized by a net negative charge of from 1 to 6 electric charges per 1 kDa molecular weight of the polymer.

In some embodiments of any one of the embodiments described herein, the ionic polymer is a cationic polymer, for example, a polymer characterized by a net positive charge of from 1 to 6 electric charges per 1 kDa molecular weight of the polymer.

In some embodiments of any one of the embodiments described herein, the ionic polymer is a polysaccharide (which is an ionic polysaccharide).

As used herein throughout, the term "polysaccharide" refers to a polymer composed primarily (at least 50 weight percents) of monosaccharide units linked by glycosidic linkages.

As used herein, the term "monosaccharide" encompasses carbohydrates per se (having the formula $Cn(H_2O)n$, wherein n is at least 3, typically from 3 to 10), as well as derivatives thereof such as amino sugars, in which at least one hydroxyl group is replaced by an amine or amide group; sugar acids, in which one or two carbon atoms are oxidized to form a carboxylate group; acylated monosaccharides, in which at least one hydroxyl group and/or amine group is substituted by an acyl group (e.g., acetyl); and sulfated monosaccharides, in which at least one hydroxyl group is replaced by a sulfate group.

Examples of monosaccharides include, without limitation, hexoses (e.g., D-hexoses and/or L-hexoses) such as allose, altrose, glucose, mannose, gulose, idose, galactose, talose, psicose, fructose, sorbose and tagatose; pentoses (e.g., D-pentoses and/or L-pentoses) such as arabinose, lyxose, xylose, ribose, ribulose and xylulose; and hexose derivatives such as glucuronic acid, iduronic acid, manuronic acid, guluronic acid, glucosamine and N-alkyl derivatives thereof, galactosamine and N-alkyl derivatives thereof, N-acetylglucosamine, N-acetylgalactosamine, and monosulfated and disulfated N-acetylgalactosamine, glucuronic acid and iduronic acid.

As used herein, the phrase "glycosidic linkage" refers to a bond between a hemiacetal group of one compound (e.g., a monosaccharide monomer) and a hydroxyl group of another compound (e.g., another monosaccharide monomer).

Examples of ionic polysaccharides include, without limitation, hyaluronic acid, chondroitin sulfate, alginic acid, xanthan gum, chitosan and N-alkyl chitosan derivatives.

Hyaluronic acid is an anionic polysaccharide comprising anionic glucuronic acid monomer units along with non-ionic N-acetylglucosamine monomer units. Hyaluronic acid is an exemplary anionic polymer.

Chondroitin sulfate is an anionic polysaccharide comprising anionic sulfated (e.g., monosulfated and/or disulfated) N-acetylgalactosamine, glucuronic acid and/or iduronic acid monomer units, and anionic glucuronic acid and/or iduronic acid monomer units, along with non-ionic N-acetylgalactosamine monomer units.

Alginic acid is an anionic polysaccharide comprising anionic mannuronic acid and guluronic acid monomer units.

Xanthan gum is an anionic polysaccharide comprising anionic glucuronic acid monomer units, along with non-ionic glucose and mannose monomer units (including acetyl and/or pyruvyl derivatives thereof).

Chitosan is a cationic polysaccharide comprising cationic glucosamine monomer units, optionally along with non-ionic N-acetylglucosamine monomer units. In N-alkyl chitosan derivatives, at least a portion of the glucosamine units comprise 1, 2 or 3 alkyl groups, preferably $C_{1-4}$ alkyl, attached to the nitrogen atom. In some embodiments of any one of the embodiments described herein, the alkyl groups attached to the nitrogen atoms are each independently methyl or ethyl. In some embodiments, the alkyls are methyl. In some embodiments, the N-alkylated monomer unit is N-trimethylglucosamine.

Herein, the terms "hyaluronic acid", "chondroitin sulfate", "alginic acid", "xanthan gum", "chitosan", "N-alkyl chitosan derivatives" and any other ionic compounds named herein, encompass all salts of the named compounds along with the non-ionic forms (e.g., acid forms of the anionic polysaccharides, and the free base forms of the cationic polysaccharides).

Without being bound by any particular theory, it is believed that hyaluronic acid on a surface is particularly effective at binding to liposomes and rupturing them, thereby forming a lipid coating (e.g., lipid bilayer) with relatively high affinity to the surface.

In some embodiments of any one of the embodiments described herein, the polysaccharide is in a form of a salt. In some embodiments, the salt is a pharmaceutically acceptable salt (e.g., an ophthalmically acceptable salt for an ophthalmic application described herein, a salt suitable for parenteral administration for a parenteral application described herein).

In some embodiments of any one of the embodiments described herein, the polysaccharide has from 0.2 to 1 charged groups per monosaccharide residue. In some embodiments, the polysaccharide has from 0.2 to 0.9 charged groups per monosaccharide residue. In some embodiments, the polysaccharide has from 0.3 to 0.7 charged groups per monosaccharide residue. In some embodiments, the polysaccharide has from 0.4 to 0.6 charged groups per monosaccharide residue. In some embodiments, the polysaccharide has about 0.5 charged groups per monosaccharide residue.

It is to be appreciated that a monosaccharide residue may comprise more than one charged group (e.g., a sulfate group and a carboxylate group).

In some embodiments of any one of the embodiments described herein, the monosaccharide residues comprise no more than one charged group, that is, 0 or 1 charged group.

In some embodiments of any one of the embodiments described herein, the polysaccharide is characterized by a net charge (i.e., the difference between the number of anionic groups and the number of cationic groups) of from 0.2 to 1 electric charges per monosaccharide residue. In some embodiments, the net charge is from 0.2 to 0.9 electric charges per monosaccharide residue. In some embodiments, the net charge is from 0.3 to 0.7 electric charges per monosaccharide residue. In some embodiments, the net charge is from 0.4 to 0.6 electric charges per monosaccharide residue. In some embodiments, the net charge is about 0.5 electric charges per monosaccharide residue.

In some embodiments of any one of the embodiments described herein, a molecular weight (i.e., average molecular weight) of the ionic polymer is in a range of from 0.05 to 10 MDa. In some embodiments, the molecular weight is from 0.05 to 5 MDa. In some embodiments, the molecular weight is from 0.5 to 10 MDa. In some embodiments, the molecular weight is from 0.5 to 5 MDa. In some embodiments, the ionic polymer is a polysaccharide having an aforementioned molecular weight. In some embodiments, the ionic polymer is hyaluronic acid having an aforementioned molecular weight.

Herein throughout, an "average molecule weight" of a polymer refers to weight-average molecular weight ($M_w$).

In some embodiments of any one of the embodiments described herein, the water-soluble polymer comprises one or more biopolymers.

Herein, the term "biopolymer" refers to a polymer naturally occurring in a living organism. Examples of biopolymers include, without limitation, polynucleotides (e.g., RNA and DNA), polypeptides, polysaccharides and conjugates thereof (e.g., glycoproteins and proteoglycans comprising polypeptide and polysaccharide moieties). It is to be appreciated that biopolymers may optionally comprise many different species of related monomeric units (e.g., about 20 different types of amino acid residues and/or various types of monosaccharide moieties) with little or no repetition of the specific species of monomeric units, yet are considered polymers because at least some of the monomeric units are related in structure (e.g., being amino acid residues or monosaccharide moieties).

In some embodiments of any one of the embodiments described herein, the biopolymer(s) comprises a polypeptide (optionally attached to one or more saccharide moieties) and/or a polysaccharide.

Examples of suitable biopolymers comprising a polypeptide include, without limitation, mucins and lubricin.

Herein, the term "lubricin" refers to a proteoglycan (also known in the art as "proteoglycan 4") of about 345 kDa. Human lubricin is encoded by the PRG4 gene. The lubricin optionally comprises a polypeptide sequence of isoform A and/or isoform B of lubricin, e.g., according to NCBI reference sequence NP_001121180.

Herein, the term "mucin" refers to a family of high molecular weight glycosylated proteins produced by many animals, and encompasses human mucins such as, for example, mucin 1 (e.g., according to NCBI reference sequence NP_001018016), mucin 2 (e.g., according to NCBI reference sequence NP_002448), mucin 3A (e.g., according to NCBI reference sequence NP_005951), mucin 3B, mucin 4 (e.g., according to NCBI reference sequence NP_004523), mucin 5AC, mucin 5B (e.g., according to NCBI reference sequence NP_002449), mucin 6 (e.g., according to NCBI reference sequence NP_005952), mucin 7 (e.g., according to NCBI reference sequence NP_001138478), mucin 8, mucin 12, mucin 13, mucin 15, mucin 16 (e.g., according to NCBI reference sequence NP_078966), mucin 17 (e.g., according to NCBI reference sequence NP_001035194), mucin 19, and mucin 20 (e.g., according to NCBI reference sequence NP_001269435).

The polysaccharide may be a non-ionic polymer (as defined herein) or an ionic polymer (as defined herein), e.g., according to any of the embodiments described herein relating to an ionic polysaccharide.

Hyaluronic acid (e.g., according to any of the respective embodiments described herein) is a non-limiting example of a suitable polysaccharide as well as a non-limiting example of a suitable anionic polymer.

In some embodiments of any one of the embodiments described herein, the water-soluble polymer(s) is selected to enhance an affinity of the liposomes to the surface, that is, the liposome lipids have a greater affinity to the surface coated by the water-soluble polymer(s) than to the surface in the absence of the water-soluble polymer(s).

In some embodiments of any one of the embodiments described herein, the water-soluble polymer(s) comprises an ionic polymer selected such that the liposomes are characterized by a surface charge having a sign opposite a sign of a net charge of the ionic polymer.

In some embodiments of any one of the embodiments described herein, the liposomes are characterized by a negative surface charge (e.g., as described herein in any one of the respective embodiments) and the water-soluble polymer(s) comprises an ionic polymer having a net positive charge (e.g., as described herein in any one of the respective embodiments). In some embodiments, the ionic polymer is a polysaccharide having a net positive charge (e.g., a cationic polysaccharide described herein in any one of the respective embodiments).

In some embodiments of any one of the embodiments described herein, the liposomes are characterized by a positive surface charge (e.g., as described herein in any one of the respective embodiments) and the water-soluble polymer(s) comprises an ionic polymer having a net negative charge (e.g., as described herein in any one of the respective embodiments). In some embodiments, the ionic polymer is a polysaccharide having a net negative charge (e.g., an anionic polysaccharide described herein in any one of the respective embodiments). In some embodiments, the ionic polymer is hyaluronic acid (optionally hyaluronate salts, in accordance with the definition of "hyaluronic acid" used herein).

In some embodiments of any one of the embodiments described herein, the amphiphilic lipid comprises at least one phospholipid which comprises a phosphoethanolamine group or N-alkyl derivative thereof (e.g., in any one of the respective embodiments) and the water-soluble polymer(s) comprises an ionic polymer having a net negative charge (e.g., as described herein in any one of the respective embodiments). In some embodiments, the ionic polymer is a polysaccharide having a net negative charge (e.g., an anionic polysaccharide described herein). In some embodiments, the ionic polymer is hyaluronic acid.

In some embodiments of any of the embodiments described herein, the water-soluble polymers described herein comprise at least two water-soluble polymers according to any of the respective embodiments described herein. In some embodiments, the water-soluble polymers comprise at least three water-soluble polymers according to any of the respective embodiments described herein.

In some embodiments of any of the embodiments described herein, the water-soluble polymers described herein comprise at least one biopolymer (according to any of the respective embodiments described herein) in combination with at least one non-ionic polymer (according to any of the respective embodiments described herein). In some embodiments, the water-soluble polymers described herein comprise at least one mucin and/or lubricin biopolymer (according to any of the respective embodiments described herein) in combination with at least one non-ionic polymer (according to any of the respective embodiments described herein).

In some embodiments of any of the embodiments described herein, the water-soluble polymers described herein comprise at least one biopolymer (according to any of the respective embodiments described herein) in combination with at least one ionic polymer (according to any of the respective embodiments described herein). In some embodiments, the water-soluble polymers described herein comprise at least one mucin and/or lubricin biopolymer (according to any of the respective embodiments described herein) in combination with at least one ionic polymer (according to any of the respective embodiments described herein).

In some embodiments of any of the embodiments described herein, the water-soluble polymers described herein comprise at least one ionic polymer (according to any of the respective embodiments described herein) in combination with at least one non-ionic polymer (according to any of the respective embodiments described herein).

In some embodiments of any one of the embodiments described herein, a molecular weight (i.e., average molecular weight) of the water-soluble polymer(s) is in a range of from 3 kDa to 10 MDa. In some embodiments, the molecular weight is from 10 kDa to 10 MDa. In some embodiments, the molecular weight is from 20 kDa to 5 MDa. In some embodiments, the molecular weight is from 30 kDa to 2.5 MDa.

In some embodiments of any one of the embodiments described herein, a molecular weight (i.e., average molecular weight) of the water-soluble polymer(s) is in a range of from 3 kDa to 1 MDa. In some embodiments, the molecular weight is from 10 kDa to 1 MDa. In some embodiments, the molecular weight is from 20 kDa to 500 kDa. In some embodiments, the molecular weight is from 30 kDa to 250 kDa. In some embodiments, the water-soluble polymer(s) comprises a non-ionic polymer (according to any of the respective embodiments described herein) having an aforementioned molecular weight. In some embodiments, the non-ionic polymer is PVP and/or PEO having an aforementioned molecular weight.

In some embodiments of any one of the embodiments described herein, a molecular weight (i.e., average molecular weight) of the water-soluble polymer(s) is in a range of from 0.05 to 10 MDa. In some embodiments, the molecular weight is from 0.05 to 5 MDa. In some embodiments, the molecular weight is from 0.5 to 10 MDa. In some embodiments, the molecular weight is from 0.5 to 5 MDa. In some embodiments, the water-soluble polymer(s) comprises an ionic polymer (according to any of the respective embodiments described herein), optionally an ionic polysaccharide, having an aforementioned molecular weight. In some embodiments, the ionic polymer is hyaluronic acid having an aforementioned molecular weight.

In some embodiments, a concentration of a water-soluble polymer in the solution (according to any of the respective embodiments described herein) is in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the water-soluble polymer is PVP, PEO and/or an ionic polymer and/or polysaccharide (e.g., as described herein in any one of the respective embodiments), optionally hyaluronic acid.

In some embodiments, a concentration of each water-soluble polymer in the solution (according to any of the respective embodiments described herein) is in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the water-soluble polymer is PVP, PEO and/or hyaluronic acid In some embodiments, a total concentration of water-soluble polymer(s) in the solution (according to any of the respective embodiments described herein) is in a range of from 0.01 to 20 mg/ml. In some embodiments, the total concentration is in a range of from 0.03 to 20 mg/ml. In some embodiments, the total concentration is in a range of from 0.1 to 10 mg/ml. In some embodiments, the total concentration is in a range of from 0.3 to 10 mg/ml.

In some embodiments, a concentration of a water-soluble polymer in the solution (according to any of the respective embodiments described herein) is in a range of from 0.01 to 1 mg/ml. In some embodiments, the concentration is in a range of from 0.03 to 1 mg/ml. In some embodiments, the concentration is in a range of from 0.1 to 1 mg/ml. In some embodiments, the concentration is in a range of from 0.3 to 1 mg/ml. In some embodiments, the water-soluble polymer is PVP, PEO and/or an ionic polymer and/or polysaccharide (e.g., as described herein in any one of the respective embodiments), optionally hyaluronic acid.

In some embodiments, a concentration of each water-soluble polymer in the solution (according to any of the respective embodiments described herein) is in a range of from 0.01 to 1 mg/ml. In some embodiments, the concentration is in a range of from 0.03 to 1 mg/ml. In some embodiments, the concentration is in a range of from 0.1 to 1 mg/ml. In some embodiments, the concentration is in a range of from 0.3 to 1 mg/ml. In some embodiments, the water-soluble polymer is PVP, PEO and/or hyaluronic acid In some embodiments, a total concentration of water-soluble polymer(s) in the solution (according to any of the respective embodiments described herein) is in a range of from 0.01 to 2 mg/ml. In some embodiments, the total concentration is in a range of from 0.03 to 2 mg/ml. In some embodiments, the total concentration is in a range of from 0.1 to 1 mg/ml. In some embodiments, the total concentration is in a range of from 0.3 to 1 mg/ml.

In some embodiments, a concentration of a water-soluble polymer in the solution (according to any of the respective embodiments described herein) is in a range of from 0.01 to 3 mg/ml. In some embodiments, the concentration is in a range of from 0.01 to 1 mg/ml. In some embodiments, the concentration is in a range of from 0.01 to 0.3 mg/ml. In some embodiments, the concentration is in a range of from 0.01 to 0.1 mg/ml. In some embodiments, the water-soluble polymer is PVP, PEO and/or hyaluronic acid In some embodiments, a concentration of each water-soluble polymer in the solution (according to any of the respective embodiments described herein) is in a range of from 0.01 to 3 mg/ml. In some embodiments, the concentration is in a range of from 0.01 to 1 mg/ml. In some embodiments, the concentration is in a range of from 0.01 to 0.3 mg/ml. In some embodiments, the concentration is in a range of from 0.01 to 0.1 mg/ml. In some embodiments, the water-soluble polymer is PVP, PEO and/or hyaluronic acid.

In some embodiments, a total concentration of water-soluble polymer(s) in the solution (according to any of the respective embodiments described herein) is in a range of from 0.01 to 6 mg/ml. In some embodiments, the total concentration is in a range of from 0.01 to 2 mg/ml. In some embodiments, the total concentration is in a range of from 0.01 to 0.6 mg/ml. In some embodiments, the total concentration is in a range of from 0.01 to 0.2 mg/ml.

In some embodiments of any one of the embodiments described herein, the water soluble polymer(s) comprises hyaluronic acid, PVP and/or PEO at a concentration of less than 3 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml. In some embodiments, the hyaluronic acid, PVP and/or PEO is at least 0.3 mg/ml.

In some embodiments of any one of the embodiments described herein, the water soluble polymer(s) comprises hyaluronic acid, PVP and/or PEO at a concentration of less than 0.75 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml. In some embodiments, the hyaluronic acid, PVP and/or PEO concentration is at least 0.3 mg/ml.

In some embodiments of any one of the embodiments described herein, the water soluble polymer(s) comprises hyaluronic acid, PVP and/or PEO at a concentration of less than 0.5 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml. In some embodiments, the hyaluronic acid, PVP and/or PEO concentration is at least 0.3 mg/ml.

In some embodiments of any one of the embodiments described herein, the water soluble polymer(s) comprises hyaluronic acid, PVP and/or PEO at a concentration of less than 0.25 mg/ml. In some embodiments, the hyaluronic acid, PVP and/or PEO acid concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml.

In some embodiments of any one of the embodiments described herein, the water soluble polymer(s) comprises hyaluronic acid, PVP and/or PEO at a concentration of less than 0.1 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml.

In some embodiments of any one of the embodiments described herein, a viscosity of the solution (which may reflect at least in part a concentration of water-soluble polymer(s) therein) is no more than 1000 cP (centipoise). In some embodiments, the viscosity is no more than 500 cP. In some embodiments, the viscosity is no more than 200 cP. In some embodiments, the viscosity is no more than 100 cP. In some embodiments, the viscosity is no more than 50 cP. In some embodiments, the viscosity is no more than 20 cP. In some embodiments, the viscosity is no more than 10 cP. In some embodiments, the viscosity is no more than 5 cP. In some embodiments, the viscosity is no more than 3 cP. In some embodiments, the viscosity is no more than 2 cP. In some embodiments, the solution is an aqueous solution having a viscosity described herein.

Herein, viscosities of a solution are determined at a temperature of 20° C. and at a shear rate of 1 second$^{-1}$ (unless indicated otherwise).

Attachment of Water-Soluble Polymer to Surface:

Attachment of a water-soluble polymer to a surface according to any one of the embodiments described in this section may be used in the context of any one of the embodiments of any of the aspects of the inventions described herein, and in combination with liposomes and/or lipids according to any one of the embodiments described herein with respect to liposomes and/or lipids, and in combination with water-soluble polymer(s) according to any one of the embodiments described herein with respect to water-soluble polymer(s).

In some embodiments of any one of the embodiments described herein, the method of reducing a friction coefficient of a surface comprises modifying the surface and/or the water-soluble polymer(s), in order to facilitate attachment of the water-soluble polymer(s) to the surface. The modification may optionally comprise introduction of a functional group or moiety to one material (e.g., the surface or the water-soluble polymer(s)) capable of forming a covalent bond or selective non-covalent bond with the other material (e.g., the water-soluble polymer(s) or the surface).

In some embodiments of any one of the embodiments described herein, at least one water-soluble polymer is selected to be attachable to the surface.

Herein, the phrase "attachable to the surface" and variations thereof refer to a property of a molecule (e.g., at water-soluble polymer described herein) which renders it capable of attaching via covalent or non-covalent interactions to the surface. Examples of such interactions include, without limitation, covalent bonds, electrostatic attraction, hydrophobic bonds, hydrogen bonds, and aromatic interactions. It is to be appreciated that such a property depends on both the properties of the molecule (e.g., a water-soluble polymer described herein) and the properties of the surface, such that a molecule attachable to one surface is not necessarily attachable to another surface.

In some embodiments of any one of the embodiments described herein, the water-soluble polymer(s) is attachable to the surface by electrostatic interactions. In some such embodiments, the water-soluble polymer(s) comprises an ionic polymer having a net charge (e.g., characterized by a charge density described herein) which is of the opposite sign of a surface charge of the surface.

In some embodiments of any one of the embodiments described herein, the water-soluble polymer(s) is attachable to the surface by covalent binding and/or by selective non-covalent binding (e.g., as described herein in any one of the respective embodiments).

In some embodiments of any one of the embodiments described herein, the water-soluble polymer(s) comprises a modified water-soluble polymer, in which a water-soluble polymer (e.g., as described herein in any one of the respective embodiments) is modified so as to further comprise at least one functional group for attaching the polymer to the surface. In some embodiments, the modified water-soluble polymer comprises at least one functional group which forms a covalent bond with one or more specific functional groups (e.g., hydroxy, amine, thiohydroxy and/or oxo groups) which are present on the surface (e.g., a modified surface described herein or a non-modified surface).

Herein, the phrase "functional group for attaching" encompasses chemical groups and moieties of any size and any functionality.

In some embodiments of any one of the embodiments described herein, a water-soluble polymer comprises a dihydroxyphenyl functional group for attaching to a surface.

Herein, the term "dihydroxyphenyl" refers to an aryl group (as defined herein) which is a phenyl substituted by two hydroxyl groups at any positions thereof. The phenyl may optionally be substituted by additional substituents (which may optionally comprise additional hydroxyl groups), to thereby form a substituted dihydroxyphenyl group; or alternatively, the phenyl comprises no substituents other than the two hydroxyl groups, such that the dihydroxyphenyl group is an unsubstituted dihydroxyphenyl group.

In some embodiments of any one of the embodiments described herein, the dihydroxyphenyl group is an ortho-dihydroxyphenyl (wherein the hydroxyl groups are attached to the phenyl at adjacent positions) or a para-dihydroxyphenyl (wherein the hydroxyl groups are attached to opposite sides of the phenyl ring), each being a substituted or unsubstituted dihydroxyphenyl. In some such embodiments, the ortho-dihydroxyphenyl or para-dihydroxyphenyl is an unsubstituted dihydroxyphenyl.

In some embodiments of any one of the embodiments described herein, the dihydroxyphenyl group is a substituted or unsubstituted ortho-dihydroxyphenyl. In some such embodiments, the ortho-dihydroxyphenyl is an unsubstituted ortho-dihydroxyphenyl.

A dihydroxyphenyl group according to any of the respective embodiments described herein may optionally attach covalently and/or non-covalently to a surface according to any one or more attachment mechanism described for dihydroxyphenyl (catechol) groups in Lee et al. [*PNAS* 2006, 103:12999-13003] and/or Brodie et al. [*Biomedical Materials* 2011, 6:015014], the contents of each of which are incorporated in their entirety, and particularly contents regarding binding of dihydroxyphenyl (catechol) groups to surfaces.

Without being bound by any particular theory, it is believed that ortho-dihydroxyphenyl and para-dihydroxyphenyl groups are particularly suitable for forming covalent bonds by being oxidized (under even very mild oxidizing conditions) to a reactive quinone moiety, which may for covalent bonds, for example, with amine groups (e.g., primary amine groups), thiohydroxy groups and other phenyl (e.g., dihydroxyphenyl) groups. It is further believed that ortho-dihydroxyphenyl groups are particularly suitable for forming non-covalent bonds, for example, with an atom or functional group capable of binding to the two adjacent hydroxyl groups via electrostatic attraction (e.g., upon deprotonation of a hydroxyl group) and/or hydrogen bonds.

In some embodiments of any one of the embodiments described herein, the dihydroxyphenyl group is capable of forming covalent and/or non-covalent bonds with one or more functional groups on a surface, for example, depending on conditions such as pH. For example, a dihydroxyphenyl group may optionally be particularly susceptible to covalent bond formation with an amine group at a relatively basic pH, such as at least about 8.5 (e.g., a pH at which the amine is relatively nucleophilic, thereby facilitating covalent bond formation by nucleophilic attack), while being more susceptible to non-covalent bond formation with an amine at a lower pH (e.g., a pH at which the amine is positively charged, thereby facilitating electrostatic interactions and/or hydrogen bonding).

Modification of a molecule (e.g., water-soluble polymer) with dihydroxyphenyl groups may be performed using any suitable technique for conjugation known in the art. The skilled person will be readily capable of selecting a suitable technique for any given molecule (water-soluble polymer) to be modified.

In some embodiments of any one of the embodiments described herein, modification of a molecule (e.g., water-soluble polymer) is performed by conjugating a compound comprising dihydroxyphenyl group and an amine group to a functional group on the molecule being modified which can be coupled to an amine group. Dopamine is a non-limiting example of a compound comprising dihydroxyphenyl group and an amine group. Examples of functional groups which can be coupled to an amine group include, without limitation, carboxyl groups, which may be coupled (e.g., by a carbodiimide) to an amine to form an amide bond; and aldehyde groups, which may be coupled to an amine to form an imine.

In exemplary embodiments, the modified water-soluble polymer is hyaluronic acid conjugated to at least one dopamine moiety via an amide bond (by conjugation of a dopamine amine group to a hyaluronic acid carboxylic acid group). A percentage of carboxylic acid groups of hyaluronic acid conjugated to dopamine may optionally be, for example, in a range of from 0.1% to 90%, optionally from 1% to 50%, optionally from 3% to 25%, and optionally from 10% to 20%.

In some embodiments of any one of the embodiments described herein, the dihydroxyphenyl group is a functional group for attaching (covalently and/or non-covalently) to a surface which comprises amine groups, optionally primary amine groups. In some embodiments, such a surface comprises proteins, and the amine groups may optionally be lysine side chain amine groups and/or N-terminal amine groups. In some embodiments, the surface comprises collagen. In some embodiments, the surface comprises cartilage (e.g., articular cartilage).

In some embodiments of any one of the embodiments described herein, the method of reducing a friction coefficient of a surface comprises modifying the surface to obtain a modified surface. In some embodiments, the water-soluble polymer(s) is selected to be attachable to the modified surface.

In some embodiments of any one of the embodiments described herein, the modified surface is modified so as to have a functional group which forms a covalent bond with one or more specific functional groups (e.g., hydroxy, amine, thiohydroxy and/or oxo groups) and the water-soluble polymer(s) is selected to comprise one or more such groups, thereby being attachable to the modified surface.

In some embodiments of any one of the embodiments described herein, the modified surface is modified so as to have a moiety capable of selectively binding (e.g., by non-covalent binding) to a target moiety, and the water-soluble polymer(s) is selected to comprise one or more such target moieties, thereby being attachable to the modified surface. In some embodiments, the moiety on the modified surface and the target moiety on the water-soluble polymer are each a protein (or a fragment thereof) and corresponding ligand of the protein (e.g., avidin and biotin). For example, a protein (or protein domain) may optionally be attached to the surface to form a modified surface, and the water-soluble polymer(s) is selected to comprise the corresponding ligand; or a ligand may optionally be attached to the surface to form a modified surface, and the water-soluble polymer(s) is selected to comprise a protein (or fragment thereof) which binds to the ligand.

A water-soluble polymer selected to be attachable to the modified surface may be attachable per se, that is, the water-soluble polymer (e.g., as described herein in any one of the respective embodiments) may be attached to the surface without any modification to the polymer; or the water-soluble polymer may be a modified water-soluble polymer (e.g., as described herein in any one of the respective embodiments).

In some embodiments of any one of the embodiments described herein, a water-soluble polymer described herein is a modified water-soluble polymer in which at least a portion of the at least one functional group for attaching the polymer to the surface is a target moiety capable of selective non-covalent binding (e.g., as described herein in any one of the respective embodiments). Biotinylated water-soluble polymer is an example of such a modified water-soluble polymer.

In some embodiments of any one of the embodiments described herein, a water-soluble polymer described herein is selected so as to comprise, without modification to the polymer, a target moiety capable of selective non-covalent binding (e.g., as described herein in any one of the respective embodiments). In some embodiments, the water-soluble polymer is a ligand (e.g., a polysaccharide ligand, a polypeptide ligand) and the surface (e.g., modified surface) comprises a protein (or fragment thereof) which binds to such a ligand. In some embodiments, the water-soluble polymer is a protein (or fragment thereof) and the surface (e.g., modified surface) comprises a ligand which binds to such a protein (or fragment thereof).

Examples of functional groups for covalent attachment as described herein, e.g., of a water-soluble polymer (modified or non-modified) to a surface (modified or non-modified), include, without limitation:

nucleophilic groups such as thiohydroxy, amine (e.g., primary or secondary amine) and hydroxy, which may form covalent bonds with, e.g., a functional group comprising a nucleophilic leaving group, Michael acceptor, acyl halide, isocyanate and/or isothiocyanate (e.g., as described herein);

nucleophilic leaving groups such as halo, azide ($-N_3$), sulfate, phosphate, sulfonyl (e.g. mesyl, tosyl), N-hydroxysuccinimide (NHS) (e.g. NHS esters), sulfo-N-hydroxysuccinimide, and anhydride, which may form covalent bonds with, e.g., a nucleophilic group (e.g., as described herein);

Michael acceptors such as enones (e.g., maleimide, acrylate, methacrylate, acrylamide, methacrylamide), nitro groups and vinyl sulfone, which may form covalent bonds with, e.g., a nucleophilic group (e.g., as described herein), optionally thiohydroxy;

dihydroxyphenyl groups (according to any of the respective embodiments described herein, which may form covalent bonds with, e.g., a nucleophilic group (e.g., as described herein) and/or a substituted or unsubstituted phenyl group (e.g., another dihydroxyphenyl group), as described herein;

acyl halide ($-C(=O)$-halogen), isocyanate ($-NCO$) and isothiocyanate ($-N=C=S$), which may form covalent bonds with, e.g., a nucleophilic group (e.g., as described herein);

carboxylate (—C(=O)OH), which may form covalent bonds with, e.g., an amine (e.g., primary amine) to form an amide bond; and oxo groups (e.g., aldehydes), which may form covalent imine bonds with amines (e.g., primary amines).

For any of the abovementioned functional groups for covalent attachment, the functional group may be on the water-soluble polymer (e.g., modified water-soluble polymer) or on the surface (e.g., modified surface).

In some embodiments of any one of the embodiments described herein, attachment of the water-soluble polymer(s) to the surface is effected via a linker.

Herein, the term "linker" refers to a compound or moiety which binds (via covalent and/or non-covalent bonds) to two or more substances (e.g., a surface described herein and at least one water-soluble polymer described herein). In embodiments, wherein the linker binds only via non-covalent bonds, the linker may be regarded as an independent compound. In embodiments wherein the linker binds to at least one substance by at least one covalent bond, the linker may be considered as a moiety which is a part of a substance to which it is bound, for example, a moiety of a modified surface and/or a modified water-soluble polymer described herein.

In some embodiments of any one of the embodiments described herein, the linker comprises at least one functional group or moiety which binds to the surface non-covalently (e.g., as described herein in any one of the respective embodiments), and at least one functional group or moiety which binds to the water-soluble polymer non-covalently (e.g., as described herein in any one of the respective embodiments). In some embodiments, the water-soluble polymer bound by the functional group or moiety is a polysaccharide (e.g., as described herein in any one of the respective embodiments), and the linker comprises at least one polysaccharide-binding polypeptide capable of selectively binding to the polysaccharide (e.g., as described herein in any one of the respective embodiments). In some embodiments, the water-soluble polymer is hyaluronic acid (e.g., as described herein in any one of the respective embodiments), and the linker comprises at least one hyaluronic acid-binding polypeptide capable of selectively binding to the hyaluronic acid (e.g., as described herein in any one of the respective embodiments).

In some embodiments of any one of the embodiments described herein, attachment of the water-soluble polymer to the surface comprises attaching the linker to the surface non-covalently, thereby forming a modified surface to which the water-soluble polymer is attachable. Such a modified surface comprises at least one functional group or moiety capable of binding to the water-soluble polymer non-covalently. In some embodiments, a method described herein comprises attaching the linker to the surface prior to effecting attachment of the water-soluble polymer to the resulting modified surface.

In some embodiments of any one of the embodiments described herein, attachment of the water-soluble polymer to the surface comprises attaching the linker to the water-soluble polymer non-covalently, thereby forming a modified water-soluble polymer which is attachable to the surface. Such a modified water-soluble polymer comprises at least one functional group or moiety capable of binding to the surface non-covalently. In some embodiments, a method described herein comprises attaching the linker to the water-soluble polymer prior to effecting attachment of the resulting modified water-soluble polymer to the surface.

In some embodiments of any one of the embodiments described herein, the linker comprises at least one functional group or moiety which binds to the surface covalently (e.g., as described herein in any one of the respective embodiments), and at least one functional group or moiety which binds to the water-soluble polymer covalently (e.g., as described herein in any one of the respective embodiments).

In some embodiments of any one of the embodiments described herein, attachment of the water-soluble polymer to the surface comprises attaching the linker to the surface covalently, thereby forming a modified surface to which the water-soluble polymer is attachable. Such a modified surface comprises at least one functional group or moiety capable of binding to the water-soluble polymer covalently. In some embodiments, a method described herein comprises attaching the linker to the surface prior to effecting attachment of the water-soluble polymer to the resulting modified surface.

In some embodiments of any one of the embodiments described herein, attachment of the water-soluble polymer to the surface comprises attaching the linker to the water-soluble polymer covalently, thereby forming a modified water-soluble polymer which is attachable to the surface. Such a modified water-soluble polymer comprises at least one functional group or moiety capable of binding to the surface covalently. In some embodiments, a method described herein comprises attaching the linker to the water-soluble polymer prior to effecting attachment of the resulting modified water-soluble polymer to the surface.

In some embodiments of any one of the embodiments described herein, the linker comprises at least one functional group or moiety which binds to the surface non-covalently (e.g., as described herein in any one of the respective embodiments), and at least one functional group or moiety which binds to the water-soluble polymer covalently (e.g., as described herein in any one of the respective embodiments).

In some embodiments of any one of the embodiments described herein, attachment of the water-soluble polymer to the surface comprises attaching the linker to the surface non-covalently, thereby forming a modified surface to which the water-soluble polymer is attachable. Such a modified surface comprises at least one functional group or moiety capable of binding to the water-soluble polymer covalently. In some embodiments, a method described herein comprises attaching the linker to the surface prior to effecting attachment of the water-soluble polymer to the resulting modified surface.

In some embodiments of any one of the embodiments described herein, attachment of the water-soluble polymer to the surface comprises attaching the linker to the water-soluble polymer covalently, thereby forming a modified water-soluble polymer which is attachable to the surface. Such a modified water-soluble polymer comprises at least one functional group or moiety capable of binding to the surface non-covalently. In some embodiments, a method described herein comprises attaching the linker to the water-soluble polymer prior to effecting attachment of the resulting modified water-soluble polymer to the surface.

In some embodiments of any one of the embodiments described herein, the linker comprises at least one functional group or moiety which binds to the surface covalently (e.g., as described herein in any one of the respective embodiments), and at least one functional group or moiety which binds to the water-soluble polymer non-covalently (e.g., as described herein in any one of the respective embodiments). In some embodiments, the water-soluble polymer is a polysaccharide (e.g., as described herein in any one of the respective embodiments), and the linker comprises at least one polysaccharide-binding polypeptide capable of selectively binding to the polysaccharide (e.g., as described herein in any one of the respective embodiments). In some embodiments, the water-soluble polymer is hyaluronic acid (e.g., as described herein in any one of the respective embodiments), and the linker comprises at least one hyaluronic acid-binding polypeptide capable of selectively binding to the hyaluronic acid (e.g., as described herein in any one of the respective embodiments).

In some embodiments of any one of the embodiments described herein, attachment of the water-soluble polymer to the surface comprises attaching the linker to the surface covalently, thereby forming a modified surface to which the water-soluble polymer is attachable. Such a modified surface comprises at least one functional group or moiety capable of binding to the water-soluble polymer non-covalently. In some embodiments, a method described herein comprises attaching the linker to the surface prior to effecting attachment of the water-soluble polymer to the resulting modified surface.

In some embodiments of any one of the embodiments described herein, attachment of the water-soluble polymer to the surface comprises attaching the linker to the water-soluble polymer non-covalently, thereby forming a modified water-soluble polymer which is attachable to the surface. Such a modified water-soluble polymer comprises at least one functional group or moiety capable of binding to the surface covalently. In some embodiments, a method described herein comprises attaching the linker to the water-soluble polymer prior to effecting attachment of the resulting modified water-soluble polymer to the surface.

As used herein, the phrase "polysaccharide-binding polypeptide" encompasses any polypeptide or oligopeptide (e.g., peptide chains of at least 4 amino acid residues in length) capable of selectively binding (e.g., non-covalently) to a polysaccharide. A wide variety of polysaccharide-binding polypeptides and their binding specificities will be known to the skilled person, and include short peptide sequences (e.g., from 4 to 50, optionally 4 to 20 amino acid residues in length), and longer polypeptides such as proteins or fragments (e.g., carbohydrate-binding modules and/or domains) thereof. In addition, the phrase "polysaccharide-binding polypeptide" encompasses antibodies capable of specifically binding to a polysaccharide. Such antibodies will be available to the skilled person and/or the skilled person will know how to prepare such antibodies, using immunological techniques known in the art.

Examples of polysaccharide-binding polypeptides which may be used in some of any one of the embodiments of the invention include, without limitation, carbohydrate-binding modules (CBMs); and hyaluronic acid-binding peptides, polypeptides and/or modules (e.g., having a sequence as described in any of International Patent Application publication WO 2013/110056; International Patent Application publication WO 2014/071132; Barta et al. [*Biochem J* 1993, 292:947-949], Kohda et al. [*Cell* 1996, 86:767-775], Brisset & Perkins [*FEBS Lett* 1996, 388:211-216], Peach et al. [*J Cell Biol* 1993, 122:257-264] and Zaleski et al. [*Antimicrob Agents Chemother* 2006, 50:3856-3860], the contents of which are incorporated herein by reference in their entirety).

Examples of CBMs which may be used in some of any one of the embodiments of the invention, include, without limitation, CBMs belonging to the families CBM3, CBM4, CBM9, CBM10, CBM17 and/or CBM28 (which may optionally be used to bind cellulose, e.g., in a surface); CBM5, CBM12, CBM14, CBM18, CBM19 and/or CBM33 (which may optionally be used to bind chitin and/or other polysaccharides comprising N-acetylglucosamine, e.g., in some of the water-soluble polymers described herein); CBM15 (which may optionally be used to bind hemicellulose, e.g., in a wood-based surface); and/or CBM20, CBM21 and/or CBM48 (which may optionally be used to bind starch and/or glycogen).

It is expected that during the life of a patent maturing from this application many relevant functional groups and moieties for binding will be developed and/or uncovered and the scope of the terms "functional group", "moiety", "linker" and "polysaccharide-binding polypeptide" and the like is intended to include all such new technologies a priori.

In some embodiments of any one of the embodiments described herein, the water-soluble polymer is attached (e.g., covalently attached) to the surface, as described herein in any one of the respective embodiments, prior to contact of the water-soluble polymer and/or surface with the liposomes, thereby limiting reaction of the liposomes with reactive functional groups of the (modified or non-modified) water-soluble polymer and/or surface. In some embodiments, the water-soluble polymer and surface are essentially devoid of functional groups capable of covalently binding to the liposomes, when the liposomes are contacted with the water-soluble polymer and surface.

In some embodiments of any one of the embodiments described herein, the water-soluble polymer is attached (e.g., covalently attached) to the surface, as described herein in any one of the respective embodiments, concomitantly and/or subsequent to contact of the water-soluble polymer with liposomes, for example, embodiments in which the surface (modified or non-modified, as described herein in any one of the respective embodiments) is contacted with a solution comprising a water-soluble polymer (modified or non-modified, as described herein in any one of the respective embodiments), liposomes, and an aqueous carrier (e.g., as described herein in any one of the respective embodiments). In some such embodiments, the water-soluble polymer and surface (and optionally also the liposomes) are selected such that the water-soluble polymer is attachable to the surface in the presence of liposomes, that is, the liposomes do not interfere with attachment (e.g., covalent attachment) of the water-soluble polymer to the surface.

In some embodiments of any one of the embodiments described herein, the water-soluble polymer is attached (e.g., covalently attached) to the surface, as described herein in any one of the respective embodiments, concomitantly and/or subsequent to contact of the water-soluble polymer with liposomes, and a functional group on the water-soluble polymer for attaching the water-soluble polymer to the surface is selected so as not to be attachable to the liposome lipids. For example, the water-soluble polymer (e.g., modified water-soluble polymer) may optionally comprise a functional group which forms a covalent bond with a nucleophilic group described herein, and the lipids are selected so as to not covalently react with such a functional group.

In some embodiments of any one of the embodiments described herein, the water-soluble polymer is attached (e.g., covalently attached) to the surface, as described herein in any one of the respective embodiments, concomitantly and/or subsequent to contact of the surface with liposomes, and a functional group on the surface for attaching the water-soluble polymer to the surface is selected so as not to be attachable to the liposome lipids. For example, the surface (e.g., modified surface) may optionally comprise a functional group which forms a covalent bond with a nucleophilic group described herein, and the lipids are selected so as to not covalently react with such a functional group.

Phosphatidylcholines are examples of lipids which do not have a reactive nucleophilic group as described herein, whereas the similar phosphatidylethanolamines comprise a primary amine group which may react with a number of functional groups as described herein.

Composition-of-Matter:

According to another aspect of embodiments of the invention, there is provided a composition-of-matter comprising a substrate coated, on at least a portion of a surface thereof, by at least one water-soluble polymer. The water-soluble polymer(s) on the surface is coated by an amphiphilic lipid comprising at least one hydrophilic group.

According to another aspect of embodiments of the invention, there is provided an article of manufacture comprising a composition-of-matter according to any one of the embodiments described herein.

According to another aspect of embodiments of the invention, there is provided an article of manufacture comprising a composition-of-matter, the composition-of-matter comprising a substrate coated, on at least a portion of a surface thereof, by at least one water-soluble polymer, the article of manufacture being identified for use for efficiently attaching thereto an amphiphilic lipid so as to reduce a friction coefficient of said substrate (e.g., according to any of the respective embodiments described herein relating to attaching a lipid and/or reducing a friction coefficient). Herein, the term "composition-of-matter" refers to any composition comprising a plurality of substances (e.g., substrate, water-soluble polymer(s), amphiphilic lipid) in a form which does not exist in nature, and which does not include a portion of a human being. The form which does not exist in nature may optionally comprise natural substances in a combination which does not exist in nature, and/or may optionally comprise one or more substances which do not occur in nature. It is to be understood that this definition is not necessarily identical with a standard legal definition of the term.

Herein, the term "article of manufacture" refers to any article produced from materials in a manner which results in new forms, qualities, properties or combinations of the materials. It is to be understood that this definition is not necessarily identical with a standard legal definition of the term. The article of manufacture described herein may optionally consist essentially of the composition-of-matter, or alternatively, may comprise additional materials and/or parts.

In some embodiments of any one of the embodiments described herein, the amphiphilic lipid comprises at least one charged group (e.g., one or more negatively charged groups and/or one or more positively charged groups).

In some embodiments, the amphiphilic lipid is zwitterionic, comprising an equal number of negatively charged and positively charged groups (e.g., one of each).

A composition-of-matter according to embodiments of any of the aspects described in this section may include an amphiphilic lipid according to any one of the embodiments described herein with respect to liposomes and/or lipids, and water-soluble polymer(s) according to any one of the embodiments described herein with respect to water-soluble polymer(s). In addition, the water-soluble polymer(s) may be attached to the substrate according to any one of the embodiments described herein with respect to attachment of the water-soluble polymer(s) to a surface. In some embodiments, the water-soluble polymer(s) is attached to the substrate via a linker, as described herein in any one of the respective embodiments.

Thus, at least a portion of the composition-of-matter exhibits a layered structure, with the layers being in the order substrate-water-soluble polymer-amphiphilic lipid.

It is to be appreciated that the water-soluble polymer(s) may be in a form a very thin layer, and does not need to be in a bulk form (e.g., gel).

Indeed, without being bound by any particular theory, it is believed that a very thin layer may in many embodiments be more robust than a bulk form such as a gel, for example, with respect to high applied pressures.

In some embodiments of any one of the embodiments described herein, an average thickness of a layer of water-soluble polymer(s) on the surface is no more than 1 μm. In some embodiments, the average thickness is no more than 300 nm. In some embodiments, the average thickness is no more than 300 nm. In some embodiments, the thickness is no more than 100 nm. In some embodiments, the average thickness is no more than 30 nm. In some embodiments, the average thickness is no more than 10 nm. In some embodiments, the average thickness is no more than 3 nm. In exemplary embodiments, the average thickness is no more than 1.5 nm, the thickness being in a range of about 0.3-1.5 nm.

At least a portion of the molecules of the amphiphilic lipid are oriented such that hydrophilic groups thereof (e.g., charged groups) face outwards at a surface of the composition-of-matter. In some embodiments of any one of the embodiments described herein, at least 50% of the molecules are oriented such that hydrophilic groups (e.g., charged groups) face outwards. In some embodiments, at least 70% of the molecules are oriented such that hydrophilic groups (e.g., charged groups) face outwards. In some embodiments, at least 90% of the molecules are oriented such that hydrophilic groups (e.g., charged groups) face outwards. In some embodiments, at least 95% of the molecules are oriented such that hydrophilic groups (e.g., charged groups) face outwards. In some embodiments, at least 98% of the molecules are oriented such that hydrophilic groups (e.g., charged groups) face outwards. In some embodiments, at least 99% of the molecules are oriented such that hydrophilic groups (e.g., charged groups) face outwards.

As used herein, the phrase "face outwards at a surface" refers to a group in a molecule (e.g., a lipid) which is closer to the surface of the composition-of-matter than the center of gravity of the molecule is to the surface of the composition-of-matter, and farther from the substrate than the center of gravity of the molecule is from the substrate.

As discussed herein, and without being bound by any particular theory, it is believed that outwards facing hydrophilic groups (e.g., charged groups) according to embodiments of the invention effect highly effective lubrication due, at least in part, to hydration lubrication associated with hydrated hydrophilic groups, especially hydrated charged groups.

In some embodiments of any one of the embodiments described herein, at least a portion of the amphiphilic lipid is in a form of a bilayer, the bilayer having a lipophilic region (e.g., a layer consisting primarily of lipophilic moieties of the lipids) between two hydrophilic regions (e.g., hydrophilic layers) which comprise hydrophilic moieties (e.g., charged groups) of the lipids, that is, the lipophilic region is sandwiched between two hydrophilic regions.

The amphiphilic lipids in a bilayer are optionally oriented such that hydrophilic groups (e.g., charged groups) of lipids on the external side of the bilayer face outwards (at the surface of the composition-of-matter), and hydrophilic groups (e.g., charged groups) of lipids on the internal side of the bilayer face inwards, that is, towards the water-soluble polymer(s) and substrate, and the lipophilic moieties (e.g., fatty acyl groups) of the lipids on both sides of the bilayer (the internal and external sides) meet in the middle of the bilayer (e.g., thereby forming the lipophilic region of the bilayer).

In some embodiments of any one of the embodiments described herein, a bilayer is bound to the water-soluble polymer(s) by electrostatic attraction. The electrostatic attraction may comprise attraction between a pair of charged groups (e.g., an ionic bond), between an ionic group and a dipole and/or between two dipoles. A dipole involved in the electrostatic attraction may comprise, for example, a dipole of a non-ionic atom or group (e.g., hydroxy, amine) in a water-soluble polymer (e.g., non-ionic polymer) and/or a dipole of a zwitterion (e.g., a negatively charged group near a positively charged group, such as in phosphocholine).

In some embodiments of any one of the embodiments described herein, at least a portion of the amphiphilic lipid is in a form of a monolayer, which may optionally be interspersed among a bilayer. The monolayer has a lipophilic surface which comprises lipophilic moieties of the lipids and a hydrophilic surface which comprises hydrophilic moieties (e.g., charged groups) of the lipids.

The amphiphilic lipids in a monolayer are optionally oriented such that the hydrophilic surface of the monolayer faces outwards (at the surface of the composition-of-matter), and the lipophilic surface of the monolayer faces inwards, that is, towards the water-soluble polymer(s) and substrate. In some embodiments, a monolayer is bound to the water-soluble polymer(s) and/or substrate by a hydrophobic interaction. In some embodiments, a distribution of the monolayer in the coated substrate is associated with lipophilic regions in the water-soluble polymer(s) and/or gaps in the water-soluble polymer(s) which expose a region (e.g., lipophilic region) of the substrate, with lipids in other regions in the coated substrate being in a form other than a monolayer (e.g., a lipid bilayer, as described herein in any one of the respective embodiments).

In any of the embodiments described herein, the substrate may comprise any type of material or combination of different types of material, including inorganic material and/or organic material, in crystalline, amorphous and/or gel (e.g., hydrogel) forms, for example, metal, mineral, ceramic, glass, polymer (e.g., synthetic polymer, biopolymer), plant and/or animal biomass, and combinations thereof.

In some embodiments, the substrate comprises a physiological surface (e.g., a physiological tissue) and/or a surface in contact with and/or intended to come into contact with a physiological surface (e.g., as described herein in any one of the respective embodiments).

Physiological Environment:

In some embodiments of any one of the aspects described herein, the substrate and/or surface described herein is a physiological surface, and/or a surface in contact with and/or intended to come into contact with a physiological surface.

Any one of the embodiments described herein relating to a method of reducing a friction coefficient of a surface and/or a surface coated with at least one water-soluble polymer and an amphiphilic lipid may optionally be further limited according to any one of the embodiments in this section.

Herein, the phrase "physiological surface" refers to a surface of a part of a body.

A surface in contact with and/or intended to come into contact with a physiological surface may be, for example, an implant, and/or a suture.

Without being bound by any particular theory, it is believed that the method described herein is particularly suitable for application to physiological surfaces or surfaces which come into contact them, because the liposomes and water-soluble polymer(s) may readily be selected so as to be biocompatible, optionally even substances naturally occurring in the body, and because hydration lubrication mechanism (e.g., as described herein in any one of the respective embodiments) is fully compatible with aqueous environments such as physiological environments, as opposed, for example, to lubrication via non-aqueous liquid lubricants (e.g., oils).

In some embodiments of any one of the embodiments described herein, the surface is physiological surface of a joint (e.g., an articular surface) and/or a surface in contact with and/or intended to come into contact with a physiological surface of a joint (e.g., a joint implant). In some embodiments, the joint is a synovial joint.

In some embodiments of any one of the embodiments described herein, the physiological surface comprises cartilage. In some embodiments, the cartilage is articular cartilage.

In some embodiments according to any of the embodiments described herein relating to reducing a friction coefficient of a surface in a joint (e.g., an articular surface of a synovial joint), the liposomes are selected such that the lipids on the surface are in a solid phase in the joint (e.g., under physiological conditions).

Without being bound by any particular theory, it is believed that the solid phase is more robust the liquid phase, particularly at the relatively high pressures to which articular surfaces are commonly subjected.

In some embodiments of any one of the embodiments described herein, the liposomes are characterized by a phase transition melting point (Tm) above 37° C. In some embodiments, the Tm is above 38° C. In some embodiments, the Tm is above 39° C. In some embodiments, the Tm is above 40° C. In some embodiments, the Tm is above 42° C. In some embodiments, the Tm is above 45° C. In some embodiments, the Tm is above 50° C. In some embodiments, the Tm is above 55° C.

In some embodiments of any one of the embodiments described herein, attaching water-soluble polymer(s) to a physiological surface (e.g., an articular surface of a synovial joint) is effected by parenteral administration of an aqueous solution of the water-soluble polymer(s). The aqueous solution optionally comprises a physiologically acceptable carrier.

In some embodiments of any one of the embodiments described herein, contacting a water-soluble polymer with liposomes is effected in the vicinity of a physiological surface (e.g., an articular surface of a synovial joint) by parenteral administration of an aqueous solution of the liposomes. The aqueous solution optionally comprises a physiologically acceptable carrier.

In some embodiments of any one of the embodiments described herein, a solution comprising the water-soluble polymer(s) is administered (e.g., as described herein in any one of the respective embodiments), and subsequently, a solution comprising the liposomes is administered (e.g., as described herein in any one of the respective embodiments).

In some embodiments of any one of the embodiments described herein, the water-soluble polymer(s) and liposomes are administered concomitantly.

In some embodiments of any one of the embodiments described herein, the method comprises contacting a physiological surface (e.g., an articular surface of a synovial joint) with a solution comprising water-soluble polymer(s), liposomes and an aqueous carrier (e.g., as described herein in any one of the respective embodiments) via parenteral administration. The aqueous carrier is optionally a physiologically acceptable carrier.

In some embodiments of any one of the embodiments described herein, the method comprises modifying a physiological surface, for example, an articular surface of a synovial joint (e.g., as described herein in any one of the respective embodiments), thereby resulting in a modified physiological surface to which the water-soluble polymer is attachable (e.g., as described herein in any one of the respective embodiments). In some such embodiments, the modifying is effected with a solution comprising a reagent (e.g., a linker described herein) and an aqueous carrier (e.g., as described herein in any one of the respective embodiments) via parenteral administration. The aqueous carrier is optionally a physiologically acceptable carrier.

In some embodiments of any one of the embodiments described herein, the method comprises modifying a water-soluble polymer (e.g., as described herein in any one of the respective embodiments), thereby resulting in a modified water-soluble polymer attachable to a physiological surface, for example, an articular surface of a synovial joint. In some such embodiments, the modifying is effected with a solution comprising the modified water-soluble polymer, liposomes and an aqueous carrier (e.g., as described herein in any one of the respective embodiments) via parenteral administration. In such embodiments, the modification which enhances attachability does not require any additional treatment step, as the modification may performed (on the water-soluble polymer) ex vivo.

In some embodiments of any one of the embodiments described herein, parenteral administration of any of the solutions described herein comprises injection of a solution described herein solution into the vicinity of the surface. In some embodiments, the surface is an articular surface of a synovial joint and the solution is injected into the synovial cavity.

In some embodiments of any one of the embodiments described herein, the water-soluble polymer (e.g., hyaluronic acid) is attachable to the physiological surface by covalent binding and/or by selective non-covalent binding to collagen (e.g., as described herein in any one of the respective embodiments).

In some embodiments of any one of the embodiments described herein, the water-soluble polymer is a modified water-soluble polymer (e.g., as described herein in any one of the respective embodiments), in which a water-soluble polymer (e.g., hyaluronic acid) is modified so as to further comprise at least one functional group (e.g., a dihydroxyphenyl group described herein) for attaching the polymer to collagen.

In some embodiments of any one of the embodiments described herein, the modified or non-modified water-soluble polymer (e.g., hyaluronic acid) comprises at least one functional group which forms a covalent bond with amine groups (e.g., as described herein in any one of the respective embodiments) which are present on the physiological surface (e.g., amine groups of polypeptides, such as lysine residues, on the physiological surface). In some embodiments, the water-soluble polymer (e.g., modified water-soluble polymer) comprises at least one dihydroxyphenyl group (e.g., as described herein in any one of the respective embodiments). In some embodiments, the water-soluble polymer (e.g., modified water-soluble polymer) comprises at least one nucleophilic leaving group (e.g., as described herein in any one of the respective embodiments). In some embodiments, the water-soluble polymer (e.g., modified water-soluble polymer) comprises at least one N-hydroxysuccinimide leaving group.

In some embodiments of any one of the embodiments described herein, attachment of the water-soluble polymer to the physiological surface is effected via a linker (e.g., a linker as described herein in any one of the respective embodiments). In some embodiments, the linker is adapted for attaching a water-soluble polymer which is a polysaccharide to collagen. In some embodiments, the linker is adapted for attaching hyaluronic acid to collagen. In some embodiments, the collagen is type II collagen, also referred to as collagen II (a type of collagen which is abundant in articular cartilage).

Examples of functional groups or moieties which may optionally be included in a linker in order to effect attachment to articular cartilage and/or collagen include, without limitation, functional groups which form covalent bonds with amine groups as described herein (e.g., amine groups are abundant in collagen and cartilage); and moieties capable of selectively binding collagen (e.g., collagen II) non-covalently, such as collagen-binding polypeptides (e.g., collagen II-binding polypeptides).

As used herein, the phrase "collagen-binding polypeptide" encompasses any polypeptide or oligopeptide (e.g., peptide chains of at least 4 amino acid residues in length) capable of selectively binding (e.g., non-covalently) to a collagen (e.g., one type of collagen, some types of collagen, all types of collagen), including glycosylated polypeptides and oligopeptides such as peptidoglycans and proteoglycans. A wide variety of collagen-binding polypeptides and their binding specificities will be known to the skilled person, and include short peptide sequences (e.g., from 4 to 50, optionally 4 to 20 amino acid residues in length), and longer polypeptides such as proteins or fragments (e.g., collagen-binding domains) thereof. In addition, the phrase "collagen-binding polypeptide" encompasses antibodies capable of specifically binding to a collagen. Such antibodies will be available to the skilled person and/or the skilled person will know how to prepare such antibodies, using immunological techniques known in the art.

Examples of collagen-binding polypeptides which may be used in embodiments of the invention include, without limitation, collagen-binding proteins (e.g., decorin), fragments thereof and/or other polypeptides as described in U.S. Pat. No. 8,440,618, Abd-Elgaliel & Tung [*Biopolymers* 2013, 100:167-173], Paderi et al. [*Tissue Eng Part A* 2009, 15:2991-2999], Rothenfluh et al. [*Nat Mater* 2008, 7:248-254] and Helms et al. [*J Am Chem Soc* 2009, 131:11683-11685] (the contents of each of which are incorporated herein by reference in their entirety).

It is expected that during the life of a patent maturing from this application many relevant collagen-binding polypeptides will be developed and/or uncovered and the scope of the term "collagen-binding polypeptide" is intended to include all such new technologies a priori.

In some embodiments of any one of the embodiments described herein, the linker comprises at least one functional group or moiety which binds to the physiological surface (e.g., articular cartilage) non-covalently (e.g., as described herein in any one of the respective embodiments), and at least one functional group or moiety which binds to the water-soluble polymer non-covalently (e.g., as described herein in any one of the respective embodiments). In some embodiments, the linker comprises a moiety capable of selectively binding collagen (e.g., collagen II) non-covalently, e.g., as described herein in any one of the respective embodiments. In some embodiments, the linker comprises a collagen-binding polypeptide (e.g., a collagen II-binding polypeptide), e.g., as described herein in any one of the respective embodiments.

In some embodiments, attachment of the water-soluble polymer to the physiological surface (e.g., articular cartilage) comprises attaching the linker to the physiological surface non-covalently, thereby forming a modified physiological surface to which the water-soluble polymer is attachable. Such a modified physiological surface comprises at least one functional group or moiety capable of binding to the water-soluble polymer non-covalently. In some embodiments, a method described herein comprises attaching the linker to the physiological surface (e.g., articular cartilage) prior to effecting attachment of the water-soluble polymer to the resulting modified physiological surface.

In some embodiments, attachment of the water-soluble polymer to the physiological surface (e.g., articular cartilage) comprises attaching the linker to the water-soluble polymer non-covalently, thereby forming a modified water-soluble polymer which is attachable to the physiological surface. Such a modified water-soluble polymer comprises at least one functional group or moiety capable of binding to the physiological surface non-covalently. In some embodiments, a method described herein comprises attaching the linker to the water-soluble polymer prior to effecting attachment of the resulting modified water-soluble polymer to the physiological surface (e.g., articular cartilage).

In some embodiments of any one of the embodiments described herein, the linker comprises at least one functional group or moiety which binds to the physiological surface (e.g., articular cartilage) covalently (e.g., as described herein in any one of the respective embodiments), and at least one functional group or moiety which binds to the water-soluble polymer covalently (e.g., as described herein in any one of the respective embodiments). In some embodiments, the linker comprises a functional group which forms a covalent bond with an amine group (e.g., as described herein in any one of the respective embodiments). In some embodiments, the linker comprises at least one dihydroxyphenyl group. In some embodiments, the linker comprises at least one nucleophilic leaving group. In some embodiments, the linker comprises at least one N-hydroxysuccinimide leaving group.

In some embodiments, attachment of the water-soluble polymer to the physiological surface (e.g., articular cartilage) comprises attaching the linker to the physiological surface covalently, thereby forming a modified physiological surface to which the water-soluble polymer is attachable. Such a modified physiological surface comprises at least one functional group or moiety capable of binding to the water-soluble polymer covalently. In some embodiments, a method described herein comprises attaching the linker to the physiological surface (e.g., articular cartilage) prior to effecting attachment of the water-soluble polymer to the resulting modified physiological surface.

In some embodiments, attachment of the water-soluble polymer to the physiological surface (e.g., articular cartilage) comprises attaching the linker to the water-soluble polymer covalently, thereby forming a modified water-soluble polymer which is attachable to the physiological surface. Such a modified water-soluble polymer comprises at least one functional group or moiety capable of binding to the physiological surface covalently. In some embodiments, a method described herein comprises attaching the linker to the water-soluble polymer prior to effecting attachment of the resulting modified water-soluble polymer to the physiological surface (e.g., articular cartilage).

In some embodiments of any one of the embodiments described herein, the linker comprises at least one functional group or moiety which binds to the physiological surface (e.g., articular cartilage) non-covalently (e.g., as described herein in any one of the respective embodiments), and at least one functional group or moiety which binds to the water-soluble polymer covalently (e.g., as described herein in any one of the respective embodiments). In some embodiments, the linker comprises a moiety capable of selectively binding collagen (e.g., collagen II) non-covalently, e.g., as described herein in any one of the respective embodiments. In some embodiments, the linker comprises a collagen-binding polypeptide (e.g., a collagen II-binding polypeptide), e.g., as described herein in any one of the respective embodiments.

In some embodiments, attachment of the water-soluble polymer to the physiological surface (e.g., articular cartilage) comprises attaching the linker to the physiological surface non-covalently, thereby forming a modified physiological surface to which the water-soluble polymer is attachable. Such a modified physiological surface comprises at least one functional group or moiety capable of binding to the water-soluble polymer covalently. In some embodiments, a method described herein comprises attaching the linker to the physiological surface (e.g., articular cartilage) prior to effecting attachment of the water-soluble polymer to the resulting modified physiological surface.

In some embodiments, attachment of the water-soluble polymer to the physiological surface (e.g., articular cartilage) comprises attaching the linker to the water-soluble polymer covalently, thereby forming a modified water-soluble polymer which is attachable to the physiological surface. Such a modified water-soluble polymer comprises at least one functional group or moiety capable of binding to the physiological surface non-covalently. In some embodiments, a method described herein comprises attaching the linker to the water-soluble polymer prior to effecting attachment of the resulting modified water-soluble polymer to the physiological surface (e.g., articular cartilage).

In some embodiments of any one of the embodiments described herein, the linker comprises at least one functional group or moiety which binds to the physiological surface (e.g., articular cartilage) covalently (e.g., as described herein in any one of the respective embodiments), and at least one functional group or moiety which binds to the water-soluble polymer non-covalently (e.g., as described herein in any one of the respective embodiments). In some embodiments, the linker comprises a functional group which forms a covalent bond with an amine group (e.g., as described herein in any one of the respective embodiments). In some embodiments, the linker comprises at least one dihydroxyphenyl group. In some embodiments, the linker comprises at least one nucleophilic leaving group. In some embodiments, the linker comprises at least one N-hydroxysuccinimide leaving group.

In some embodiments, attachment of the water-soluble polymer to the physiological surface (e.g., articular cartilage) comprises attaching the linker to the physiological surface covalently, thereby forming a modified physiological surface to which the water-soluble polymer is attachable. Such a modified physiological surface comprises at least one functional group or moiety capable of binding to the water-soluble polymer non-covalently. In some embodiments, a method described herein comprises attaching the linker to the physiological surface (e.g., articular cartilage) prior to effecting attachment of the water-soluble polymer to the resulting modified physiological surface.

In some embodiments, attachment of the water-soluble polymer to the physiological surface (e.g., articular cartilage) comprises attaching the linker to the water-soluble polymer non-covalently, thereby forming a modified water-soluble polymer which is attachable to the physiological surface. Such a modified water-soluble polymer comprises at least one functional group or moiety capable of binding to the physiological surface covalently. In some embodiments, a method described herein comprises attaching the linker to the water-soluble polymer prior to effecting attachment of the resulting modified water-soluble polymer to the physiological surface (e.g., articular cartilage).

In some embodiments of any one of the embodiments described herein, the water-soluble polymer is a polysaccharide (e.g., as described herein in any one of the respective embodiments), and the linker comprises at least one polysaccharide-binding polypeptide capable of selectively binding to the polysaccharide (e.g., as described herein in any one of the respective embodiments), thereby effecting attachment to the physiological surface (e.g., articular cartilage). In some embodiments, the water-soluble polymer is hyaluronic acid (e.g., as described herein in any one of the respective embodiments), and the linker comprises at least one hyaluronic acid-binding polypeptide capable of selectively binding to the hyaluronic acid (e.g., as described herein in any one of the respective embodiments).

In some embodiments according to any of the embodiments described herein relating to reducing a friction coefficient of a surface in a joint, the method and/or solution described herein for reducing a friction coefficient is for use in the treatment of a synovial joint disorder associated with an increased friction coefficient of an articular surface in the synovial joint.

According to another aspect of embodiments of the invention, there is provided a use of a solution for reducing a friction coefficient of a surface, as described herein in any one of the respective embodiments, in the manufacture of a medicament for treating a synovial joint disorder associated with an increased friction coefficient of an articular surface in the synovial joint.

Examples of synovial joint disorders associated with an increased friction coefficient of an articular surface, and treatable according to embodiments of various aspects of the invention, include, without limitation, arthritis, traumatic joint injury, locked joint (also known in the art as joint locking), and joint injury associated with surgery.

In some embodiments, the arthritis is selected from the group consisting of osteoarthritis, rheumatoid arthritis and psoriatic arthritis.

In some embodiments, the locked joint is associated with osteochondritis dissecans and/or synovial osteochondromatosis.

The joint injury associated with surgery described herein may optionally be associated with surgery which directly inflicts damage on an articular surface (e.g., by incision), and/or surgery which damages an articular surface only indirectly. For example, surgery which repairs or otherwise affects tissue in the vicinity of the joint (e.g., ligaments and/or menisci) may be associated with joint injury due to altered mechanics in the joint.

The traumatic joint injury described herein may optionally be injury caused directly by trauma (e.g., inflicted at the time of the trauma) and/or injury caused by previous trauma (e.g., a post-traumatic injury which develops sometime after the trauma).

The water-soluble polymer(s) and/or liposomes may optionally be administered as part of a solution that comprises a physiologically acceptable carrier, for example an aqueous carrier which is a physiologically acceptable carrier.

Herein, the term "physiologically acceptable carrier" refers to a carrier or a diluent that does not cause significant irritation to a subject upon administration in the intended manner, and does not abrogate the activity and properties of the water-soluble polymer(s) and/or liposomes in the solution (e.g., their ability to reduce a friction coefficient of a surface, as described herein in any one of the respective embodiments). Examples, without limitations, of carriers are: propylene glycol, saline, emulsions and mixtures of organic solvents with water, as well as solid (e.g., powdered) and gaseous carriers.

Techniques for formulation and administration of compounds may be found in "Remington's Pharmaceutical Sciences" Mack Publishing Co., Easton, Pa., latest edition, which is incorporated herein by reference.

Solutions according to any one of the embodiments of the present invention may be manufactured by processes well known in the art, e.g., by means of conventional mixing or dissolving processes.

Solutions for use in accordance with the present invention thus may be formulated in conventional manner using one or more physiologically acceptable carriers, which facilitate processing of the water-soluble polymer(s) and/or liposomes into preparations which can be used pharmaceutically. Proper formulation is dependent upon the route of administration chosen.

For injection, the water-soluble polymer(s) and/or liposomes described herein may be formulated in aqueous solutions, preferably in physiologically compatible buffers such as Hank's solution, Ringer's solution, histidine buffer, or physiological saline buffer with or without organic solvents such as propylene glycol, polyethylene glycol.

The water-soluble polymer(s) and/or liposomes described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

The water-soluble polymer(s) and/or liposomes described herein may be formulated as an aqueous solution per se. Additionally, the solution may be in the form of a suspension and/or emulsions (e.g., the aqueous phase of a suspension or water-in-oil, oil-in-water or water-in-oil-in-oil emulsion), for example, in order to increase the viscosity of the formulation. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the water-soluble polymer(s) and/or liposomes described herein, for example, to allow for the preparation of highly concentrated solutions.

In some embodiments, the water-soluble polymer(s) and/or liposomes described herein may be in powder form for constitution with a suitable vehicle, e.g., sterile, pyrogen-free water, before use.

The solutions may be formulated wherein the active ingredient(s) (water-soluble polymer(s) and/or liposomes) are contained in an amount effective to achieve the intended purpose, for example, an amount effective to prevent, alleviate or ameliorate symptoms of a disorder in the subject being treated.

The dosage may vary depending upon the dosage form employed, the route of administration utilized, and the location of administration (e.g., the volume and/or surface of the region contacted with the water-soluble polymer(s) and/or liposomes).

The amount of a composition to be administered will, of course, be dependent on the subject being treated, the severity of the affliction, the manner of administration, the judgment of the prescribing physician, etc.

Solutions according to embodiments of the present invention may, if desired, be presented in a pack or dispenser device, such as an FDA (the U.S. Food and Drug Administration) approved kit, which may contain one or more unit dosage forms containing the active ingredient(s) (e.g., water-soluble polymer(s) and/or liposomes described herein). The pack may, for example, comprise metal or plastic foil, such as, but not limited to a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Solutions comprising water-soluble polymer(s) and/or liposomes, as described herein in any one of the respective embodiments, formulated in a physiologically acceptable carrier may also be prepared, placed in an appropriate container, and labeled for treatment of an indicated condition or diagnosis, as is detailed herein.

Additional Definitions

Herein, the term "alkyl" describes a saturated aliphatic hydrocarbon including straight chain and branched chain groups. Preferably, the alkyl group has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. Substituted alkyl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine.

Herein, the term "alkenyl" describes an unsaturated aliphatic hydrocarbon comprise at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted. Substituted alkenyl may have one or more substituents, whereby each substituent group can independently be, for example, cycloalkyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine.

Herein, the term "alkynyl" describes an unsaturated aliphatic hydrocarbon comprise at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine.

The alkyl, alkenyl and/or alkynyl group can be an end group, as this phrase is defined herein, wherein it is attached to a single adjacent atom, or a linking group, as this phrase is defined herein, which connects two or more moieties.

Herein, the phrase "end group" describes a group (e.g., a substituent) that is attached to a single moiety in the compound via one atom thereof.

The phrase "linking group" describes a group (e.g., a substituent) that is attached to two or more moieties in the compound.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or non-substituted. Substituted cycloalkyl may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The cycloalkyl group can be an end group, as this phrase is defined herein, wherein it is attached to a single adjacent atom, or a linking group, as this phrase is defined herein, connecting two or more moieties.

The term "aryl" describes an all-carbon monocyclic or fused-ring polycyclic (i.e., rings which share adjacent pairs of carbon atoms) groups having a completely conjugated pi-electron system. The aryl group may be substituted or non-substituted. Substituted aryl may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The aryl group can be an end group, as this term is defined herein, wherein it is attached to a single adjacent atom, or a linking group, as this term is defined herein, connecting two or more moieties. Phenyl and naphthyl are representative aryl end groups.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. Substituted heteroaryl may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The heteroaryl group can be an end group, as this phrase is defined herein, where it is attached to a single adjacent atom, or a linking group, as this phrase is defined herein, connecting two or more moieties. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. Substituted heteroalicyclic may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The heteroalicyclic group can be an end group, as this phrase is defined herein, where it is attached to a single adjacent atom, or a linking group, as this phrase is defined herein, connecting two or more moieties. Representative examples are piperidine, piperazine, tetrahydrofuran, tetrahydropyran, morpholine and the like.

As used herein, the terms "amine" and "amino" describe both a —NRxRy group —NRx- group, wherein Rx and Ry are each independently hydrogen, alkyl, cycloalkyl, aryl, heteroaryl or heteroalicyclic, as these terms are defined herein. When Rx or Ry is heteroaryl or heteroalicyclic, the amine nitrogen atom is bound to a carbon atom of the heteroaryl or heteroalicyclic ring.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of Rx and Ry is independently alkyl, cycloalkyl, aryl, heteroaryl or heteroalicyclic.

The terms "halide" and "halo" refer to fluorine, chlorine, bromine or iodine.

The term "haloalkyl" describes an alkyl group as defined herein, further substituted by one or more halide(s).

The term "phosphonate" refers to an —P(=O)(ORx)—OR$_Y$ end group, or to a —P(=O)(ORx)—O— linking group, where Rx and Ry are as defined herein.

The term "sulfoxide" or "sulfinyl" describes a —S(=O)—Rx end group or —S(=O)— linking group, where Rx is as defined herein.

The terms "sulfonate" and "sulfonyl" describe a —S(=O)$_2$-Rx end group or —S(=O)$_2$— linking group, where Rx is as defined herein.

The term "sulfonamide", as used herein, encompasses both S-sulfonamide and N-sulfonamide end groups, and a —S(=O)$_2$—NRx- linking group.

The term "S-sulfonamide" describes a —S(=O)$_2$—NRxR$_Y$ end group, with Rx and R$_Y$ as defined herein.

The term "N-sulfonamide" describes an RxS(=O)$_2$—NR$_Y$— end group, where Rx and R$_Y$ are as defined herein.

The term "carbonyl" as used herein, describes a —C(=O)—Rx end group or —C(=O) linking group, with Rx as defined herein.

The term "acyl" as used herein, describes a —C(=O)—Rx end group, with Rx as defined herein.

The terms "hydroxy" and "hydroxyl" describe a —OH group.

The term "alkoxy" describes both an —O-alkyl and an —O-cycloalkyl end group or linking group, as defined herein.

The term "aryloxy" describes both an —O-aryl and an —O-heteroaryl end group or linking group, as defined herein.

The term "thiohydroxy" describes a —SH group.

The term "thioalkoxy" describes both a —S-alkyl end group or linking group, and a —S-cycloalkyl end group or linking group, as defined herein.

The term "thioaryloxy" describes both a —S-aryl and a —S-heteroaryl end group or linking group, as defined herein.

The terms "cyano" and "nitrile" describe a —C≡N group.

The term "nitro" describes an —NO$_2$ group.

The term "azo" describes an —N=N-Rx end group or —N=N= linking group, with Rx as defined herein.

The terms "carboxy" and "carboxyl", as used herein, encompasses both C-carboxy and O-carboxy end groups, and a —C(=O)—O— linking group.

The term "C-carboxy" describes a —C(=O)—ORx end group, where Rx is as defined herein.

The term "O-carboxy" describes a —OC(=O)—Rx end group, where Rx is as defined herein.

The term "urea" describes a —NRxC(=O)—NRyRw end group or —NRxC(=O)—NRy- linking group, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The term "amide", as used herein, encompasses both C-amide and N-amide end groups, and a —C(=O)—NRx- linking group.

The term "C-amide" describes a —C(=O)—NRxRy end group, where Rx and Ry are as defined herein.

The term "N-amide" describes a RxC(=O)—NRy- end group, where Rx and Ry are as defined herein.

The term "carbamyl" or "carbamate", as used herein, encompasses N-carbamate and O-carbamate end groups, and a —OC(=O)—NRx- linking group.

The term "N-carbamate" describes an RyOC(=O)—NRx- end group, with Rx and Ry as defined herein.

The term "O-carbamate" describes an —OC(=O)—NRxRy end group, with Rx and Ry as defined herein.

The term "thiocarbamyl" or "thiocarbamate", as used herein, encompasses both O-thiocarbamate, S-thiocarbamate and N-thiocarbamate end groups, and a —OC(=S)—NRx- or —SC(=O)—NRx- linking group.

The term "O-thiocarbamate" describes a —OC(=S)—NRxRy end group, with Rx and Ry as defined herein.

The term "S-thiocarbamate" describes a —SC(=O)—NRxRy end group, with Rx and Ry as defined herein.

The term "N-thiocarbamate" describes an RyOC(=S)NRx- or RySC(=O)NRx- end group, with Rx and Ry as defined herein.

The term "guanidine" describes a —RxNC(=N)—NRyRw end group or —RxNC(=N)—NRy- linking group, where Rx, Ry and Rw are as defined herein.

The term "hydrazine", as used herein, describes a —NRx-NRyRw end group or —NRx-NRy- linking group, with Rx, Ry, and Rw as defined herein.

As used herein the term "about" refers to ±10%, and optionally ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Lubrication Solutions

Materials and Methods

Materials:

Hyaluronic acid (sodium hyaluronate, 1 and 1.5 MDa) was obtained from Lifecore Biomedical.

Phosphate buffer saline (PBS) was obtained from Sigma-Aldrich.

Phosphatidylcholines (PC), including dimyristoylphospatidylcholine (1,2-dimyristoyl-sn-glycero-3-phosphocholine; DMPC) and hydrogenated soy PC (HSPC), were obtained from Lipoid GmbH.

Polyethylene glycol (PEG or PEO), 200 kDa molecular weight, was obtained from Sigma-Aldrich.

Polyvinylpyrrolidone (PVP), 40 kDa molecular weight, was obtained from Sigma-Aldrich.

Etafilcon A (1-Day ACUVUE®) and Narafilcon A (1-Day TruEye®) contact lenses were obtained from Johnson & Johnson, immersed in saline solution in a blister-pack. The composition, water content and modulus of the contact lenses are as follows. Etafilcon A lenses contain 2-hydroxyethylmethacrylate (HEMA) and methacrylic acid (MA), have a water content of 58%, and a modulus of 0.3 MPa. Narafilcon A lenses contain silicone, have a water content of 46%, and a modulus of 0.66 MPa.

A saline commercial lens cleaning fluid (Sensitive Eyes® Plus saline solution) was obtained from Bausch & Lomb, and is referred to herein as "B&L saline".

Water used was purified by Barnsted NanoPure systems to a resistance of 18.2 MΩ-cm resistance with total organic content levels of less than approximately 1 part per billion.

Liposome Preparation (Multilamellar Vesicles):

Multilamellar vesicles (MLV) composed either of dimyristoylphosphatidylcholine (1,2-dimyristoyl-sn-glycero-3-phosphocholine; DMPC) or of hydrogenated soy PC (HSPC) were prepared by hydrating the lipids at a temperature at least 5° C. above the lipid melting point ($T_M$), followed by sonication, in phosphate buffer saline (PBS). Where MLV liposomes were mixed with hyaluronic acid (HA), the polymer solution (in PBS) was prepared in advance, and after full dissolution of the HA, the solution was warmed to a temperature at least 5° C. above the lipid $T_M$, and added to the lipids, followed by stirring to mix.

Liposome Preparation (Small Unilamellar Vesicles):

Multilamellar vesicles (MLV) composed of dimyristoylphosphatidylcholine (DMPC) or hydrogenated soy PC (HSPC) were prepared by hydrating the lipids at a temperature above the lipid melting point ($T_M$), according to the procedures described hereinabove. In order to obtain small unilamellar vesicles (SUV), the MLVs were downsized by stepwise extrusion through polycarbonate membranes, starting with a 400 nm and ending with 50 nm pore size membrane, using a Lipex 100 mL extruder system (Northern Lipids, Vancouver, Canada), at a temperature above the lipid $T_M$.

Where SUV liposomes were mixed with a polymer, the polymer solution (in PBS) was prepared in advance, and after full dissolution of the polymer, the polymer solution was added to the lipids, followed by stirring to mix for 2 hours.

Multilamellar vesicles and small unilamellar vesicles composed of other pure phosphatidylcholines, such as dipalmitoylphosphatidylcholine (DPPC), dilauroylphosphatidylcholine (DLPC) and/or distearoylphosphatidylcholine (DSPC), according to the procedures described hereinabove.

Friction Measurements:

Lenses were removed from their container, where they had been immersed in a phosphate buffer saline (PBS) solution, and were rinsed using PBS. The lenses were then immersed for 2 days in a PBS solution of liposomes and/or a polar polymer (hyaluronic acid (HA), polyvinylpyrrolidone (PVP) or polyethylene oxide (PEO)), or in PBS alone (as a control).

Prior to measurements in the tribometer, in all samples (including the controls), the lenses were thoroughly rinsed by a stream of B&L saline or PBS. The lenses were then mounted on the tribometer holder and friction forces measured while sliding against a glass surface and immersed in B&L saline or PBS.

Friction tests were performed with a UMT model tribometer (Bruker). Contact lenses were mounted on a cornea-mimicking holder, which has a typical geometry resembling the human cornea, as shown in FIGS. 1A and 1B. The contact lens was then positioned opposite a glass plate and immersed in B&L saline or PBS during the measurement. The normal loads used were 3 grams, 5 grams, 10 grams and 40 grams.

The glass substrates used were thin 24 mm×24 mm cover-glasses (Knittel Glaser, Germany). They were removed from their pack (edge-handled with latex gloves throughout), and glued into a standard 35 mm diameter polystyrene Petri dish using Devcon® 5 Minute® 2-component epoxy. Just prior to the friction measurements, the upper glass surface was wiped with an ethanol-moistened Kimwipes® tissue, then rinsed in de-ionized water to remove any ethanol traces, and the Petri dish then filled with the B&L saline or PBS.

The friction coefficient was calculated by dividing the measured lateral force during sliding by the applied normal force. Friction coefficient values are those of kinetic friction, which is related to the forces in the system that are measured when there is a sliding motion of the contact lens on the opposing glass surface. Parameters were as follows: sliding velocity 1 mm per second, frequency 1 Hz, and dwell time of 5 seconds prior to initiation of motion. Experiments were conducted at a temperature of 36±0.5° C. or 37±1° C.

Each friction coefficient value ($\mu$) is an average of friction measurements for at least 5 different etafilcon A (HEMA/MA) lenses, or for at least 3 different narafilcon A (silicone) lenses, for each immersion condition. Moreover, each friction measurement is an average over 180 cycles for each of 2 to 3 different contact position on the glass surface. The same glass surface was used for one entire set of experiments for a given lens type, and the order of measurements was as follows: first, saline controls; then a lens that had been immersed in HA; then a lens that had been immersed in HSPC; then a lens that had been immersed in HSPC+HA; then a lens that had been immersed in DMPC; then a lens that had been immersed in DMPC+HA. Between each different lens the B&L saline or PBS immersing the lens/substrate system was replaced by fresh B&L saline or PBS, respectively. The glass surface was then changed, and the measurements repeated (5 times for etafilcon A and 3 times for narafilcon A).

In one case, following the full set of measurements with a given glass substrate, the measurement for the (HSPC+HA)-immersed lens on the same substrate was repeated, and the earlier measured value (for the same (HSPC+HA)-immersed lens) was reproduced.

The mean pressure P over the contact area A was determined according to the equation: $P=F_N/A$, where $F_N$ is the applied normal load and, from Hertzian contact mechanics [Johnson, K. L., *Contact Mechanics* 2004, London: Cambridge University Press], $A=\pi(RF_N/K)^{2/3}$, where R is the radius of the rigid cornea-mimicking holder and K is the Young's modulus of the contact lens.

Dynamic Light Scattering (DLS):

Dynamic light scattering (DLS) measurements of the various suspensions were determined using a ZetaSizer µV apparatus (Malvern Instruments).

Results

Dynamic light scattering (DLS) measurements showed that HA in PBS had a hydrodynamic diameter of 135±20 nm. For the MLV HSPC and DMPC liposomes in PBS solution, DLS measurements yielded diameters of 3±1.5 µm and 1.4±0.7 µm, respectively.

DLS measurements of the MLV's HSPC and DMPC liposomes mixtures with HA indicated diameters of 2.5±1.5 µm and 2.8±1.5 µm, respectively.

Friction coefficients were measured for Etafilcon A and Narafilcon A lenses, which served as exemplary hydrogel surfaces, in B&L saline environment at 36±0.5° C., according to procedures described hereinabove, either following removal of the lens from the blister-pack and rinsing in B&L saline (labeled 'saline' in the figure legends), or following immersion in PBS solutions containing the tested liposomes (HSPC and DMPC MLVs at a concentration of 45 mM) and/or 1 MDa HA (1 M; 0.2 mg/ml), and rinsing in B&L saline.

The applied loads (L) were 5 grams, 10 grams or 40 grams, and the corresponding mean pressures P (in Atm units) are presented in FIGS. 2 and 3, respectively as L/P.

As shown in FIGS. 2 and 3, the sliding friction coefficients $\mu$ of hydrogel lenses that were only rinsed in B&L saline following removal from their blister-pack, and then slid across a glass slide immersed in B&L saline, was in the range 0.08±0.04 for HEMA hydrogel (Etafilcon A) and 0.2±0.1 for silicone hydrogel (Narafilcon A). These values are considered as the baseline control relative to the values obtained with other solutions, and are designated herein asp.

As further shown in FIGS. 2 and 3, following immersion in HA solution, the sliding friction coefficient $\mu$ decreased relative to the baseline value $\mu_0$, by 30% and 50%, for the Etafilcon A and the Narafilcon A hydrogel lenses, respectively.

Following immersion in liposome solutions, a significant reduction in the sliding friction coefficient $\mu$ relative to $\mu$ to was generally noted, ranging between 25% to about 75% for the HSPC liposomes and between 65% to 92% for the DMPC liposomes.

Following immersion in the HA/liposome mixtures, substantially higher reduction in sliding friction coefficients $\mu$ relative to $\mu$ to were invariably observed, ranging from about 2-fold reduction for Etafilcon (HEMA) immersed in HA+HSPC to more-than-10-fold reduction for Narafilcon (silicone) immersed in HA+DMPC.

In some cases, the friction coefficients were somewhat lower at the higher loads.

These results present a synergistic effect of a solution containing both HA and liposomes. It is to be understood that in sliding friction coefficient, when two or more lubricants are measured alone and in combination, it is expected that the combination would result in averaged values of the friction coefficient. However, surprisingly, a solution containing HA and the liposomes resulted in friction coefficient values which were substantially lower than the friction coefficient values obtained for either component alone, thus demonstrating a synergistic effect.

HA is known not to be a good boundary lubricant [Seror et al., *Biomacromolecules*, 13(11):3823-3832, (2012)]; Benz et al. *Journal of Biomedical Materials Research Part A*, 2004. 71A:6-15], although viscous solutions of HA, similarly to other viscous solutions, have been considered to act as non-boundary lubricants [Doughty, *Contact Lens and Anterior Eye* 1999, 22:116-126].

It is noted that all measurements were performed following 2-day immersion of the hydrogel lenses in the tested solutions and a subsequent thorough rinse in a stream of B&L saline, such that subsequent measurements were made in B&L saline alone. It is therefore assumed that there was no trace of free HA or liposomes in the liquid surrounding the hydrogel lenses in the tribometer.

Friction coefficients were then measured for Etafilcon A and Narafilcon A hydrogel lenses in a PBS environment at 37±1° C., according to procedures described hereinabove, following immersion in PBS solutions containing the HSPC and DMPC SUVs (at a concentration of 10 mM) and/or a polar polymer (1.5 MDa hyaluronic acid (HA), polyvinylpyrrolidone (PVP) or polyethylene oxide (PEO) at a concentration of 0.2 mg/ml), or in PBS alone (as a control).

Dynamic light scattering (DLS) measurements showed that HSPC SUVs had a diameter of ~100 nm, and DMPC SUVs had a diameter of ~72 nm.

The applied loads (L) were 3 grams or 10 grams, and the corresponding mean pressures (P) are presented in FIGS. 4-7, respectively as L (in grams)/P (in Atm units).

As shown in FIGS. 4-7, and in Table 1 below, immersion in DMPC (FIGS. 4 and 6) or HSPC (FIGS. 5 and 7) liposome solutions resulted in a significant reduction in the sliding friction coefficient $\mu$ of Etafilcon A (FIGS. 4 and 5) and Narafilcon A (FIGS. 6 and 7) hydrogel lenses relative to hydrogel lenses immersed in PBS, in accordance with the results described in Example 1.

As further shown in FIGS. 4-7 and in Table 1, immersion in polymer/liposome mixtures generally resulted in substantially higher reduction in sliding friction coefficients $\mu$ than did immersion in polymer solution or liposome solution, especially at a load of 10 grams.

It is noted that all measurements were performed following 2-day immersion of the hydrogel lenses in the tested solutions and a subsequent thorough rinse in a stream of PBS, such that subsequent measurements were made in PBS alone. It is therefore assumed that there was no trace of free polymer or liposomes in the liquid surrounding the hydrogel lenses in the tribometer. Thus, the results indicate an interaction and possible attachment of the polymers to the surface of the hydrogel.

Without being bound by any particular theory, it is believed that results at a load of 10 grams are more representative of long-term lubrication effects than are results at a load of 3 grams.

As shown in FIG. 4 and in Table 1, PVP/DMPC liposome and PEO/DMPC liposome mixtures resulted in a reduction of 50% or more in the friction coefficients of Etafilcon A hydrogel lenses in comparison with DMPC liposomes alone at a load of 10 grams.

As shown in FIG. 5, PVP/HSPC liposome and HA/HSPC liposome mixtures resulted in a reduction of 25-30% in the friction coefficients of Etafilcon A hydrogel lenses in comparison with HSPC liposomes alone at a load of 10 grams.

As further shown in FIGS. 4 and 5, the abovementioned polymer/liposome mixtures resulted in a reduction of about 90% or more in the friction coefficients of Etafilcon A hydrogel lenses in comparison with PBS or polymer solutions.

As shown in FIG. 6, PVP/DMPC liposome and HA/DMPC liposome mixtures resulted in a reduction of 22-40% in the friction coefficients of Narafilcon A hydrogel lenses in comparison with DMPC liposomes alone, and a reduction of 50-72% in comparison with PBS or the respective polymer solutions, at a load of 10 grams.

As shown in FIG. 7, PEO/HSPC liposome, PVP/HSPC liposome and HA/HSPC liposome mixtures resulted in a reduction of 40-54% in the friction coefficients of Narafilcon A hydrogel lenses in comparison with HSPC liposomes alone, and a reduction of 60-91% in comparison with PBS or the respective polymer solutions, at a load of 10 grams.

TABLE 1

Friction coefficients of Etafilcon A and Narafilcon A hydrogel contact lenses under different loads and mean pressures, following immersion in PBS solution with or without liposomes and/or a polar polymer (hyaluronic acid (HA), polyvinylpyrrolidone (PVP) or polyethylene oxide (PEO))

| | Mean | | | Polymer in PBS Solution | | | |
| --- | --- | --- | --- | --- | --- | --- | --- |
| Hydrogel | Load (grams) | Pressure (Atm) | Liposome type | No polymer | HA | PVP | PEO |
| Etafilcon A | 3 | 0.1 | No liposomes | 0.21 ± 0.07 | 0.055 ± 0.01 | 0.02 ± 0.005 | 0.2 ± 0.02 |
| | | | DMPC liposomes | 0.015 ± 0.005 | 0.012 ± 0.006 | 0.01 ± 0.005 | 0.009 ± 0.003 |

TABLE 1-continued

Friction coefficients of Etafilcon A and Narafilcon A hydrogel contact lenses under different loads and mean pressures, following immersion in PBS solution with or without liposomes and/or a polar polymer (hyaluronic acid (HA), polyvinylpyrrolidone (PVP) or polyethylene oxide (PEO))

| Hydrogel | Load (grams) | Mean Pressure (Atm) | Liposome type | Polymer in PBS Solution | | | |
|---|---|---|---|---|---|---|---|
| | | | | No polymer | HA | PVP | PEO |
| | | | HSPC liposomes | 0.016 ± 0.007 | 0.015 ± 0.005 | 0.011 ± 0.003 | N.D. |
| | 10 | 0.16 | No liposomes | 0.28 ± 0.055 | 0.31 ± 0.1 | 0.11 ± 0.03 | 0.45 ± 0.05 |
| | | | DMPC liposomes | 0.024 ± 0.007 | 0.024 ± 0.008 | 0.012 ± 0.004 | 0.009 ± 0.003 |
| | | | HSPC liposomes | 0.024 ± 0.009 | 0.017 ± 0.005 | 0.018 ± 0.003 | N.D. |
| Narafilcon A | 3 | 0.18 | No liposomes | 0.051 ± 0.015 | 0.025 ± 0.005 | 0.02 ± 0.01 | 0.09 ± 0.03 |
| | | | DMPC liposomes | 0.015 ± 0.005 | 0.016 ± 0.005 | 0.01 ± 0.0035 | N.D. |
| | | | HSPC liposomes | 0.02 ± 0.004 | 0.018 ± 0.006 | 0.013 ± 0.004 | 0.012 ± 0.004 |
| | 10 | 0.26 | No liposomes | 0.067 ± 0.025 | 0.05 ± 0.017 | 0.054 ± 0.017 | 0.12 ± 0.028 |
| | | | DMPC liposomes | 0.032 ± 0.005 | 0.025 ± 0.005 | 0.019 ± 0.007 | N.D. |
| | | | HSPC liposomes | 0.033 ± 0.008 | 0.02 ± 0.01 | 0.016 ± 0.008 | 0.015 ± 0.006 |

N.D. = not determined

As further shown in FIGS. 4-7, mixtures of the non-ionic polar polymers PVP and PEO with liposomes resulted in at least as great a reduction in sliding friction coefficients μ as did immersion in mixtures of the ionic polymer hyaluronic acid with liposomes.

These results indicate that solutions containing ionic or non-ionic water-soluble polymers and the liposomes resulted in friction coefficient values which were substantially lower than the friction coefficient values obtained for either component alone, thus demonstrating a synergistic effect.

These results further indicate that SUV liposomes are highly effective at reducing friction coefficients (as are MLV liposomes described in Example 1) in combination the polar polymers.

As further shown in FIG. 4, a mixture of PEO and DMPC SUVs was particularly effective at reducing sliding friction coefficients of Etafilcon A hydrogel, whereas PEO alone had no effect on the sliding friction coefficient at a relatively low load (3 grams), and resulted in an increased sliding friction coefficient at a higher load (10 grams).

Similarly, as shown in FIG. 7, a mixture of PEO and HSPC SUVs was particularly effective at reducing sliding friction coefficients of Narafilcon A hydrogel, whereas PEO alone resulted in increased sliding friction coefficients.

These results surprisingly indicate a particularly strong synergy (at reducing friction coefficients) between PEO (which is not effective at reducing friction coefficients by itself) and liposomes of different types, and on different surfaces.

Some Non-Limiting Mechanistic Insights:

Without being bound by any particular theory, the following provides a tentative explanation of the results presented above.

The reduction in the friction coefficient upon immersion in polar polymer solution and a subsequent rinse in B&L saline or PBS may be regarded as evidence of an interaction and possible attachment of the polar polymer to the surface of the hydrogel.

The higher reduction (relative to saline and to polar polymer solutions) in the friction coefficient upon immersion in liposomes solution and a subsequent rinse in B&L saline or PBS may be regarded as evidence of coverage of the hydrogel surface.

PC liposomes are well known to act as efficient boundary lubricants, hence the (generally observed) reduction in μ relative to $\mu_0$.

It is assumed that at relatively low pressures the DMPC lipids provide better lubrication than the HSPC, possibly because that at 36-37° C., the DMPC are in their liquid disordered (LD) phase ($T_M$(DMPC)=24° C.) and hence are more highly hydrated than the HSPC, which at 36-37° C. is in its solid ordered (SO) phase ($T_M$(HSPC)=53° C.), whereas at higher temperatures (including those used in previous studies), the situation is reversed, and HSPC liposomes are the better lubricants since their bilayers are more robust than the DMPC ones [Goldberg, R., et al., *Advanced Materials*, 2011, 23:3517-3521; Sorkin, R., et al., *Biomaterials*, 2013. 34:5465-5475]. This may explain the differences in the relative efficacy of DMPC and HSPC liposomes under loads of 3 grams and 10 grams, for example, as shown in Table 1.

When the hydrogel lenses are immersed in a mixture of the liposomes and polar polymer, polar polymer adsorbs on the hydrogels and, in this surface-attached form, complexes with the lipids to form highly lubricating boundary layers.

These findings are further supported by the studies described in Examples 2 and 3 below.

These findings are also qualitatively consistent with the somewhat weaker effect that HA has either on its own or, synergistically, with the liposomes, when Etafilcon hydrogels (HEMA+MA groups) are used relative to Narafilcon hydrogels (silicone).

The Etafilcon hydrogel is slightly negatively charged due to the methacrylic acid (MA) groups, whereby the Narafilcon is uncharged. HA exhibits both negative charge and hydrophobicity. It is therefore assumed that while HA may interact via hydrophobic and electrostatic interactions, it adheres more weakly to negatively-charged surfaces such as HEMA. This lower absorbance of HA on the Etafilcon accounts for the weaker reduction in friction for Etafilcon vs. Narafilcon, both when HA alone is used, and when it is used together with liposomes in the immersing solutions, thus indicating a role for HA absorbance to the hydrogel surface in reducing friction coefficient and increasing lubricity.

Example 2

Phosphatidylcholine Liposomes-Hyaluronic Acid Surface Complexes

Introductory Comments

The origin of the boundary lubrication in mammalian synovial joints has been studied for decades but a generally accepted consensus is still elusive. HA is one of the main macromolecules composing the cartilage tissue and, anchored by entanglements within the collagen network or by lubricin within the superficial zone (SZ), is present also at its outer interface with the synovial cavity, as schematically indicated in Background art FIG. 4. Phospholipids are present both in the synovial fluid (SF) and in the cartilage superficial zone, and indeed DPPC has been suggested as being among the most abundant phospholipids both in SF and in articular cartilage.

In addition to lubricin, both phospholipids and HA have long been implicated in cartilage boundary lubrication. Separately, the interactions between HA and DPPC lipids have been studied independently by several groups.

Herein, a combined effect of HA and phospholipids on the sliding friction coefficient of surfaces, at pressures mimicking those of articular joints, has been studied.

Materials and Methods

Materials:

Water for the SFB experiments and the AFM imaging under water was purified with a Barnstead water purification system (Barnstead NANOpure Diamond, resistivity=18.2MΩ, total organic content (TOC)<1 ppb.

Ruby Muscovite mica grade 1 was obtained from S & J Trading, Inc.,

NY was utilized for the SFB experiments and for the AFM and Cryo-SEM imaging.

Avidin from egg white (A9275) was obtained from Sigma Aldrich, Israel.

Potassium Nitrate salt (purity>99.99%) was obtained from Merck;

DPPC lipids were obtained from Lipoid GmbH;

medical-grade HA (0.5 to 1.5 MDa) for the biotinylation was obtained from Genzyme;

non-biotinylated HA (1 MDa) was obtained from Lifecore Biomedical;

biotin-LC-hydrazide and EDAC were obtained from Pierce and Warriner, Chester, UK.

Biotinylation of HA:

The biotinylation of HA was performed as described in detail in Mahoney, D. J., Blundell, C. D. & Day, A. J. [*Journal of Biological Chemistry* 2001, 276:22764-22771] and Seror et al. [Biomacromolecules, 2011, 12(10):3432-3443]. In brief, 5 mg of HA was dissolved overnight in 0.1M MES, pH 5.5, at a concentration of 5 mg/ml. 13 µl of a solution of 25 mg/ml EDAC in 0.1M MES, pH 5.5, were then added, followed by addition of 20 µl of 50 mM biotin-LC-hydrazide in dimethyl sulfoxide. The reaction mixture was mixed by rotation at room temperature overnight, and was thereafter dialyzed extensively against water and particulate material removed by centrifugation (12,000×g for 1 minute).

The concentration of the bHA was determined using the metahydroxybiphenyl reaction [Blumenkrantz, N. & Asboehan, G. (1973) *Analytical Biochemistry* 54, 484-489] relative to standards made from HA dried in vacuo over cobalt chloride. The bHA (in 0.02% (w/v) NaAzide) was stored at 4° C.

Liposomes Preparation:

Multilamellar vesicles (MLVs) were prepared by hydrating DPPC at 70-75° C. (above its solid-ordered-to-liquid-disordered transition temperature $T_M$=41° C.). MLVs were then downsized to form small unilamellar vesicles (SUVs), about 80 nm in diameter, by stepwise extrusion through polycarbonate membranes starting with a 400 nm and ending with 50 nm-pore-size membrane, using a Lipex 100 mL extruder system (Northern Lipids, Vancouver, Canada). The size distribution of the SUV was determined by dynamic light scattering.

Atomic Force Microscopy (AFM):

Avidin-bHA-DPPC-Coated Mica:

Freshly cleaved mica was glued on a Petri dish and soaked in 0.01 mg/ml avidin aqueous solution for about 30 minutes and then rinsed in water for about 1-2 minutes. The sample was then covered with 49 µg/ml bHA solution and kept in a humidity controlled chamber for several hours. After rinsing the sample with excess of water, the Petri dish was filled with 5 ml of water, to which 0.2 ml of 15 mM suspension of DPPC liposomes (SUVs, prepared as described hereinabove) was added. After overnight adsorption the samples were rinsed in water and scanned with an Asylum MFP3D under pure water using a Veeco-SNL tip (radius of about 2 nm).

HA-DPPC Liposomes Mixed in the Bulk:

1 mg/ml HA and 1 mg/ml DPPC liposomes in the form of SUV liposomes (prepared as described hereinabove) were stirred together in the dark for 24-48 hours at a temperature of about 60-70° C. (above the liposomes' $T_M$), in accordance with a published protocol [Pasquali-Ronchetti, I., Quaglino, D., Mori, G. & Bacchelli, B. (1997) *JOURNAL OF STRUCTURAL BIOLOGY* 120, 1-10]. A freshly cleaved mica surface, previously glued on a Petri dish, was covered with the HA-DPPC solution (after cooling to room temperature) and kept overnight in a humidity controlled chamber. The sample was then rinsed with water, while avoiding exposure to air, and scanned as described above.

AFM samples of both configurations were identical to the surfaces used in the SFB measurements.

SFB Measurement Procedure:

The Surface Force Balance (SFB) measurements were performed as previously described [Klein, J. & Kumacheva, E. (1998) *Journal of Chemical Physics* 108, 6996-7009; Klein, J. (1983) *Journal of the Chemical Society-Faraday Transactions* 179, 99; Raviv, U. & Klein, J. (2002) *Science* 297, 1540-1543], and as schematically illustrated in FIG. 10C, involving measurement of normal and shear interactions between molecularly smooth sheets of mica at separation D (whose absolute value is measured to ±2-3 Å).

Avidin-bHA-DPPC-Coated Mica:

HA was attached to the substrate as follows: following calibration at bare-mica/bare-mica contact, the surfaces were soaked in 0.01 mg/ml avidin aqueous solution for about 30 minutes and then rinsed in water for 1-2 minutes. Attachment of HA was achieved by interacting lightly biotinylated HA (bHA) with the avidin on the mica via the avidin-biotin interaction (and, partly, via electrostatic interactions between the negative HA and the positive avidin), as previously described [Seror et al. (2011) *Biomacromolecules* 12, 3432-3443; Seror et al. (2012) *Biomacromolecules* 13, 3823-3832].

Normal and shear interactions between the avidin-bearing and, following that, between avidin-HA-bearing surfaces were generally measured as controls to ensure the integrity of the surface layers prior to introduction of the liposomes. Samples where contaminant-free attachment of HA on the mica was indicated were used in the next stage.

The HA-coated mica surfaces on their lenses were immersed overnight in 10 ml of pure water into which 400 μl of 15 mM of a suspension DPPC liposomes (SUVs, prepared as described hereinabove) was added, and then rinsed in 400 ml of pure water and remounted in the SFB as close as possible to their original position.

Normal and shear interactions were then measured between the avidin-bHA-DPPC bearing surfaces. Finally, water was substituted with 0.15 M $KNO_3$ solution and normal and shear interactions were measured again.

The results are based on 5 different experiments and 2 to 4 different contact positions on each experiment. The mean pressure P was evaluated as $P=F_n/A$, where $F_n$ is the applied normal force; the contact area $A=\pi a^2$ or $\pi ab$ where a and b are principal radii of the circular (a=b) or elliptical contact area arising from elastic flattening of the glue beneath the mica sheets (measured directly from the flattening of the interference fringes [See, Chen et al. (2009) *Science* 323, 1698-1701; Goldberg et al. (2011) *Advanced Materials* 23, 3517-3521; Sorkin et al. (2013) *Biomaterials* 34, 5465-5475]. An uncertainty of ±(15-20) % in P due to uncertainties of order 10% in the measured radii, was estimated.

Results

AFM Characterization:

FIG. 9A (main) presents an AFM micrograph of a mica surface after overnight incubation in a solution of DPPC-SUVs and HA, which was previously mixed for 48 hours at 60° C. in the dark, followed by rinsing in water, demonstrating that the SUVs are adsorbed in a close-packed configuration on the surface. Inset (i) in FIG. 9A shows the mica surface after overnight incubation in a solution of DPPC-SUVs alone, which previously mixed for 48 hours at 60° C. in the dark, followed by rinsing in water. Inset (ii) in FIG. 9A is CRYO-SEM figure, taken from Sorkin et al. [(2013) *Biomaterials* 34, 5465-5475], and showing part of a cryo-SEM micrograph of mica following incubation in a (HA-free) DPPC-SUV dispersion in water at room temperature.

As shown in FIG. 9A, there is little difference between the three surface configurations, demonstrating that any interaction of HA with the DPPC-SUVs in the bulk dispersion leads to little change in their interactions with the mica. It is to be noted that due to compression by the tip, the AFM measurements indicate vesicle dimensions normal to the surfaces that are likely to be considerably compressed relative to their unperturbed thickness (see, Goldberg et al. (2011) supra).

FIG. 9B presents AFM micrographs of an avidin-bHA-bearing-mica surface following incubation in (HA-free) DPPC-SUV dispersion. As shown therein, a very different structure compared to those presented in FIG. 9A is observed, whereby the surface is densely covered with elongated, beads-on-string-like structures of around 6-10 nm thickness; two such contours are indicated as a guide to the eye. The substantial difference between these structures and the adsorbed vesicles when HA is in the bulk rather than on the surface is highlighted by the inset of FIG. 9B, which shows, on the same scale, one such vesicle taken from the AFM micrograph in FIG. 9A, for comparison. Thus, it is clearly shown that the vesicles, which originally had a DLS-determined radius of about 44±5 nm (or about 30-45 nm as revealed by cryo-SEM when adsorbed on the bare mica surface from the HA-DPPC mixture, as shown in FIG. 9A) have ruptured to form complexes with the surface-attached HA as shown in FIG. 9B.

It is to be noted that the height of the HA-DPPC complexes appears smaller (2.5-3 nm) than their width (6-10 nm). This may be attributed partly to compression by the AFM tip (which may indent the bilayers), and also to the fact that the HA chains are attached to avidin groups (height of about 4-5 nm on the mica [see, Seror et al. (2011) *Biomacromolecules* 12, 3432-3443] and so may be compressed into the gaps therebetween.

FIG. 9C presents a schematic illustration of the obtained complexes, which, without being bound by any particular theory, are assumed to be composed of HA chains, whose uncomplexed thickness is around 0.3-1.5 nm [see, Jacoboni, et al. (1999) *Journal of Structural Biology* 126, 52-58], enclosed by DPPC lipid monolayers or bilayers (about 5 nm thickness for a bilayer).

Surface Interactions:

Normal Surface Forces:

Using the SFB, both normal and shear interaction profiles, $F_n(D)$ and $F_s(D)$ respectively, were measured (see, FIG. 10C) between mica surfaces bearing DPPC attached from incubating solutions containing HA, and forming the two configurations presented in FIGS. 9A and 9B and discussed hereinabove.

FIG. 10A presents the normalized interactions between two HA-DPPC surface complexes (shown in FIG. 9B). The range of interactions varies within about ±10% of the mean range between different experiments, but less than that within different contact points of a given experiment. As shown in FIG. 10A, a common trend is recognizable in the majority of the profiles. Generally, first approaches are longer ranged with repulsion starting already at surface separation around D of about 150-250 nm (full symbols in FIG. 10A), while in second or subsequent approaches (crossed symbols in FIG. 10A) the surfaces start to repel each other only at a separation around D of about 60-120 nm.

As shown in FIG. 10B, first profiles often present a kink at a separation of between 60-100 nm (that is, the forces remain roughly constant over this separation range), after which they continue to increase monotonically. The kink may be interpreted as squeezing out of the residual liposomes by the compressing surfaces.

Receding force profiles (open symbols in FIG. 10A) have a similar trend to second approaching profiles (crossed symbols in FIG. 10A). These features may readily be attributed to residual loose, weakly attached vesicles overlaying the firmly-attached HA-DPPC surface complex seen in FIG. 9A, arising from inadequate rinsing following incubation. These loose vesicles may be removed by the compression and the shearing motion during the approach, leading to shorter interaction range at separation and subsequent approaches.

The final separation at high pressures reached in first and subsequent approaches is very similar: D=22±3 nm and 23±3 nm, respectively, or some 11 nm/surface. This may be attributed to the thickness of the avidin (about 4 nm), covered by HA (about 0.9 nm) complexed with a DPPC bilayer (about 4-5 nm), which account for some 9-10 nm before consideration of any chain overlap on the surface (see, e.g., FIG. 9C).

Red full and crossed symbols in FIG. 10A are respectively first and second approaches of the avidin-bHA-DPPC bearing surfaces in 0.15 M salt solution. The shorter onset range of the repulsion in salt solution (about 100 nm) relative to pure water (150-200 nm) is attributed to removal of residual intact liposomes, due both to shear in the pure water prior to adding salt, and to the effect of replacing pure water by the salt solution which is effectively an additional rinsing stage.

Lateral/Frictional Forces:

FIGS. 11A and 12 present the shear force vs. time traces, $F_s(t)$, between mica surfaces, for the configuration where the mica surfaces are coated with the HA-DPPC complexes (shown in FIGS. 9B and 9C), recorded directly from the SFB, across water and across 0.15M $KNO_3$, respectively. In FIGS. 11A and 12, the top saw tooth traces represent the back and forth motion of the upper surface as a function of time, while traces below are the corresponding shear forces between the surfaces recorded at different mean pressures P (arising from different loads $F_n$) and D values, at given contact points. The plateaus in the shear force traces correspond to sliding of the surfaces.

FIG. 11B shows variation of the shear force under high compression (P=161 atm, D=20 nm) over some 3 orders of magnitude in the sliding velocity $v_s$, indicating little change in $F_s$, a signature of boundary lubrication.

FIG. 11C shows that the surfaces are robust to prolonged sliding at high P values, as $F_s$ does not increase over time (for periods up to an hour), and may even decrease. This decrease may be attributed to rearrangement under sliding of the surface-attached complexes to a less dissipative orientation.

FIG. 13A presents a summary of the shear force vs. load results and shows an initial rapid rise in the friction at lower loads (and pressures). This phenomenon is attributed to the viscous dissipation arising from shear of the loosely-attached liposomes on top of the HA-DPPC complex attached to the surface, once the surfaces are compressed to the range of steric repulsion at D<ca. 100 nm (see, FIGS. 10A-C). On shear at progressively higher pressures, the loosely attached vesicles are, as noted above, squeezed out of the contact region, as indicated by the lower shear forces on a second approach at a given contact point (prior to reaching the 'hard wall' separation). At the highest compressions—of order 50-100 atm or higher—the surfaces reach their limiting separation of 22±2 nm, corresponding to $F_n$>ca. 10 mN (see $F_n$(D) profile in FIGS. 10A-C). At these compressions the HA-DPPC complexes, firmly attached to each surface, are sliding directly past each other, and the effective friction coefficient $\mu=F_s/F_n$, while showing some scatter (see shaded region in FIG. 13A), has a value $\mu$ of about $(1.5\pm1)\times10^{-3}$ (taken over all experiments and contact points).

FIG. 13B presents a comparison of the $F_s$ vs. $F_n$ variation between mica surfaces with an avidin-bHA layer but in the absence of any added liposomes, highlighting the orders of magnitude decrease in friction once the surface attached HA is complexed with DPPC.

The data with added salt (FIG. 13A, red symbols) shows a similar trend, while the friction coefficient is slightly higher. This is attributed to a reduced hydration level of the phosphocholine headgroups in the presence of high salt and consequently a less efficient hydration lubrication mechanism (as previously described; see, e.g., Chen et al. (2009) *Science* 323, 1698-1701). At the higher loads ($F_n$>ca. 2-3 mN, corresponding to D of about 22 nm, P>ca. 50 atm) where the surface-attached HA-DPPC complexes are sliding directly past each other, the friction coefficient $\mu$ is about $(7\pm1)\times10^{-3}$.

Overall, the findings described herein indicate that DPPC lipids, introduced into the system as liposomes, complex with HA when HA is attached to the interacting surfaces, and these HA-DPPC complexes result in robust boundary layers that provide excellent lubrication (down to friction coefficient $\mu$ of about $10^{-3}$) up to mean contact pressures of about 200 Atm. The exceptional lubrication obtained with such complexes substantially exceeds the lubrication obtained when HA alone is attached to the surfaces, as seen in FIG. 13B.

When hydrogenated soy phosphatidylcholine (HSPC) SUVs rather than DPPC SUVs were used, the obtained results (not shown) were results to those shown in FIGS. 9A-B, 10A-B, 11A-C, 12 and 13A-B. This is suggestive, as HSPC, while not native to cartilage, is a saturated diacyl PC, with predominantly 18:0 (~85%) and 16:0 (~15%) fatty acyl tails; and such saturated 16:0 and 18:0 tails comprise some 30% of the PCs at the cartilage surface.

It is noted that HA is negatively charged, and thus the dipolar phosphocholine head-groups of phosphatidylcholine lipids (such as DPPC) presumably experience a dipole-charge attraction to the polysaccharide. Since the surface exposed by the HA-DPPC complexes must be hydrophilic, it is assumed that the structure of these complexes is either a bilayer, where the lipid headgroup attaches to the negative charge on the HA, or a DPPC monolayer where the acyl tails of the lipid attach via hydrophobic interactions to the hydrophobic patches on the HA chains (about 8 CH unit per disaccharide [see, Laurent, T. (1989) *Ciba Foundation Symposia* 143, 1-5; Scott, J. E. (1989) *Ciba Foundation Symposia* 143, 6-20].

HA-DPPC complexes that have been imaged with negative-staining [Pasquali-Ronchetti, et al., *Journal of Structural Biology* 1997, 120:1-10] show that HA complexes with DPPC, augmenting the HA contour thickness.

The width of the HA-DPPC complexes (6 to 10 nm) measured as described herein (see, FIG. 9B) supports either of the two possible configurations described above, i.e. an HA chain surrounded by two bilayers or two monolayers or a combination of the two.

The observations described herein can be regarded as indicating that surface-attached HA chains are coated with DPPC layers exposing their highly hydrated phosphocholine headgroups; thus rendering the mica surfaces coated with such layers invariably wet when withdrawn from water.

When the same DPPC-SUVs are well-mixed with HA in bulk solution rather than attached to the surface, HA does not appear to disrupt the vesicles, as a close packed liposome surface-layer is obtained, which is similar to that obtained in the absence of HA (see, FIG. 9A).

Significantly, a very low friction coefficient was measured between mica surfaces having the HA-DPPC complexes at high pressures. At pressures of about 50 Atm (comparable to mean pressures in major joints), any residual loose vesicles have been squeezed out of the gap, and the polysaccharide-lipid complexes are in direct contact as they slide past each other. The robustness to sliding at high compression is demonstrated by the constancy (or even decrease) of the friction, following an hour of continuous sliding (see, FIG. 11C), and the weak variation of the friction with sliding velocity over 3 orders of magnitude in the latter, demonstrated in FIG. 11B, provides a further indication of boundary lubrication. The low friction between the HA-DPPC complexes, as they slide past each other, is presumably attributed to the hydration lubrication mechanism, which, further presumably, arises from the fluid nature of tenaciously-held hydration layers, particularly for the case of the highly-hydrated phosphocholine groups exposed by these surface structures.

The results presented herein are brought, inter alia, as an explanation of the mode of action of the HA and liposomes solutions described in Example 1 in the context of contact lens. That is, HA attaches to the surface of the lenses (e.g., by adsorption), and the liposomes then complex with this surface-attached HA to form the robust, highly-lubricating boundary layer.

These results further demonstrate that using HA and liposomes for providing lubricity is efficiently performed by attaching or tethering HA to the surface to be lubricated (e.g., a surface which does not adsorb HA effectively), such that the liposomes interact with the tethered HA to form the HA-lipid complexes comprising the highly-lubricating boundary layer.

These results further provide a clearer understanding of the boundary lubrication of joints. The articular cartilage collagen network is known to be permeated with HA, which in time diffuses through the outer cartilage surface into the synovial cavity [Klein, J. (2006) Proceedings of the Institution of Mechanical Engineers Part J-Journal of Engineering Tribology 220, 691-710]. During its transport through this interface the HA may still be slowed down by entanglements within the cartilage SZ (superficial zone) (as indicated in Background art FIG. 8), or, more likely, be held at the surface by its interactions with SZ lubricin, and will complex with the phosphocholines (PCs) that are ubiquitous both in cartilage and in the SF. As shown herein, such complexed, surface-attached HA-PC structures can provide robust boundary lubrication with friction coefficients μ of about $10^{-3}$, mimicking those in the major mammalian joints up to the highest pressures in such joints.

These findings indicate that HA, lubricin and phospholipids possibly act together to provide the remarkable lubrication of articulating cartilage: Superficial zone lubricin is responsible, at least in part, for tethering HA at the cartilage surface; the surface-bound HA, as shown herein, in turn complexes with the cartilage/SF PCs; and these boundary HA/PC complexes, acting via the hydration lubrication mechanism, provide the low friction that is the hallmark of healthy synovial joints, and further account for the natural replacement of the boundary layers as they wear away (since HA originating either in the cartilage chondrocytes or in the SF is continuously permeating and diffusing through the cartilage space, or through the SF, to arrive at the superficial zone and at the cartilage outer surface, where, held by the SZ lubricins, it may complex with phospholipids to replenish the boundary layer).

These findings further suggest that efficient treatment of arthritic (e.g., osteoarthritic) joints can be performed by attaching hyaluronic acid to the surface of a joint (e.g., to cartilage) via a linker designed to bind to hyaluronic acid and to collagen (e.g., collagen II), and administering liposomes. Such a linker optionally comprises a collagen-binding peptide (e.g., collagen II-binding peptide) for binding to collagen in the joint (e.g., in cartilage at the articular surface) and a functional group or moiety which binds covalently and/or non-covalently to the hyaluronic acid. Optionally, the linker comprises a hyaluronic acid-binding peptide which binds to the hyaluronic acid. The hyaluronic acid is optionally administered with at least one linker bound thereto, that is, in a form of a modified hyaluronic acid, for example, modified hyaluronic acid comprising which comprises at least one collagen-binding peptide (e.g., collagen II-binding peptide).

Example 3

Lubrication of Tendons by Hyaluronic Acid and Liposomes

Modified hyaluronic acid (HA) was modified by conjugating dopamine (DN) to the carboxylic acid groups of HA by a 1-ethyl-3-(3'-dimethyl aminopropyl) carbodiimide (EDC) coupling reaction. The modified HA thus comprised dihydroxyphenyl (catechol) groups, which have been reported to promote binding to organic surfaces (including amine-containing surfaces) via covalent bond formation, as well as to inorganic surfaces via strong non-covalent binding [Lee et al., PNAS 2006, 103:12999-13003; Brodie et al., Biomedical Materials 2011, 6:015014].

Briefly, 0.5 gram of HA was dissolved in 50 ml of PBS solution and the pH was adjusted to 5.5 using 1 N HCl solution. In the solution, 40 mg (0.05 mmol) of EDC and 94 mg (0.05 mmol) of dopamine hydrochloride was added and the pH of the reaction solution was maintained at 5.5 for 2 hours with 1.0 N HCl and 1.0 N NaOH. Then, the solution was dialyzed against water for 2 days and was subsequently lyophilized, which resulted in a white powder.

DN levels in the HA-DN conjugate were analyzed by ultraviolet (UV) spectrophotometry and nuclear magnetic resonance (NMR) analysis. For UV analysis, a solution of 1 mg/ml in water was prepared. For 1H-NMR, the sample was dissolved in deuterated water ($D_2O$) for 3 hours at concentrations of 2 mg/ml. The spectra were recorded at 298 K and 500 MHz for 1H-NMR analysis. As shown by UV spectroscopy, an absorption band at approximately 280 nm appeared for the HA-DN conjugate, which was not observed for unmodified HA. Based on this band, it was determined that the concentration of dopamine units in the HA-DN solution was about 0.075 mg/ml, which indicated that the degree of dopamine substitution in the synthesized conjugate was about 19%. The catechol content (as a molar percentage, relative to repeating disaccharide units of HA) in HA-DN was determined by NMR analysis from the integral area ratio calculation f=a/b, where a is the integral area of the peaks at around 7 ppm, which corresponds to the amount of H in the aromatic rings of grafted catechol moieties, and b is the integral area of the peaks at about 2.0 ppm, which represents the amount of H in the methylene of polymeric backbone. The degree of conjugated dopamine in the resultant polymer was about 18% as determined by NMR analysis, which is consistent with the result of UV analysis. Other batches of HA-DN were found to have about 4% or 12% conjugated dopamine.

The friction coefficient characterizing friction between a chicken tendon and its sheath under sliding condition was determined by preparing tendon/sheath samples as depicted in FIGS. 14A-14E and measuring gliding resistance using a tribometer system depicted in FIG. 15.

The tendons were treated with solutions of hyaluronic acid (HA), hydrogenated soy phosphatidylcholine (HSPC) small unilamellar vesicles (SUVs), HSPC SUVs in combination with HA, or HSPC SUVs in combination with dopamine-functionalized HA (HA-DOPA, prepared as described hereinabove), in phosphate buffer saline (PBS). Control tendons were treated with PBS alone.

Before treatment, the friction force for all tendons was measured in PBS, under zero load force for calibration. Then the PBS was replaced with the treatment solution, and the tendon was soaked in the treatment solution at 37° C. for 20 minutes. After 20 minutes, the treatment solution was replaced with PBS and the friction force between each tendon and its sheath was measured.

As shown in FIGS. 16-18, HA alone and HSPC liposomes alone each reduced the friction coefficient of tendons, but the combination of HSPC liposomes with HA or dopamine-functionalized HA resulted in a reduction in the friction coefficient which was far more robust to repeated cycles of friction than the reduction resulting from HA alone or HSPC liposomes alone, under loads of both 40 grams (FIGS. 16 and 18) and 80 grams (FIGS. 17 and 18). As further shown therein, dopamine-functionalized HA resulted in a considerably greater reduction in the friction coefficient than did unmodified HA.

These results confirm that liposomes and polymers such as HA synergistically reduce friction in physiological systems, and further indicate that polymers comprising functional groups which enhance affinity to a physiological surface such as a connective tissue are even more effective at reducing friction in such a system.

In order to assess the mechanism by which unmodified and dopamine-functionalized HA act in synergy with liposomes, HSPC SUVs were labeled with the lipophilic fluorescent dye DiI (1,1'-dioctadecyl-3,3,3'3'-tetramethylindocarbocyanine) and the amount of lipids on tendon surfaces treated with HSPC alone or with unmodified and dopamine-functionalized HA was evaluated by fluorescence measurements.

As shown in FIGS. 19 and 20A-20C, unmodified and dopamine-functionalized HA both increased binding of HSPC to tendon surfaces, with dopamine-functionalized HA being considerably more effective in this respect than unmodified HA. These results indicate that the synergistic effect of liposomes and polymers such as HA is associated with enhancement by the polymer of the affinity of liposome lipids to a surface, and that polymers with enhanced affinity to the surface are more effective at enhancing affinity of the lipids the surface.

Binding of liposome lipids to additional surfaces was evaluated by fluorescent measurements, using DiI-labeled liposomes as described hereinabove, and a gelatin-methacrylate hydrogel surface. Unmodified HA was used, as was HA functionalized with different levels of dopamine, 4% and 18% dopamine (relative to the number of repeating (disaccharide) units of HA).

As shown in FIG. 21, unmodified and dopamine-functionalized HA both increased binding of HSPC to tendon surfaces, with dopamine-functionalization of HA enhancing the ability of HA to increase HSPC binding in a manner which correlated to the level of dopamine groups.

These results indicate that functionalized polymers such as HA-DOPA facilitate liposome lipid binding to various surfaces.

Example 4

In Vivo Effects of Dopamine-Functionalized Hyaluronic Acid and Liposomes

A solution containing 11 mM of HSPC small unilamellar vesicles (SUVs) and 1.6 mg/ml of dopamine-functionalized hyaluronic acid (HA-DOPA; prepared according to procedures described in Example 3) in phosphate buffer saline (PBS) is injected into animal joints. The level of dopamine groups in the HA-DOPA is 12% (relative to the number of repeating (disaccharide) units of HA). For comparison, corresponding solutions containing HSPC SUVs and unmodified hyaluronic acid and/or HSPC SUVs without HA are also injected into animal joints.

Retention times of HSPC liposomes injected into joints with HA-DOPA, unmodified HA and/or without HA are compared, by labeling the liposomes with a fluorescent dye (e.g., IR-783, obtained from Sigma-Aldrich) and measuring fluorescent intensity over time.

Therapeutic parameters associated with decreased friction in the joints are optionally measured in order to evaluate the effect of the administered solution in vivo.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of reducing a friction coefficient of a surface, the method comprising contacting the surface with a solution comprising at least one water-soluble polymer, liposomes, and an aqueous carrier, wherein said water-soluble polymer and said surface are selected such that said water-soluble polymer is attachable to said surface, and wherein said at least one water-soluble polymer comprises a modified water-soluble polymer which further comprises at least one functional group for attaching said polymer to said surface.

2. The method of claim 1, wherein said functional group comprises a dihydroxyphenyl group.

3. The method of claim 1, wherein said at least one water-soluble polymer comprises a non-ionic polymer.

4. The method of claim 1, wherein said at least one water-soluble polymer comprises an ionic polymer.

5. The method of claim 1, wherein said surface is a physiological surface, and said carrier is a physiologically acceptable carrier.

6. The method of claim 5, wherein said surface is an articular surface of a synovial joint.

7. The method of claim 6, being for use in the treatment of a synovial joint disorder associated with an increased friction coefficient of an articular surface in the synovial joint.

8. A method of reducing a friction coefficient of a surface, the method comprising attaching at least one water-soluble polymer to the surface, and contacting said at least one water-soluble polymer with liposomes, thereby effecting coating of the surface by an amphiphilic lipid of said liposomes, wherein said at least one water-soluble polymer comprises a modified water-soluble polymer which further comprises at least one functional group for attaching said polymer to said surface, wherein said amphiphilic lipid comprises at least one charged group, and wherein at least a portion of molecules of said amphiphilic lipid coating said surface are oriented such that charged groups thereof face outwards at said surface.

9. The method of claim 8, wherein said attaching at least one water-soluble polymer to the surface is effected prior to said contacting said at least one water-soluble polymer with liposomes.

10. The method of claim 8, wherein said at least one water-soluble polymer comprises a non-ionic polymer.

11. The method of claim 8, wherein said at least one water-soluble polymer comprises an ionic polymer.

12. The method of claim 8, wherein said surface is a physiological surface.

13. The method of claim 12, wherein said surface is an articular surface of a synovial joint and/or a surface of a tendon.

14. The method of claim 13, being for use in the treatment of a synovial joint disorder associated with an increased friction coefficient of an articular surface in the synovial joint.

15. An article of manufacture comprising a composition-of-matter, the composition-of-matter comprising a substrate coated, on at least a portion of a surface thereof, by at least one water-soluble polymer, the at least one water-soluble polymer being coated by an amphiphilic lipid comprising at least one charged group, wherein at least a portion of molecules of said amphiphilic lipid are oriented such that charged groups thereof face outwards at a surface of the composition-of-matter.

16. The method of claim 7, wherein said synovial joint disorder is selected from the group consisting of arthritis, traumatic joint injury, locked joint, and joint injury associated with surgery.

17. The method of claim 14, wherein said synovial joint disorder is selected from the group consisting of arthritis, traumatic joint injury, locked joint, and joint injury associated with surgery.

18. The method of claim 1, wherein said water-soluble polymer is selected from the group consisting of a hyaluronic acid, a polyvinylpyrrolidone and a polyethylene oxide.

19. The method of claim 8, wherein said water-soluble polymer is selected from the group consisting of a hyaluronic acid, a polyvinylpyrrolidone and a polyethylene oxide.

* * * * *